(12) United States Patent
Mitchell et al.

(10) Patent No.: US 8,016,861 B2
(45) Date of Patent: Sep. 13, 2011

(54) VERSATILE POLYAXIAL CONNECTOR ASSEMBLY AND METHOD FOR DYNAMIC STABILIZATION OF THE SPINE

(75) Inventors: Steven T. Mitchell, Pleasant Hill, CA (US); Charles J. Winslow, Walnut Creek, CA (US); John J. Flynn, Walnut Creek, CA (US); James F. Zucherman, San Francisco, CA (US); Ken Y. Hsu, San Francisco, CA (US); Henry A. Klyce, Piedmont, CA (US); H. Adam R. Klyce, Berkeley, CA (US)

(73) Assignee: Spartek Medical, Inc., Alameda, CA (US)

( * ) Notice: Subject to any disclaimer, the term of this patent is extended or adjusted under 35 U.S.C. 154(b) by 167 days.

(21) Appl. No.: 12/566,485

(22) Filed: Sep. 24, 2009

(65) Prior Publication Data

US 2010/0030273 A1 Feb. 4, 2010

Related U.S. Application Data

(63) Continuation-in-part of application No. 12/130,395, filed on May 30, 2008.

(60) Provisional application No. 61/100,625, filed on Sep. 26, 2008, provisional application No. 61/100,593, filed on Sep. 26, 2008, provisional application No. 61/119,651, filed on Dec. 3, 2008, provisional application No. 61/122,658, filed on Dec. 15, 2008, provisional application No. 61/144,426, filed on Jan. 13, 2009, provisional application No. 61/167,789, filed on Apr. 8, 2009, provisional application No. 61/217,556, filed on Jun. 1, 2009, provisional application No. 61/225,478, filed on Jul. 14, 2009, provisional application No. 61/031,598, filed on Feb. 26, 2008, provisional application No. 61/057,340, filed on May 30, 2008.

(51) Int. Cl.
*A61B 17/70* (2006.01)
*A61B 17/86* (2006.01)

(52) U.S. Cl. .................... 606/264; 606/305
(58) Field of Classification Search .......... 606/246–279, 606/300–308
See application file for complete search history.

(56) References Cited

U.S. PATENT DOCUMENTS 4,041,939 A 8/1977 Hall ................... 128/69
(Continued)

FOREIGN PATENT DOCUMENTS

DE 2649042 B1 10/1976
(Continued)

OTHER PUBLICATIONS

Mekanika, Inc. Website, 2003; Mekanika—The Spinal Stabilization Company, product description for Modulus System, 2 pages, <http://mekanika.com/htm/modsystem.htm>.

(Continued)

*Primary Examiner* — Pedro Philogene
(74) *Attorney, Agent, or Firm* — Fliesler Meyer LLP

(57) ABSTRACT

Versatile polyaxial connector assemblies are provided for a dynamic stabilization system which supports the spine while providing for the preservation of spinal motion. Embodiments of the dynamic stabilization system include versatile polyaxial connectors in addition to bone anchors, a deflection system and a vertical rod system. The bone anchors connect the construct to the spinal anatomy. The deflection system provides dynamic stabilization while reducing the stress exerted upon the bone anchors and spinal anatomy. The vertical rod system spans different levels of the construct. The versatile polyaxial connectors include connectors mounted coaxially and/or offset with the bone anchors to adjustably connect the deflection system, vertical rod system and bone anchors allowing for safe, effective and efficient placement of the construct relative to the spine.

15 Claims, 37 Drawing Sheets

U.S. PATENT DOCUMENTS

| | | | |
|---|---|---|---|
| 4,065,817 A | 1/1978 | Branemark et al. | 3/1.91 |
| 4,274,401 A | 6/1981 | Miskew | |
| 4,347,845 A | 9/1982 | Mayfield | 128/303 |
| 4,369,770 A | 1/1983 | Bacal et al. | 128/69 |
| 4,382,438 A | 5/1983 | Jacobs | 128/69 |
| 4,409,968 A | 10/1983 | Drummond | 128/69 |
| 4,411,259 A | 10/1983 | Drummond | 128/69 |
| 4,422,451 A | 12/1983 | Kalamchi | 128/69 |
| 4,479,491 A | 10/1984 | Martin | 128/92 |
| 4,567,885 A | 2/1986 | Androphy | 128/92 |
| 4,573,454 A | 3/1986 | Hoffman | 128/69 |
| 4,604,995 A | 8/1986 | Stephens et al. | 128/69 |
| 4,611,580 A | 9/1986 | Wu | 128/69 |
| 4,611,581 A | 9/1986 | Steffee | 128/69 |
| 4,611,582 A | 9/1986 | Duff | 128/69 |
| 4,641,636 A | 2/1987 | Cotrel | 128/69 |
| 4,648,388 A | 3/1987 | Steffee | 128/69 |
| 4,653,481 A | 3/1987 | Howland et al. | 128/69 |
| 4,653,489 A | 3/1987 | Tronzo | 128/92 |
| 4,655,199 A | 4/1987 | Steffee | 128/69 |
| 4,658,809 A | 4/1987 | Ulrich et al. | 128/92 |
| 4,696,290 A | 9/1987 | Steffee | 128/69 |
| 4,719,905 A | 1/1988 | Steffee | 128/69 |
| 4,763,644 A | 8/1988 | Webb | 128/69 |
| 4,773,402 A | 9/1988 | Asher et al. | 128/69 |
| 4,805,602 A | 2/1989 | Puno et al. | 128/69 |
| 4,815,453 A | 3/1989 | Cotrel | 128/69 |
| 4,887,595 A | 12/1989 | Heinig et al. | 606/61 |
| 4,913,134 A | 4/1990 | Luque | 128/69 |
| 4,946,458 A | 8/1990 | Harms et al. | 606/61 |
| 4,950,269 A | 8/1990 | Gaines, Jr. | 606/61 |
| 4,955,885 A | 9/1990 | Meyers | 606/53 |
| 4,987,892 A | 1/1991 | Krag et al. | 606/61 |
| 5,005,562 A | 4/1991 | Cotrel | 128/69 |
| 5,024,213 A | 6/1991 | Asher et al. | 128/69 |
| 5,030,220 A | 7/1991 | Howland | 606/61 |
| 5,042,982 A | 8/1991 | Harms et al. | 606/61 |
| 5,047,029 A | 9/1991 | Aebi et al. | 606/61 |
| 5,067,955 A | 11/1991 | Cotrel | 606/61 |
| 5,074,864 A | 12/1991 | Cozad et al. | 606/54 |
| 5,084,049 A | 1/1992 | Asher et al. | 606/61 |
| 5,092,866 A | 3/1992 | Breard et al. | 606/61 |
| 5,102,412 A | 4/1992 | Rogozinski | 606/61 |
| 5,112,332 A | 5/1992 | Cozad et al. | 606/61 |
| 5,113,685 A | 5/1992 | Asher et al. | 72/458 |
| 5,116,334 A | 5/1992 | Cozad et al. | |
| 5,127,912 A | 7/1992 | Ray et al. | 606/61 |
| 5,129,388 A | 7/1992 | Vignaud et al. | 606/61 |
| 5,129,900 A | 7/1992 | Asher et al. | 606/61 |
| 5,147,359 A | 9/1992 | Cozad et al. | 606/61 |
| 5,154,718 A | 10/1992 | Cozad et al. | 606/61 |
| 5,176,680 A | 1/1993 | Vignaud et al. | 606/61 |
| 5,180,393 A | 1/1993 | Commarmond | 623/13 |
| 5,190,543 A | 3/1993 | Schläpfer | 606/61 |
| 5,201,734 A | 4/1993 | Cozad et al. | 606/62 |
| 5,207,678 A | 5/1993 | Harms et al. | 606/61 |
| 5,261,911 A | 11/1993 | Carl | 606/61 |
| 5,261,912 A | 11/1993 | Frigg | 606/61 |
| 5,261,913 A | 11/1993 | Marnay | 606/61 |
| 5,281,222 A | 1/1994 | Allard et al. | 606/54 |
| 5,282,801 A | 2/1994 | Sherman | 606/61 |
| 5,282,863 A | 2/1994 | Burton | 623/17 |
| 5,290,289 A | 3/1994 | Sanders et al. | 606/61 |
| 5,312,402 A | 5/1994 | Schläpfer et al. | 606/53 |
| 5,312,404 A | 5/1994 | Asher et al. | 606/61 |
| 5,344,422 A | 9/1994 | Frigg | 606/61 |
| 5,346,493 A | 9/1994 | Stahurski et al. | 606/61 |
| 5,360,429 A | 11/1994 | Jeanson et al. | 606/61 |
| 5,360,431 A | 11/1994 | Puno et al. | 606/72 |
| 5,374,267 A | 12/1994 | Siegal | |
| 5,380,325 A | 1/1995 | Lahille et al. | 606/61 |
| 5,380,326 A | 1/1995 | Lin | 606/61 |
| 5,382,248 A | 1/1995 | Jacobson et al. | 606/60 |
| 5,385,583 A | 1/1995 | Cotrel | 623/17 |
| 5,387,213 A | 2/1995 | Breard et al. | 606/61 |
| 5,415,661 A | 5/1995 | Holmes | 606/69 |
| 5,429,639 A | 7/1995 | Judet | 606/61 |
| 5,437,672 A | 8/1995 | Alleyne | |
| 5,443,467 A | 8/1995 | Biedermann et al. | 606/65 |
| 5,466,237 A | 11/1995 | Byrd, III et al. | 606/61 |
| 5,474,555 A | 12/1995 | Puno et al. | 606/73 |
| 5,480,442 A | 1/1996 | Bertanoli | |
| 5,487,742 A | 1/1996 | Cotrel | 606/61 |
| 5,496,321 A | 3/1996 | Puno et al. | 606/61 |
| 5,498,264 A | 3/1996 | Schlapfer et al. | 606/72 |
| 5,501,684 A | 3/1996 | Schlapfer et al. | |
| 5,520,689 A | 5/1996 | Schläpfer et al. | 606/61 |
| 5,534,001 A | 7/1996 | Schlapfer et al. | 606/61 |
| 5,536,268 A | 7/1996 | Griss | 606/61 |
| 5,540,688 A | 7/1996 | Navas | 606/61 |
| 5,545,167 A | 8/1996 | Lin | 606/61 |
| 5,549,607 A | 8/1996 | Olson et al. | 606/61 |
| 5,562,737 A * | 10/1996 | Graf | 623/17.14 |
| 5,569,248 A | 10/1996 | Mathews | 606/61 |
| 5,591,166 A | 1/1997 | Bernhardt et al. | |
| 5,601,552 A | 2/1997 | Cotrel | |
| 5,609,592 A | 3/1997 | Brumfield et al. | 606/61 |
| 5,609,593 A | 3/1997 | Errico et al. | 606/61 |
| 5,611,800 A | 3/1997 | Davis et al. | 606/61 |
| 5,624,441 A | 4/1997 | Sherman et al. | 606/61 |
| 5,628,740 A | 5/1997 | Mullane | 606/61 |
| 5,630,816 A | 5/1997 | Kambin | 606/61 |
| 5,643,260 A | 7/1997 | Doherty | 606/61 |
| 5,645,599 A | 7/1997 | Samani | 623/17 |
| 5,651,789 A | 7/1997 | Cotrel | 606/61 |
| 5,653,708 A | 8/1997 | Howland | 606/61 |
| 5,658,284 A | 8/1997 | Sebastian et al. | 606/61 |
| 5,658,285 A | 8/1997 | Marnay et al. | |
| 5,667,506 A | 9/1997 | Sutterlin | 606/61 |
| 5,667,507 A | 9/1997 | Corin et al. | 606/61 |
| 5,669,910 A | 9/1997 | Korhonen et al. | 606/61 |
| 5,672,175 A | 9/1997 | Martin | 606/61 |
| 5,672,176 A | 9/1997 | Biedermann et al. | 606/61 |
| 5,676,665 A | 10/1997 | Bryan | 606/61 |
| 5,676,703 A | 10/1997 | Gelbard | 623/17 |
| 5,681,310 A | 10/1997 | Yuan et al. | |
| 5,681,311 A | 10/1997 | Foley et al. | 606/61 |
| 5,681,319 A | 10/1997 | Biedermann et al. | 606/104 |
| 5,683,391 A | 11/1997 | Boyd | 606/61 |
| 5,683,392 A | 11/1997 | Richelsoph et al. | 606/61 |
| 5,683,393 A | 11/1997 | Ralph | 606/61 |
| 5,688,272 A | 11/1997 | Montague et al. | 606/61 |
| 5,688,273 A | 11/1997 | Errico et al. | 606/61 |
| 5,690,629 A | 11/1997 | Asher et al. | 606/61 |
| 5,690,632 A | 11/1997 | Schwartz et al. | 606/73 |
| 5,690,633 A | 11/1997 | Taylor et al. | 606/73 |
| 5,693,053 A | 12/1997 | Estes | 606/61 |
| 5,697,929 A | 12/1997 | Mellinger | 606/61 |
| 5,700,292 A | 12/1997 | Margulies | 623/17 |
| 5,702,392 A | 12/1997 | Wu et al. | 606/61 |
| 5,702,394 A | 12/1997 | Henry et al. | 606/61 |
| 5,702,395 A | 12/1997 | Hopf | 606/61 |
| 5,702,396 A | 12/1997 | Hoenig et al. | 606/69 |
| 5,702,399 A | 12/1997 | Kilpela et al. | 606/72 |
| 5,702,452 A | 12/1997 | Argenson et al. | 623/17 |
| 5,713,900 A | 2/1998 | Benzel et al. | 606/61 |
| 5,713,904 A | 2/1998 | Errico et al. | 606/73 |
| 5,716,355 A | 2/1998 | Jackson et al. | 606/61 |
| 5,716,356 A | 2/1998 | Biedermann et al. | 606/61 |
| 5,716,357 A | 2/1998 | Rogozinski | 606/61 |
| 5,716,358 A | 2/1998 | Ochoa et al. | 606/62 |
| 5,716,359 A | 2/1998 | Ojima et al. | 606/76 |
| 5,720,751 A | 2/1998 | Jackson | 606/86 |
| 5,725,528 A | 3/1998 | Errico et al. | 606/61 |
| 5,725,582 A | 3/1998 | Bevan et al. | 623/17 |
| 5,728,098 A | 3/1998 | Sherman et al. | 606/61 |
| 5,733,286 A | 3/1998 | Errico et al. | 606/61 |
| 5,735,851 A | 4/1998 | Errico et al. | 606/61 |
| 5,741,254 A | 4/1998 | Henry et al. | 606/61 |
| 5,743,907 A | 4/1998 | Asher et al. | 606/61 |
| 5,743,911 A | 4/1998 | Cotrel | 606/61 |
| 5,752,957 A | 5/1998 | Ralph et al. | 606/61 |
| 5,766,254 A | 6/1998 | Gelbard | 623/17 |
| 5,776,135 A | 7/1998 | Errico et al. | |
| 5,782,833 A | 7/1998 | Haider | 606/61 |
| 5,785,711 A | 7/1998 | Errico et al. | 606/61 |
| 5,797,911 A | 8/1998 | Sherman et al. | 606/61 |

| Patent No. | Date | Inventor | Class |
|---|---|---|---|
| 5,800,435 A | 9/1998 | Errico et al. | 606/61 |
| 5,810,819 A | 9/1998 | Errico et al. | 606/61 |
| 5,863,293 A | 1/1999 | Richelsoph | 606/61 |
| 5,868,745 A | 2/1999 | Alleyne | |
| 5,879,350 A | 3/1999 | Sherman et al. | 606/61 |
| 5,885,286 A | 3/1999 | Sherman et al. | 606/61 |
| 5,891,145 A | 4/1999 | Morrison et al. | 606/61 |
| 5,899,904 A | 5/1999 | Errico et al. | 606/61 |
| RE36,221 E | 6/1999 | Breard et al. | 606/61 |
| 5,910,142 A | 6/1999 | Tatar | 606/61 |
| 5,925,047 A | 7/1999 | Errico et al. | 606/61 |
| 5,928,231 A | 7/1999 | Klein et al. | 606/60 |
| 5,928,232 A | 7/1999 | Howland et al. | 606/61 |
| 5,928,233 A | 7/1999 | Apfelbaum et al. | 606/61 |
| 5,947,965 A | 9/1999 | Bryan | 606/61 |
| 5,947,969 A | 9/1999 | Errico et al. | 606/61 |
| 5,954,725 A | 9/1999 | Sherman et al. | 606/78 |
| 5,961,517 A | 10/1999 | Biedermann et al. | 606/61 |
| 5,964,760 A | 10/1999 | Richelsoph | 606/61 |
| 5,980,521 A | 11/1999 | Montague et al. | 606/61 |
| 5,980,523 A | 11/1999 | Jackson | 606/61 |
| 5,984,922 A | 11/1999 | McKay | 606/61 |
| 5,989,251 A | 11/1999 | Nichols | 606/61 |
| 5,989,254 A | 11/1999 | Katz | 606/73 |
| 6,001,098 A | 12/1999 | Metz-Stavenhagen et al. | 606/61 |
| 6,004,322 A | 12/1999 | Bernstein | 606/61 |
| 6,010,503 A | 1/2000 | Richelsoph et al. | 606/61 |
| 6,015,409 A | 1/2000 | Jackson | 606/61 |
| 6,033,410 A | 3/2000 | McLean et al. | |
| 6,036,693 A | 3/2000 | Yuan et al. | 606/61 |
| 6,050,997 A | 4/2000 | Mullane | 606/61 |
| 6,053,917 A | 4/2000 | Sherman et al. | 606/61 |
| 6,063,089 A | 5/2000 | Errico et al. | 606/61 |
| 6,077,262 A | 6/2000 | Schläpfer et al. | 606/61 |
| 6,086,588 A | 7/2000 | Ameil et al. | 606/61 |
| 6,090,111 A | 7/2000 | Nichols | 606/61 |
| 6,096,039 A | 8/2000 | Stoltenberg et al. | 606/61 |
| 6,113,600 A | 9/2000 | Drummond et al. | 606/61 |
| 6,113,601 A | 9/2000 | Tatar | 606/61 |
| 6,123,706 A * | 9/2000 | Lange | 606/264 |
| 6,127,597 A | 10/2000 | Beyar et al. | 623/16 |
| 6,132,430 A | 10/2000 | Wagner | 606/61 |
| 6,132,434 A | 10/2000 | Sherman et al. | 606/78 |
| 6,132,464 A | 10/2000 | Martin | |
| 6,136,000 A | 10/2000 | Louis et al. | 606/61 |
| 6,146,383 A | 11/2000 | Studer et al. | 606/61 |
| 6,171,311 B1 | 1/2001 | Richelsoph | 606/61 |
| 6,193,720 B1 | 2/2001 | Yuan et al. | 606/61 |
| 6,197,028 B1 | 3/2001 | Ray et al. | 606/61 |
| 6,210,413 B1 | 4/2001 | Justis et al. | 606/61 |
| 6,217,578 B1 | 4/2001 | Crozet et al. | 606/61 |
| 6,248,106 B1 | 6/2001 | Ferree | 606/61 |
| 6,254,602 B1 | 7/2001 | Justis | 606/61 |
| 6,261,287 B1 | 7/2001 | Metz-Stavenhagen | 606/61 |
| 6,267,765 B1 | 7/2001 | Taylor et al. | |
| 6,273,888 B1 | 8/2001 | Justis | 606/61 |
| 6,273,914 B1 | 8/2001 | Papas | 623/17.11 |
| 6,280,442 B1 | 8/2001 | Barker et al. | |
| 6,280,443 B1 | 8/2001 | Gu et al. | 606/61 |
| 6,287,311 B1 | 9/2001 | Sherman et al. | 606/78 |
| 6,293,949 B1 | 9/2001 | Justis et al. | 606/61 |
| 6,302,882 B1 | 10/2001 | Lin et al. | |
| 6,302,888 B1 | 10/2001 | Mellinger et al. | 606/73 |
| 6,309,391 B1 | 10/2001 | Crandall et al. | 606/61 |
| 6,325,802 B1 | 12/2001 | Frigg | 606/61 |
| 6,328,740 B1 | 12/2001 | Richelsoph | 606/61 |
| 6,344,057 B1 | 2/2002 | Rabbe et al. | 623/17 |
| 6,355,040 B1 | 3/2002 | Richelsoph et al. | 606/61 |
| 6,379,354 B1 | 4/2002 | Rogozinski | 606/61 |
| 6,402,749 B1 | 6/2002 | Ashman | 606/61 |
| 6,402,751 B1 | 6/2002 | Hoeck et al. | 606/61 |
| 6,402,752 B2 | 6/2002 | Schäffler-Wachter et al. | 606/61 |
| 6,413,257 B1 | 7/2002 | Lin et al. | 606/61 |
| 6,416,515 B1 | 7/2002 | Wagner | 606/61 |
| 6,423,064 B1 | 7/2002 | Kluger | 606/61 |
| 6,440,169 B1 | 8/2002 | Elberg et al. | 623/17.16 |
| 6,451,021 B1 | 9/2002 | Ralph et al. | 606/61 |
| 6,454,773 B1 | 9/2002 | Sherman et al. | 606/78 |
| 6,458,131 B1 | 10/2002 | Ray | 606/61 |
| 6,458,132 B2 | 10/2002 | Choi | 606/61 |
| 6,468,276 B1 | 10/2002 | McKay | 606/61 |
| 6,471,705 B1 | 10/2002 | Biedermann et al. | 606/61 |
| 6,475,219 B1 | 11/2002 | Shelokov | |
| 6,478,797 B1 | 11/2002 | Paul | 606/61 |
| 6,482,207 B1 | 11/2002 | Errico | 606/61 |
| 6,485,491 B1 | 11/2002 | Farris et al. | 606/61 |
| 6,488,681 B2 | 12/2002 | Martin et al. | 606/61 |
| 6,520,962 B1 | 2/2003 | Taylor et al. | 606/61 |
| 6,520,990 B1 | 2/2003 | Ray | 623/17.11 |
| 6,537,276 B2 | 3/2003 | Metz-Stavenhagen | 606/61 |
| 6,540,748 B2 | 4/2003 | Lombardo | 606/61 |
| 6,540,749 B2 | 4/2003 | Schäfer et al. | 606/61 |
| 6,547,789 B1 | 4/2003 | Ventre et al. | 606/61 |
| 6,554,831 B1 | 4/2003 | Rivard et al. | |
| 6,554,832 B2 | 4/2003 | Shluzas | 606/61 |
| 6,554,834 B1 | 4/2003 | Crozet et al. | 606/65 |
| 6,565,565 B1 | 5/2003 | Yuan et al. | 606/61 |
| 6,565,566 B1 | 5/2003 | Wagner et al. | 606/61 |
| 6,565,567 B1 | 5/2003 | Haider | 606/61 |
| 6,565,605 B2 | 5/2003 | Goble et al. | 623/17.11 |
| 6,572,617 B1 | 6/2003 | Senegas | 606/61 |
| 6,572,653 B1 | 6/2003 | Simonson | 623/17.13 |
| 6,579,290 B1 | 6/2003 | Hardcastle et al. | 606/61 |
| 6,585,737 B1 | 7/2003 | Baccelli et al. | 606/61 |
| 6,589,243 B1 | 7/2003 | Viart et al. | |
| 6,616,669 B2 | 9/2003 | Ogilvie et al. | 606/61 |
| 6,623,485 B2 | 9/2003 | Doubler et al. | 606/61 |
| 6,626,905 B1 | 9/2003 | Schmiel et al. | 606/61 |
| 6,626,908 B2 | 9/2003 | Cooper et al. | 606/61 |
| 6,645,207 B2 | 11/2003 | Dixon et al. | 606/61 |
| 6,652,526 B1 | 11/2003 | Arafiles | 606/61 |
| 6,656,181 B2 | 12/2003 | Dixon et al. | 606/69 |
| 6,660,004 B2 | 12/2003 | Barker et al. | 606/61 |
| 6,660,005 B2 | 12/2003 | Toyama et al. | 606/61 |
| 6,676,661 B1 | 1/2004 | Antonio et al. | |
| 6,695,845 B2 | 2/2004 | Dixon et al. | 606/70 |
| 6,706,045 B2 | 3/2004 | Lin et al. | 606/61 |
| 6,709,434 B1 | 3/2004 | Gournay et al. | 606/61 |
| 6,716,213 B2 | 4/2004 | Shitoto | 606/61 |
| 6,716,214 B1 | 4/2004 | Jackson | 606/61 |
| 6,726,689 B2 | 4/2004 | Jackson | 606/73 |
| 6,736,820 B2 | 5/2004 | Biedermann et al. | 606/73 |
| 6,740,086 B2 | 5/2004 | Richelsoph | |
| 6,749,614 B2 | 6/2004 | Teitelbaum et al. | 606/61 |
| 6,752,807 B2 | 6/2004 | Lin et al. | 606/61 |
| 6,755,829 B1 | 6/2004 | Bono et al. | 606/61 |
| 6,755,835 B2 | 6/2004 | Schultheiss et al. | 606/73 |
| 6,761,719 B2 | 7/2004 | Justis et al. | 606/61 |
| 6,783,526 B1 | 8/2004 | Lin et al. | 606/61 |
| 6,783,527 B2 | 8/2004 | Drewry et al. | 606/61 |
| 6,786,907 B2 | 9/2004 | Lange | 606/61 |
| 6,793,656 B1 | 9/2004 | Mathews | 606/61 |
| 6,805,695 B2 | 10/2004 | Keith et al. | 606/61 |
| 6,805,714 B2 | 10/2004 | Sutcliffe | 623/17.11 |
| 6,811,567 B2 | 11/2004 | Reiley | 623/17.11 |
| 6,827,743 B2 | 12/2004 | Eisermann et al. | |
| 6,832,999 B2 | 12/2004 | Ueyama et al. | 606/61 |
| 6,840,940 B2 | 1/2005 | Ralph et al. | 606/61 |
| 6,843,791 B2 | 1/2005 | Serhan | 606/61 |
| 6,852,128 B2 | 2/2005 | Lange | 623/17.11 |
| 6,858,029 B2 | 2/2005 | Yeh | |
| 6,858,030 B2 | 2/2005 | Martin et al. | 606/61 |
| 6,869,433 B2 | 3/2005 | Glascott | 606/73 |
| 6,875,211 B2 | 4/2005 | Nichols et al. | 606/61 |
| 6,881,215 B2 | 4/2005 | Assaker et al. | 606/61 |
| 6,883,520 B2 | 4/2005 | Lambrecht | 128/898 |
| 6,887,242 B2 | 5/2005 | Doubler et al. | 606/61 |
| 6,899,714 B2 | 5/2005 | Vaughan | 606/61 |
| 6,918,911 B2 | 7/2005 | Biedermann et al. | 606/61 |
| 6,932,817 B2 | 8/2005 | Baynham et al. | 606/61 |
| 6,945,974 B2 | 9/2005 | Dalton | 606/70 |
| 6,951,561 B2 | 10/2005 | Warren et al. | 606/73 |
| 6,964,666 B2 | 11/2005 | Jackson | 606/61 |
| 6,966,910 B2 | 11/2005 | Ritland | 606/61 |
| 6,986,771 B2 | 1/2006 | Paul et al. | 606/61 |
| 6,991,632 B2 | 1/2006 | Ritland | 606/61 |
| 7,008,423 B2 | 3/2006 | Assaker et al. | 606/61 |
| 7,011,685 B2 | 3/2006 | Arnin et al. | 623/17.16 |

| Patent No. | Date | Inventor(s) | Class |
|---|---|---|---|
| 7,018,378 B2 | 3/2006 | Biedermann et al. | 606/61 |
| 7,018,379 B2 | 3/2006 | Drewry | 606/61 |
| 7,022,122 B2 | 4/2006 | Amrein et al. | 606/61 |
| 7,029,475 B2 | 4/2006 | Panjabi | 606/61 |
| 7,033,392 B2 | 4/2006 | Schmiel | |
| 7,048,736 B2 | 5/2006 | Robinson et al. | 606/61 |
| 7,051,451 B2 | 5/2006 | Augostino et al. | 33/512 |
| 7,060,066 B2 | 6/2006 | Zhao et al. | 606/61 |
| 7,074,237 B2 | 7/2006 | Goble et al. | 623/17.11 |
| 7,081,117 B2 | 7/2006 | Bono et al. | 606/61 |
| 7,083,621 B2 | 8/2006 | Shaolian et al. | 606/61 |
| 7,083,622 B2 | 8/2006 | Simonson | 606/61 |
| 7,087,056 B2 | 8/2006 | Vaughan | 606/61 |
| 7,087,057 B2 | 8/2006 | Konieczynski et al. | 606/73 |
| 7,087,084 B2 | 8/2006 | Reiley | 623/17.11 |
| 7,090,698 B2 | 8/2006 | Goble et al. | 623/17.11 |
| 7,101,398 B2 | 9/2006 | Dooris et al. | 623/13.11 |
| 7,104,991 B2 | 9/2006 | Dixon | |
| 7,104,992 B2 | 9/2006 | Bailey | 606/61 |
| 7,107,091 B2 | 9/2006 | Jutras et al. | 600/429 |
| 7,125,410 B2 | 10/2006 | Freudiger | 606/61 |
| 7,125,426 B2 | 10/2006 | Moumene et al. | 623/23.42 |
| 7,137,985 B2 | 11/2006 | Jahng | |
| 7,163,538 B2 | 1/2007 | Altarac et al. | |
| 7,189,235 B2 | 3/2007 | Cauthen | |
| 7,214,227 B2 | 5/2007 | Colleran et al. | 606/61 |
| 7,250,052 B2 | 7/2007 | Landry et al. | 606/61 |
| 7,270,665 B2 | 9/2007 | Matthew et al. | |
| 7,282,064 B2 | 10/2007 | Chin | 623/17.15 |
| 7,294,128 B2 | 11/2007 | Alleyne et al. | |
| 7,294,129 B2 | 11/2007 | Hawkins et al. | 606/61 |
| 7,306,603 B2 | 12/2007 | Boehm, Jr. et al. | 606/61 |
| 7,306,606 B2 | 12/2007 | Sasing | 606/61 |
| 7,309,355 B2 | 12/2007 | Donnelly et al. | |
| 7,326,210 B2 | 2/2008 | Jahng et al. | 606/61 |
| 7,335,201 B2 | 2/2008 | Doubler et al. | 606/61 |
| 7,338,490 B2 | 3/2008 | Ogilvie et al. | |
| 7,338,491 B2 | 3/2008 | Baker et al. | |
| 7,344,539 B2 | 3/2008 | Serhan et al. | |
| 7,361,196 B2 | 4/2008 | Fallin et al. | |
| 7,377,923 B2 | 5/2008 | Purcell et al. | |
| 7,445,627 B2 | 11/2008 | Hawkes et al. | |
| 7,455,684 B2 | 11/2008 | Gradel et al. | |
| 7,476,238 B2 | 1/2009 | Panjabi | |
| 7,479,156 B2 | 1/2009 | Lourdel et al. | |
| 7,481,828 B2 | 1/2009 | Mazda et al. | |
| 7,491,218 B2 | 2/2009 | Landry et al. | |
| 7,503,924 B2 | 3/2009 | Lee et al. | |
| 7,513,905 B2 | 4/2009 | Jackson | |
| 7,513,911 B2 | 4/2009 | Lambrecht et al. | |
| 7,520,879 B2 | 4/2009 | Justis | |
| 7,530,992 B2 | 5/2009 | Biedermann et al. | |
| 7,533,672 B2 | 5/2009 | Morgan et al. | |
| 7,553,320 B2 | 6/2009 | Molz, IV et al. | |
| 7,553,329 B2 | 6/2009 | Lambrecht et al. | |
| 7,559,943 B2 | 7/2009 | Mujwid | |
| 7,563,274 B2 | 7/2009 | Justis et al. | |
| 7,572,279 B2 | 8/2009 | Jackson | |
| 7,578,833 B2 | 8/2009 | Bray | |
| 7,585,312 B2 | 9/2009 | Rawlins et al. | |
| 7,588,575 B2 | 9/2009 | Colleran et al. | |
| 7,588,588 B2 | 9/2009 | Spitler et al. | |
| 7,594,924 B2 | 9/2009 | Albert et al. | |
| 7,597,707 B2 | 10/2009 | Freudiger | |
| 7,601,166 B2 | 10/2009 | Biedermann et al. | |
| 7,608,095 B2 | 10/2009 | Yuan et al. | |
| 7,611,526 B2 | 11/2009 | Carl et al. | |
| 7,615,068 B2 | 11/2009 | Timm et al. | |
| 7,625,394 B2 | 12/2009 | Molz, IV et al. | |
| 7,625,396 B2 | 12/2009 | Jackson | |
| 7,635,379 B2 | 12/2009 | Callahan et al. | |
| 7,648,520 B2 | 1/2010 | Markworth | |
| 7,648,522 B2 | 1/2010 | David | |
| 7,662,172 B2 | 2/2010 | Warnick | |
| 7,662,173 B2 | 2/2010 | Cragg et al. | |
| 7,662,175 B2 | 2/2010 | Jackson | |
| 7,674,293 B2 | 3/2010 | Kuiper et al. | |
| 7,678,136 B2 * | 3/2010 | Doubler et al. | 606/246 |
| 7,678,137 B2 | 3/2010 | Butler et al. | |
| 7,682,377 B2 | 3/2010 | Konieczynski et al. | |
| 7,691,129 B2 | 4/2010 | Felix | |
| 7,691,132 B2 | 4/2010 | Landry et al. | |
| 7,699,873 B2 | 4/2010 | Stevenson et al. | |
| 7,699,875 B2 | 4/2010 | Timm et al. | |
| 7,704,270 B2 | 4/2010 | De Coninck | |
| 7,708,762 B2 | 5/2010 | McCarthy et al. | |
| 7,713,287 B2 | 5/2010 | Timm et al. | |
| 7,713,288 B2 | 5/2010 | Timm et al. | |
| 7,717,939 B2 | 5/2010 | Ludwig et al. | |
| 7,722,646 B2 | 5/2010 | Ralph et al. | |
| 7,722,649 B2 | 5/2010 | Biedermann et al. | |
| 7,722,654 B2 | 5/2010 | Taylor et al. | |
| 7,727,259 B2 | 6/2010 | Park | |
| 7,727,261 B2 | 6/2010 | Barker et al. | |
| 7,731,734 B2 | 6/2010 | Clement et al. | |
| 7,731,736 B2 | 6/2010 | Guenther et al. | |
| 7,763,051 B2 | 7/2010 | Labrom et al. | |
| 7,763,052 B2 | 7/2010 | Jahng | |
| 7,766,944 B2 | 8/2010 | Metz-Stavenhagen | |
| 7,766,945 B2 | 8/2010 | Nilsson et al. | |
| 7,776,071 B2 | 8/2010 | Fortin et al. | |
| 7,785,350 B2 | 8/2010 | Eckhardt et al. | |
| 7,785,354 B2 | 8/2010 | Biedermann et al. | |
| 7,789,896 B2 | 9/2010 | Jackson | |
| 7,794,477 B2 | 9/2010 | Melkent et al. | |
| 7,794,481 B2 | 9/2010 | Molz, IV et al. | |
| 7,799,060 B2 | 9/2010 | Lange et al. | |
| 7,803,189 B2 | 9/2010 | Koske | |
| 7,806,913 B2 | 10/2010 | Fanger et al. | |
| 7,806,914 B2 | 10/2010 | Boyd et al. | |
| 7,811,288 B2 | 10/2010 | Jones et al. | |
| 7,811,309 B2 | 10/2010 | Timm et al. | |
| 7,811,311 B2 | 10/2010 | Markworth et al. | |
| 7,815,664 B2 | 10/2010 | Sherman et al. | |
| 7,815,665 B2 | 10/2010 | Jahng et al. | |
| 7,819,899 B2 | 10/2010 | Lancial | |
| 7,819,901 B2 | 10/2010 | Yuan et al. | |
| 7,819,902 B2 | 10/2010 | Abdelgany et al. | |
| 7,828,824 B2 | 11/2010 | Kwak et al. | |
| 7,828,825 B2 | 11/2010 | Bruneau et al. | |
| 7,828,826 B2 | 11/2010 | Drewry et al. | |
| 7,828,830 B2 | 11/2010 | Thramann et al. | |
| 7,833,250 B2 | 11/2010 | Jackson | |
| 7,833,256 B2 | 11/2010 | Biedermann et al. | |
| 7,842,072 B2 | 11/2010 | Dawson | |
| 7,850,715 B2 | 12/2010 | Bonouskou et al. | |
| 7,850,718 B2 * | 12/2010 | Bette et al. | 606/267 |
| 7,854,752 B2 | 12/2010 | Colleran et al. | |
| 7,857,833 B2 | 12/2010 | Abdou | |
| 7,857,834 B2 | 12/2010 | Boschert | |
| 7,862,586 B2 | 1/2011 | Malek | |
| 7,862,587 B2 | 1/2011 | Jackson | |
| 7,862,588 B2 | 1/2011 | Abdou | |
| 7,862,591 B2 | 1/2011 | Dewey et al. | |
| 7,862,594 B2 | 1/2011 | Abdelgany et al. | |
| 7,871,413 B2 | 1/2011 | Park et al. | |
| 7,875,059 B2 | 1/2011 | Patterson et al. | |
| 7,875,060 B2 | 1/2011 | Chin | |
| 7,879,074 B2 | 2/2011 | Kwak et al. | |
| 7,892,266 B2 | 2/2011 | Carli | |
| 7,909,856 B2 | 3/2011 | Yuan et al. | |
| 7,914,558 B2 | 3/2011 | Landry et al. | |
| 7,918,792 B2 | 4/2011 | Drzyzga et al. | |
| 7,927,359 B2 * | 4/2011 | Trautwein et al. | 606/264 |
| 2003/0004511 A1 | 1/2003 | Ferree | |
| 2003/0171749 A1 | 9/2003 | Le Couedic et al. | |
| 2004/0015166 A1 | 1/2004 | Gorek | |
| 2004/0034374 A1 | 2/2004 | Zatzsch et al. | |
| 2004/0049285 A1 | 3/2004 | Haas | |
| 2004/0097925 A1 | 5/2004 | Boehm, Jr. et al. | |
| 2004/0111088 A1 | 6/2004 | Picetti et al. | |
| 2004/0122425 A1 | 6/2004 | Suzuki et al. | |
| 2004/0147928 A1 | 7/2004 | Landry et al. | |
| 2004/0153077 A1 | 8/2004 | Biedermann et al. | |
| 2004/0158247 A1 | 8/2004 | Sitiso et al. | |
| 2004/0162560 A1 | 8/2004 | Raynor et al. | |
| 2004/0172022 A1 | 9/2004 | Landry et al. | |
| 2004/0172024 A1 | 9/2004 | Gorek | |

| | | | | | | |
|---|---|---|---|---|---|---|
| 2004/0215192 A1 | 10/2004 | Justis et al. | | 2006/0264937 A1 | 11/2006 | White |
| 2004/0225289 A1 | 11/2004 | Biedermann et al. | | 2006/0276897 A1 | 12/2006 | Winslow et al. |
| 2004/0230192 A1 | 11/2004 | Graf | | 2006/0282073 A1 | 12/2006 | Simanovsky |
| 2004/0230304 A1 | 11/2004 | Yuan et al. | | 2006/0282078 A1 | 12/2006 | Labrom et al. |
| 2005/0049589 A1 | 3/2005 | Jackson | | 2007/0016190 A1 | 1/2007 | Martinez et al. |
| 2005/0080415 A1 | 4/2005 | Keyer et al. | | 2007/0016194 A1 | 1/2007 | Shaolian et al. |
| 2005/0090822 A1 | 4/2005 | DiPoto | | 2007/0016201 A1 | 1/2007 | Freudiger |
| 2005/0096652 A1 | 5/2005 | Burton | | 2007/0049936 A1 | 3/2007 | Colleran et al. |
| 2005/0107788 A1 | 5/2005 | Beaurain et al. | | 2007/0083200 A1 | 4/2007 | Gittings et al. |
| 2005/0113923 A1 | 5/2005 | Acker et al. | | 2007/0088359 A1 | 4/2007 | Woods et al. |
| 2005/0131404 A1 | 6/2005 | Mazda et al. | | 2007/0093814 A1 | 4/2007 | Callahan, II et al. |
| 2005/0131406 A1 | 6/2005 | Reiley et al. | | 2007/0093820 A1 | 4/2007 | Freudiger |
| 2005/0143737 A1 | 6/2005 | Pafford et al. | | 2007/0093821 A1 | 4/2007 | Freudiger |
| 2005/0171537 A1 | 8/2005 | Mazel et al. | | 2007/0118122 A1 | 5/2007 | Butler et al. |
| 2005/0171543 A1 | 8/2005 | Timm et al. | | 2007/0123871 A1 | 5/2007 | Jahng |
| 2005/0177156 A1 | 8/2005 | Timm et al. | | 2007/0161994 A1 | 7/2007 | Lowery et al. |
| 2005/0177157 A1 | 8/2005 | Jahng | | 2007/0162007 A1 | 7/2007 | Shoham |
| 2005/0177164 A1 | 8/2005 | Walters et al. | | 2007/0167946 A1 | 7/2007 | Triplett et al. |
| 2005/0182400 A1 | 8/2005 | White | | 2007/0167947 A1 | 7/2007 | Gittings |
| 2005/0182401 A1 | 8/2005 | Timm et al. | | 2007/0198014 A1 | 8/2007 | Graf et al. |
| 2005/0192569 A1 | 9/2005 | Nichols et al. | | 2007/0213719 A1 | 9/2007 | Hudgins et al. |
| 2005/0228382 A1 | 10/2005 | Richelsoph et al. | | 2007/0233068 A1 | 10/2007 | Bruneau et al. |
| 2005/0228385 A1 | 10/2005 | Iott et al. | | 2007/0233072 A1 | 10/2007 | Dickinson et al. |
| 2005/0240180 A1 | 10/2005 | Vienney et al. | | 2007/0233090 A1 | 10/2007 | Naifeh et al. |
| 2005/0240265 A1 | 10/2005 | Kuiper et al. | | 2007/0233091 A1 | 10/2007 | Naifeh et al. |
| 2005/0261770 A1 | 11/2005 | Kuiper et al. | | 2007/0233092 A1 | 10/2007 | Falahee |
| 2005/0267470 A1 | 12/2005 | McBride | | 2007/0233093 A1 | 10/2007 | Falahee |
| 2005/0277922 A1 | 12/2005 | Trieu et al. | | 2007/0233094 A1 | 10/2007 | Colleran et al. |
| 2005/0288670 A1 | 12/2005 | Panjabi et al. | | 2007/0250061 A1 | 10/2007 | Chin et al. |
| 2006/0025771 A1 | 2/2006 | Jackson | | 2007/0270836 A1 | 11/2007 | Bruneau et al. |
| 2006/0036324 A1 | 2/2006 | Sachs et al. | | 2007/0270838 A1 | 11/2007 | Bruneau et al. |
| 2006/0052783 A1 | 3/2006 | Dant et al. | | 2007/0276380 A1 | 11/2007 | Jahng et al. |
| 2006/0052784 A1 | 3/2006 | Dant et al. | | 2007/0288009 A1 | 12/2007 | Brown et al. |
| 2006/0052786 A1 | 3/2006 | Dant et al. | | 2007/0288012 A1 | 12/2007 | Colleran et al. |
| 2006/0058787 A1 | 3/2006 | David | | 2008/0009864 A1 | 1/2008 | Forton et al. |
| 2006/0058788 A1 | 3/2006 | Hammer et al. | | 2008/0021459 A1 | 1/2008 | Lim |
| 2006/0079894 A1 | 4/2006 | Colleran et al. | | 2008/0021461 A1 | 1/2008 | Barker et al. |
| 2006/0079896 A1 | 4/2006 | Kwak et al. | | 2008/0033433 A1 | 2/2008 | Implicito |
| 2006/0084978 A1 | 4/2006 | Mokhtar | | 2008/0039838 A1 | 2/2008 | Landry et al. |
| 2006/0084982 A1 | 4/2006 | Kim | | 2008/0051787 A1 | 2/2008 | Remington et al. |
| 2006/0084983 A1 | 4/2006 | Kim | | 2008/0065073 A1 | 3/2008 | Perriello et al. |
| 2006/0084984 A1 | 4/2006 | Kim | | 2008/0065075 A1 | 3/2008 | Dant et al. |
| 2006/0084985 A1 | 4/2006 | Kim | | 2008/0065079 A1 | 3/2008 | Bruneau et al. |
| 2006/0084987 A1 | 4/2006 | Kim | | 2008/0071273 A1 | 3/2008 | Hawkes et al. |
| 2006/0084988 A1 | 4/2006 | Kim | | 2008/0077139 A1 | 3/2008 | Landry et al. |
| 2006/0084989 A1 | 4/2006 | Dickinson et al. | | 2008/0183215 A1 | 7/2008 | Altarac et al. |
| 2006/0084990 A1 | 4/2006 | Gournay et al. | | 2008/0195208 A1 | 8/2008 | Castellvi et al. |
| 2006/0085069 A1 | 4/2006 | Kim | | 2008/0262554 A1 | 10/2008 | Klyce et al. |
| 2006/0085070 A1 | 4/2006 | Kim | | 2008/0312693 A1 | 12/2008 | Trautwein et al. |
| 2006/0089643 A1 | 4/2006 | Mujwid | | 2010/0174317 A1 | 7/2010 | Timm et al. |
| 2006/0095035 A1 | 5/2006 | Jones et al. | | 2010/0198270 A1 | 8/2010 | Barker et al. |
| 2006/0106383 A1 | 5/2006 | Biedermann et al. | | 2010/0222819 A1 | 9/2010 | Timm et al. |
| 2006/0111712 A1 | 5/2006 | Jackson | | | | |
| 2006/0122620 A1 | 6/2006 | Kim | | FOREIGN PATENT DOCUMENTS | | |
| 2006/0129148 A1 | 6/2006 | Simmons et al. | | DE | 3639810 A1 | 5/1988 |
| 2006/0129149 A1 | 6/2006 | Iott et al. | | EP | 0128058 B1 | 4/1988 |
| 2006/0142761 A1 | 6/2006 | Landry et al. | | EP | 0669109 B1 | 8/1995 |
| 2006/0149242 A1 | 7/2006 | Kraus et al. | | EP | 0982007 | 3/2000 |
| 2006/0149244 A1 | 7/2006 | Amrein et al. | | EP | 1281362 A2 | 2/2003 |
| 2006/0149380 A1 | 7/2006 | Lotz et al. | | EP | 1330987 A1 | 7/2003 |
| 2006/0161153 A1 | 7/2006 | Hawkes et al. | | FR | 2612070 A1 | 9/1988 |
| 2006/0195093 A1 | 8/2006 | Jahng | | FR | 2615095 A1 | 11/1988 |
| 2006/0200128 A1 | 9/2006 | Mueller | | FR | 2844180 A1 | 3/2004 |
| 2006/0200131 A1 | 9/2006 | Chao et al. | | FR | 2880256 B1 | 7/2006 |
| 2006/0229607 A1 | 10/2006 | Brumfield | | GB | 780652 | 8/1957 |
| 2006/0229613 A1 | 10/2006 | Timm et al. | | GB | 2173104 | 10/1986 |
| 2006/0235385 A1 | 10/2006 | Whipple | | GB | 2382304 | 5/2003 |
| 2006/0235389 A1 | 10/2006 | Albert et al. | | KR | 20080072848 | 8/2008 |
| 2006/0235392 A1 | 10/2006 | Hammer et al. | | WO | WO 87/07134 | 12/1987 |
| 2006/0235393 A1 | 10/2006 | Bono et al. | | WO | WO 94/21185 | 9/1994 |
| 2006/0241600 A1 | 10/2006 | Ensign et al. | | WO | WO 98/27884 | 7/1998 |
| 2006/0241601 A1 | 10/2006 | Trautwein et al. | | WO | WO 01/45576 | 6/2001 |
| 2006/0241603 A1 | 10/2006 | Jackson | | WO | WO 01/91656 | 12/2001 |
| 2006/0241757 A1 | 10/2006 | Anderson | | WO | WO 02/07621 | 1/2002 |
| 2006/0247623 A1 | 11/2006 | Anderson et al. | | WO | WO 02/07622 | 1/2002 |
| 2006/0247631 A1 | 11/2006 | Ahn et al. | | WO | WO 02/17803 | 3/2002 |
| 2006/0247637 A1 | 11/2006 | Colleran et al. | | WO | WO 02/39921 | 5/2002 |
| 2006/0253118 A1 | 11/2006 | Bailey | | WO | WO 02/43603 | 6/2002 |
| 2006/0264935 A1 | 11/2006 | White | | WO | WO 02/102259 | 12/2002 |

| | | |
|---|---|---|
| WO | WO 03/007828 | 1/2003 |
| WO | WO 03/009737 | 2/2003 |
| WO | WO 03/015647 | 2/2003 |
| WO | WO 03/037216 | 5/2003 |
| WO | WO 03/077806 | 9/2003 |
| WO | WO 2004/024011 | 3/2004 |
| WO | WO 2004/034916 | 4/2004 |
| WO | WO 2006/033503 | 3/2006 |
| WO | WO 2006/066685 | 6/2006 |
| WO | WO 2006/105935 | 10/2006 |
| WO | WO 2007064324 | 6/2007 |
| WO | WO 2007/080317 | 7/2007 |
| WO | WO 2008/034130 * | 3/2008 ............ 606/264 |
| WO | WO 2008/034130 | 3/2008 |
| WO | WO 2008/073544 | 6/2008 |

OTHER PUBLICATIONS

Zimmer, Inc. Website, 2007; Zimmer Spine, product description for Dynesis—The Dynamic Stabilization System, 5 pages, <http://www.zimmer com/ctl?template=IN&action=1&op=global&id=9165&pr=Y>.

Ito Medical Instrument website, 2006; ITOIKA Medical Instruments, product description for S-Plate, 15 pages, <http://ito-ika.co.jp/s-plate/splate1.pdf and http://ito-ika.co.jp/s-plate/splate1.pdf>.

"Flexible rods and the case for dynamic stabilization," Jason M. Highsmith, M.D., et al., Neurosurg. Focus, vol. 22, Jan. 2007, pp. 1-5.

"The Spinous Process: The Forgotten Appendage," Kenneth R. Kattan, M. D. et al., Skeletal Radiology, vol. 6, 1981, pp. 199-204.

"Morphological and functional changes of the lumbar spinous processes in the elderly," R. Scapinelli, Surgical Radiologic Anatomy, vol. 11, 1989, pp. 129-133.

"The Paraspinal Sacrospinalis-Splitting Approach to the Lumbar Spine," Leon L. Wiltse et al., The Journal of Bone & Joint Surgery, vol. 50-A, No. 5, Jul. 1968 pp. 919-926.

Dynamic Reconstruction of the Spine, D.H. Kim et al., Thieme, New York 2006, Chapters 1, 2, 30, 31, 37-43.

International Search Report for PCT/US07/70981 dated Apr. 23, 2008, 7 pages.

International Search Report for PCT/US/2009/058466 dated Apr. 29, 2010, 13 pages.

International Search Report for PCT/US/2009/058460 dated Apr. 29, 2010, 11 pages.

International Search Report for PCT/US/2009/058470 dated Apr. 29, 2010, 12 pages.

International Search Report for PCT/US/2009/066567 dated Jul. 20, 2010, 9 pages.

* cited by examiner

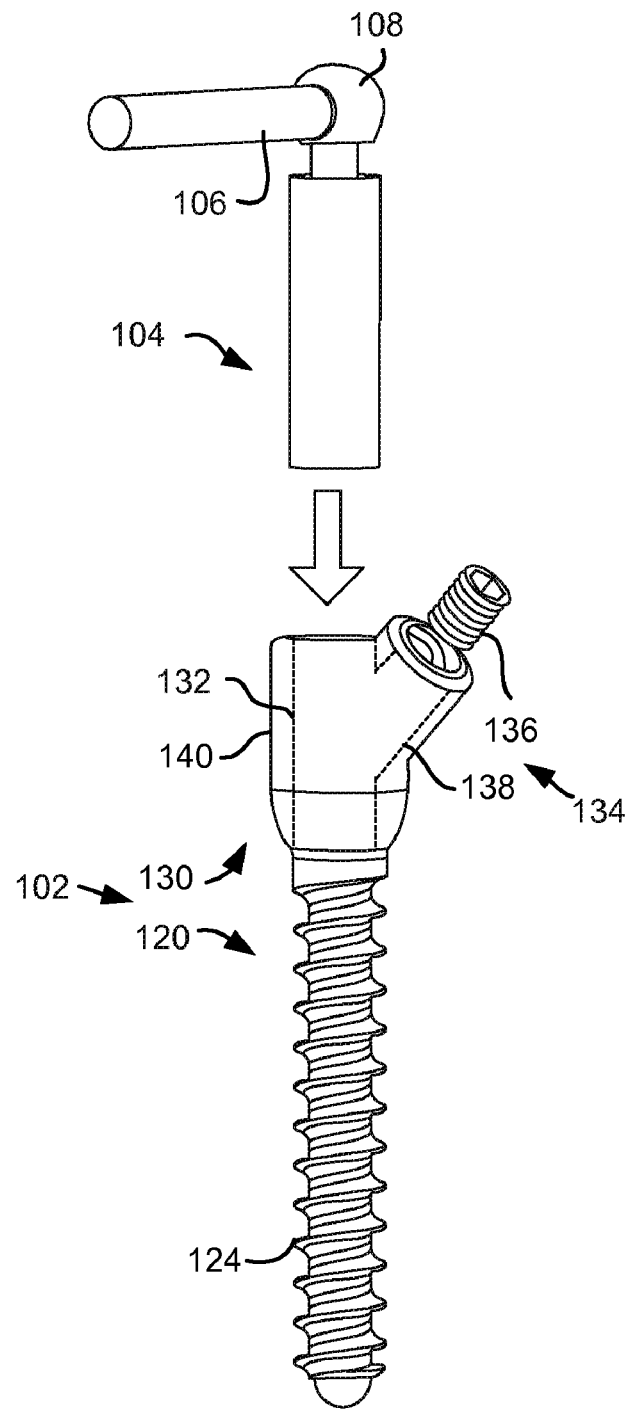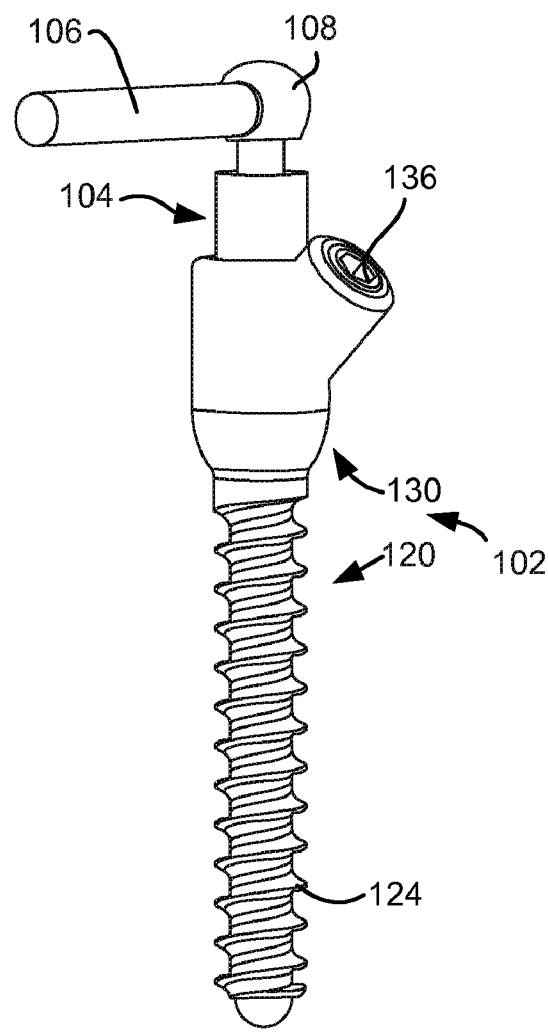
FIG. 1A  FIG. 1B

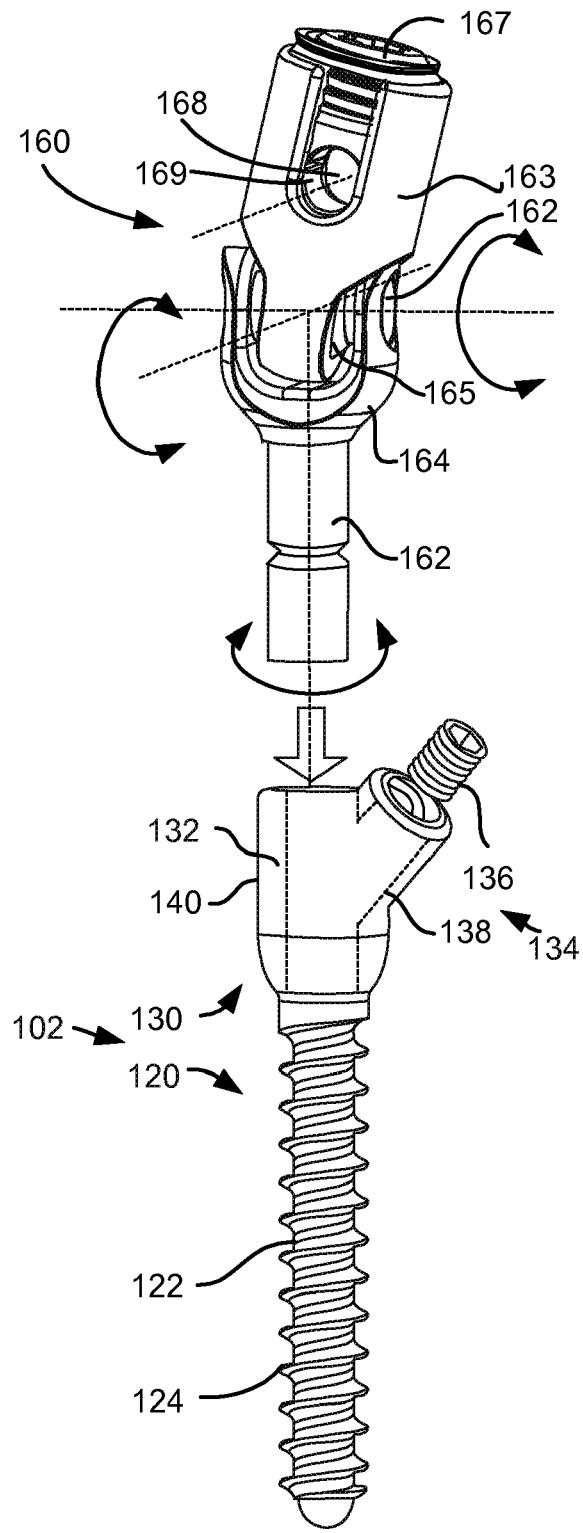
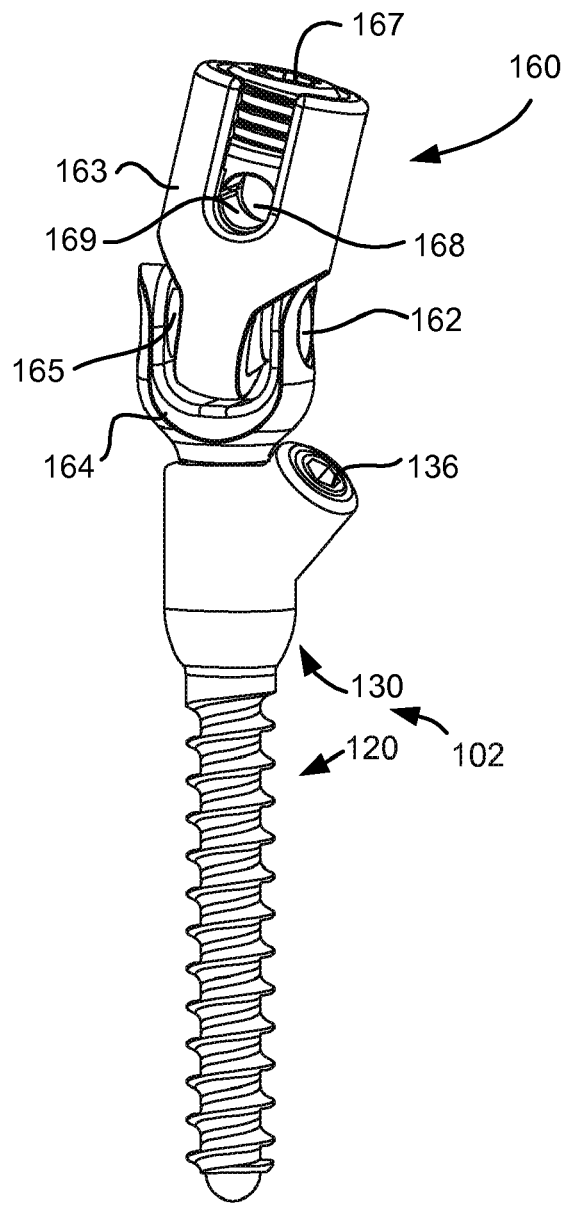
FIG. 1C  FIG. 1D

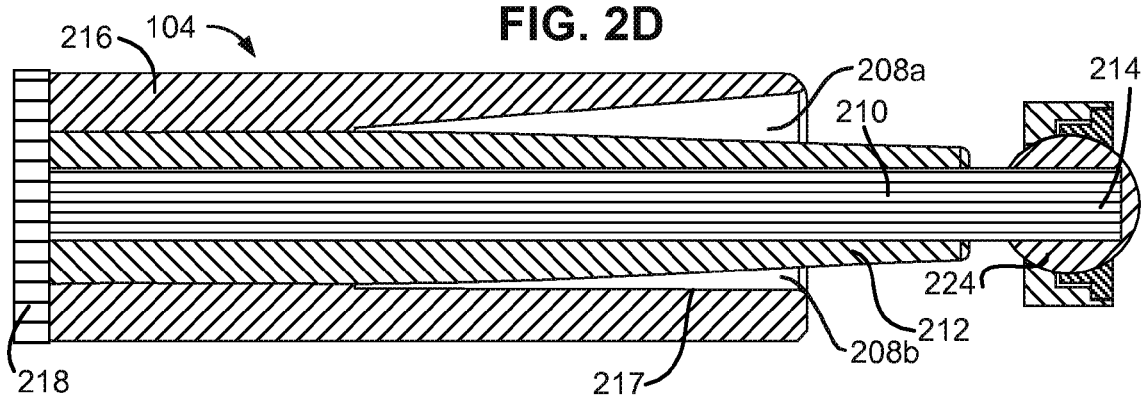
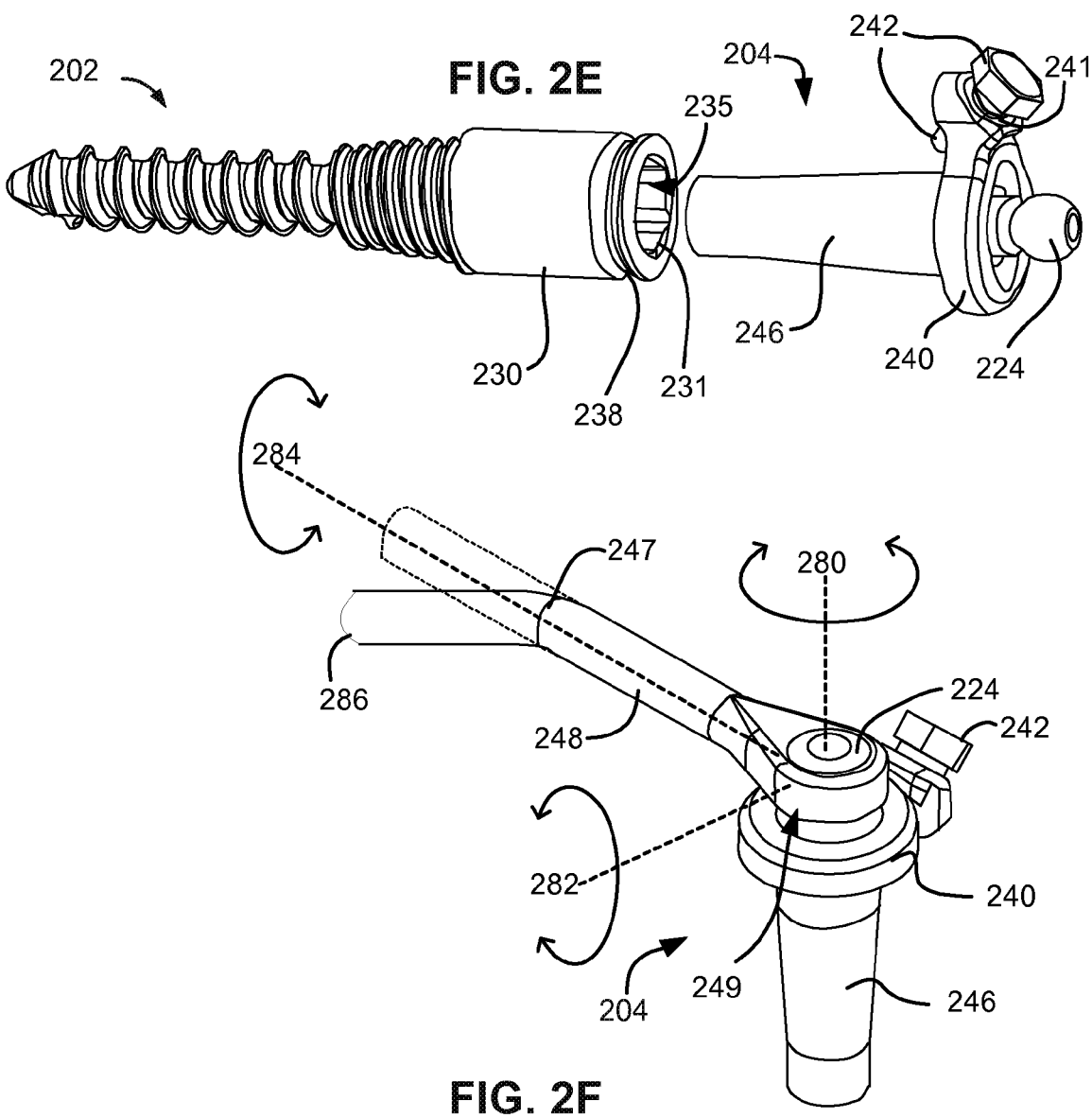

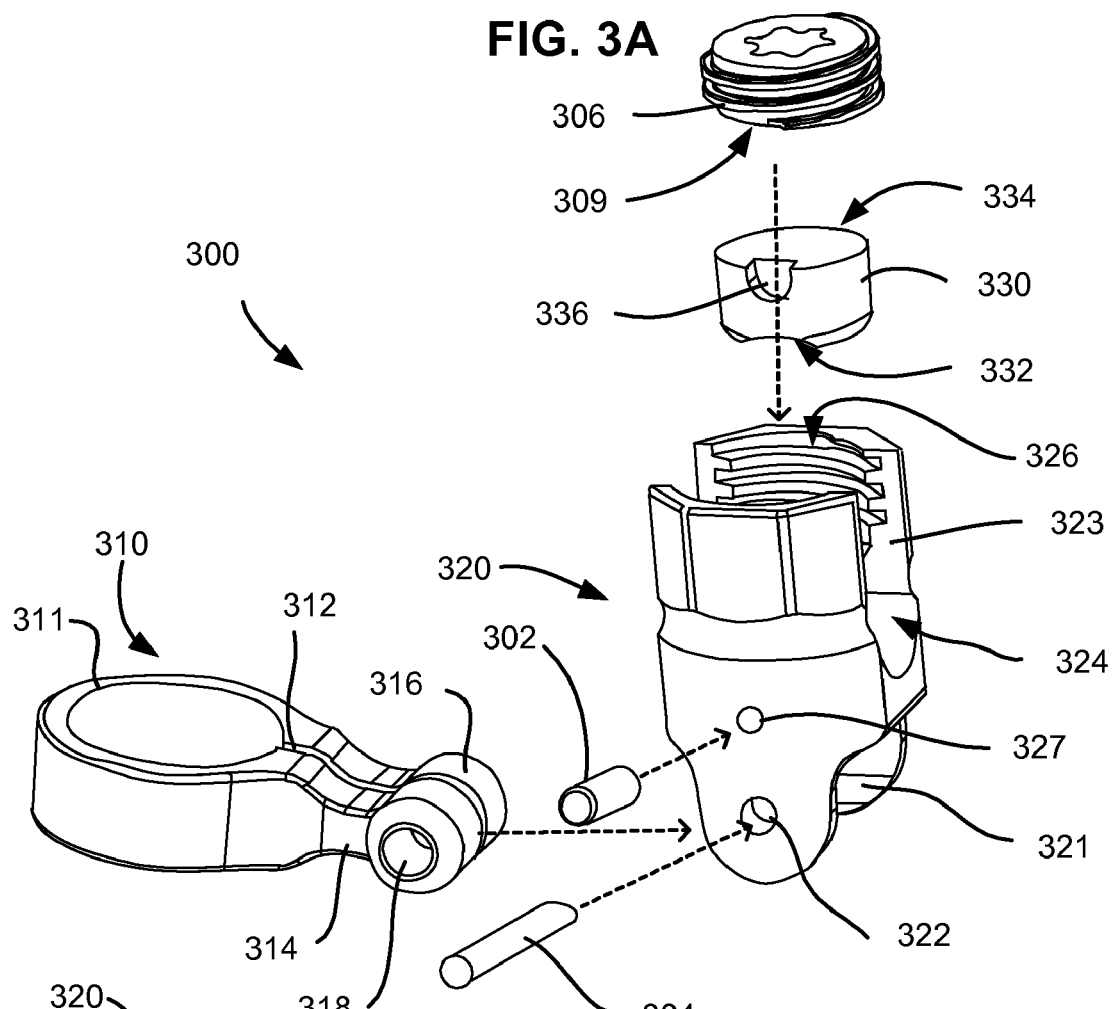
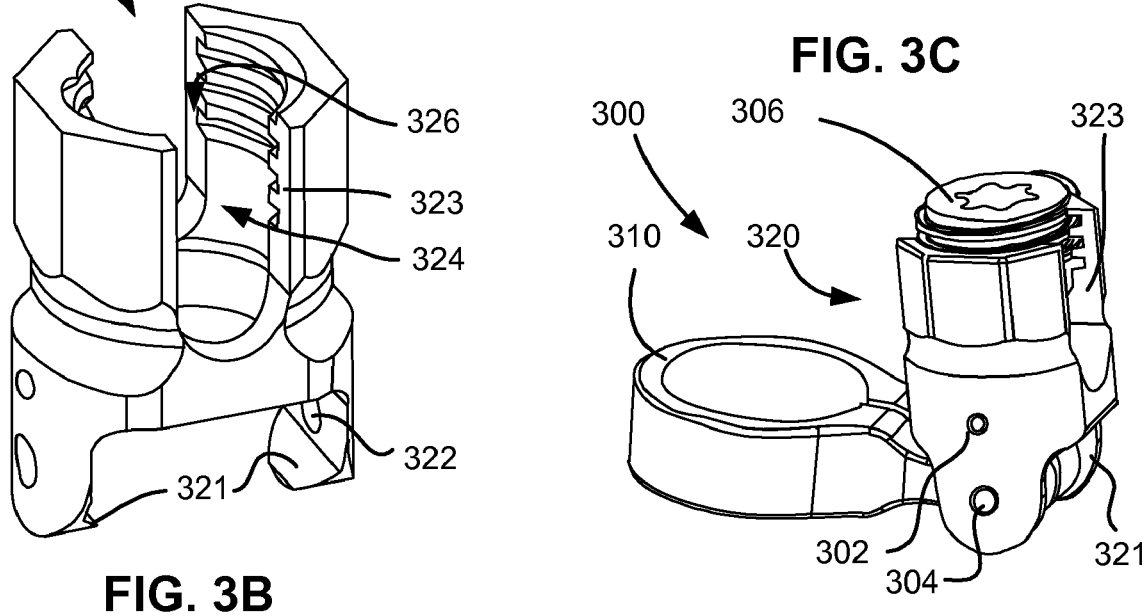

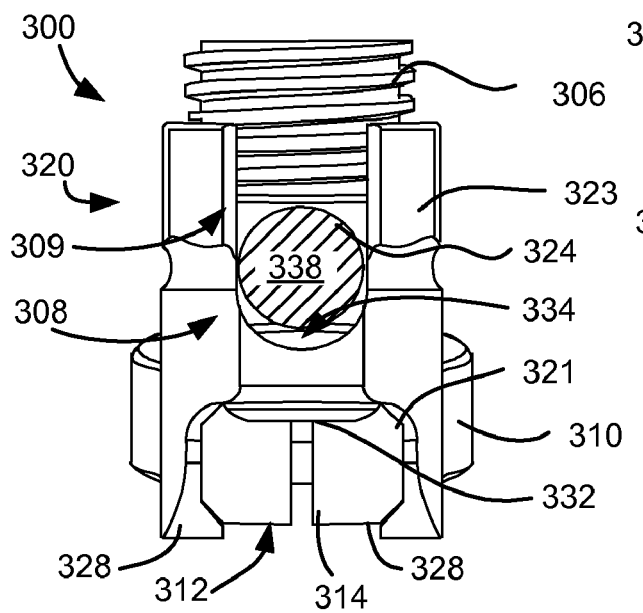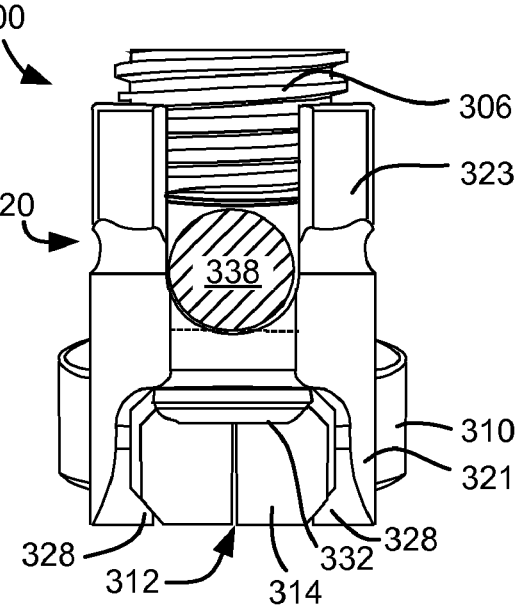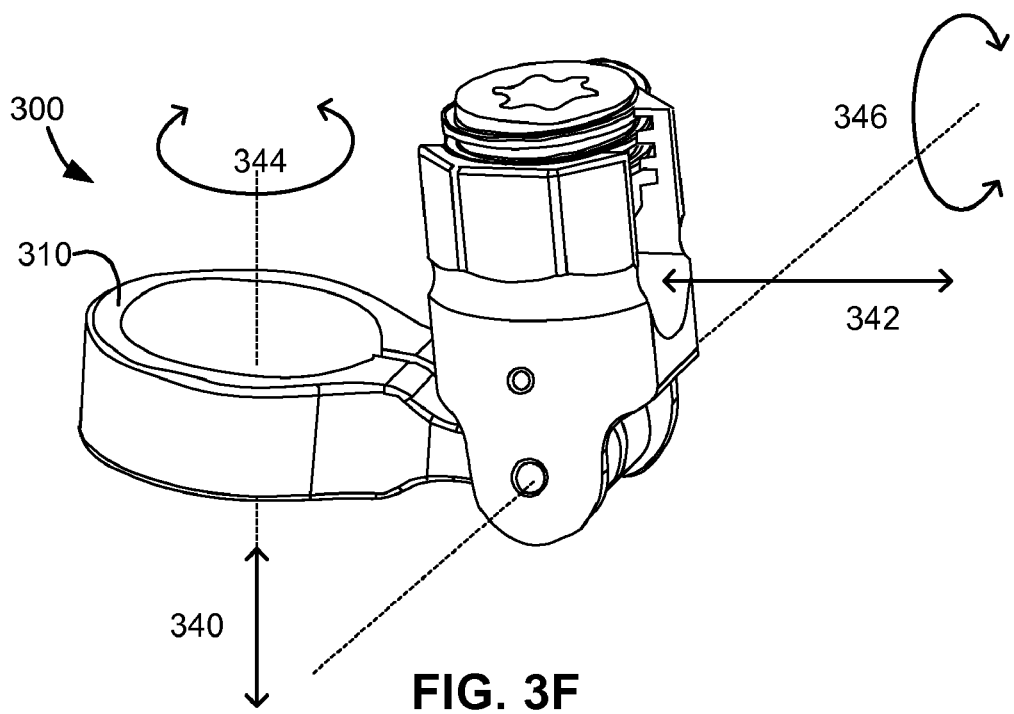

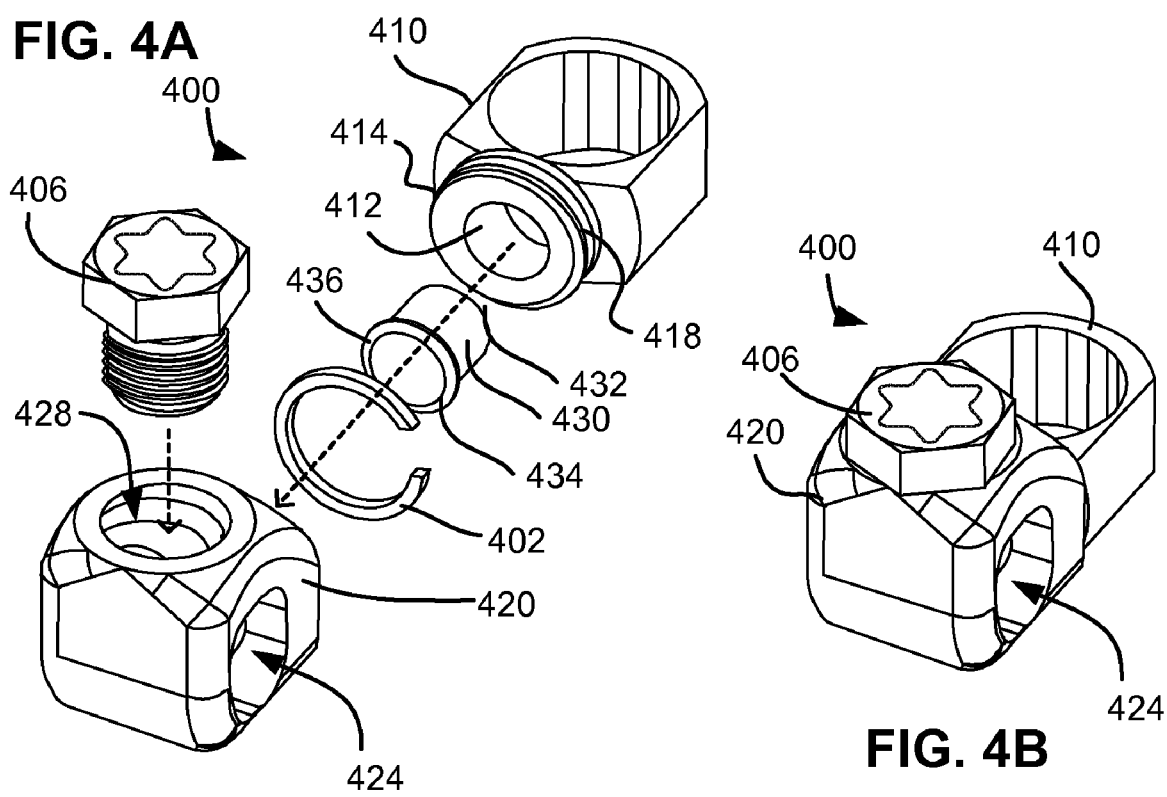
FIG. 4A
FIG. 4B
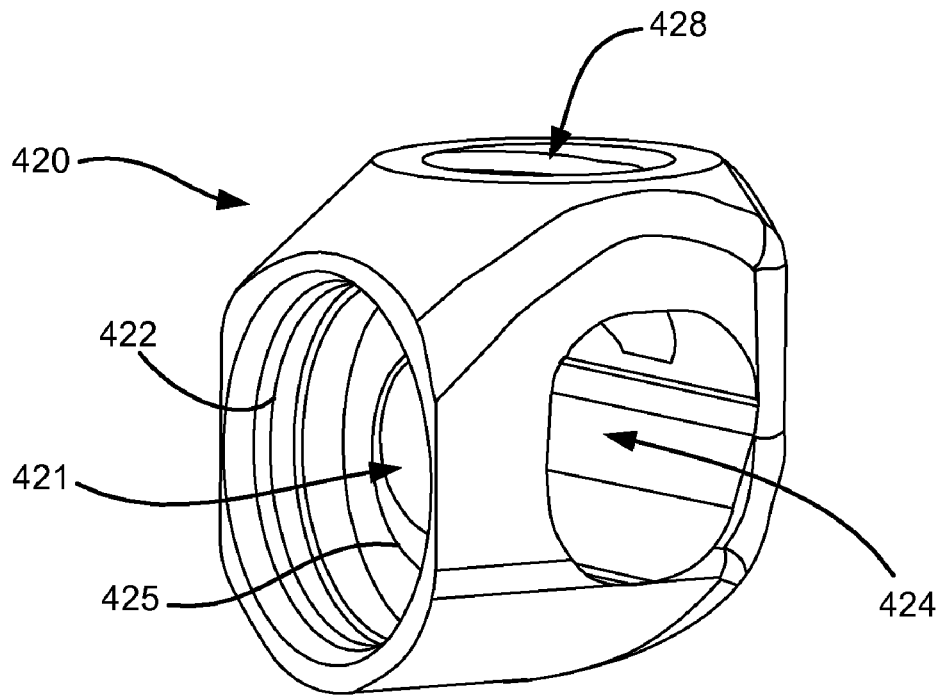
FIG. 4C

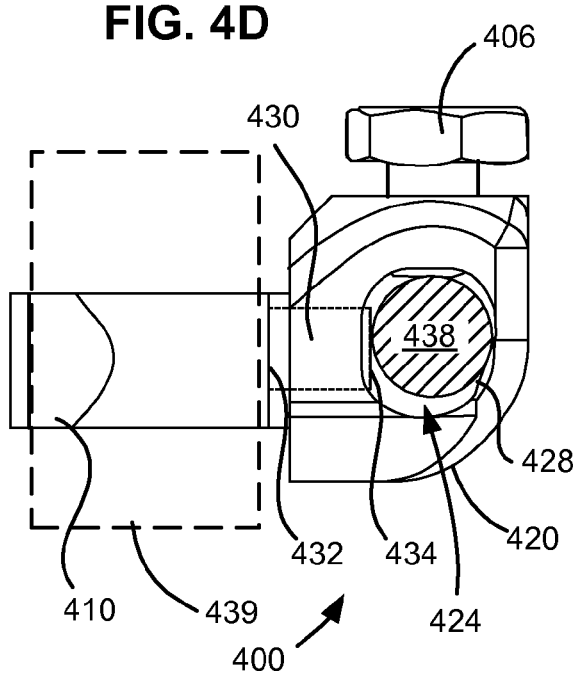
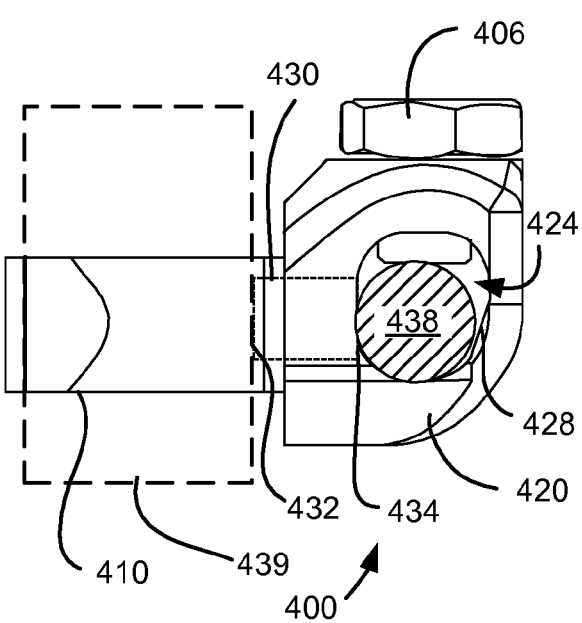
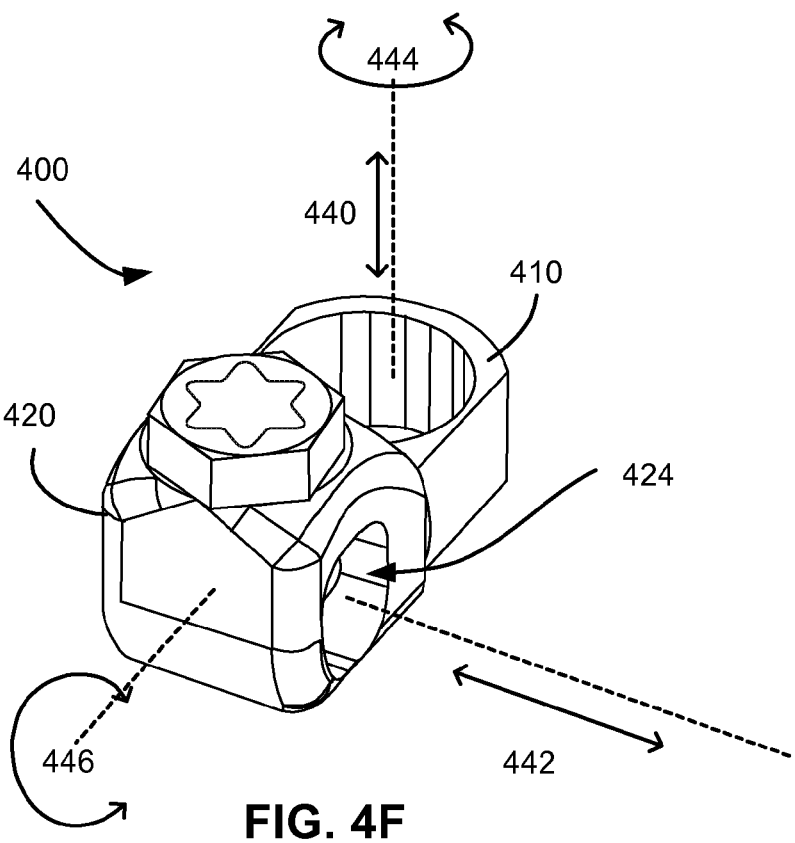
FIG. 4D
FIG. 4E
FIG. 4F

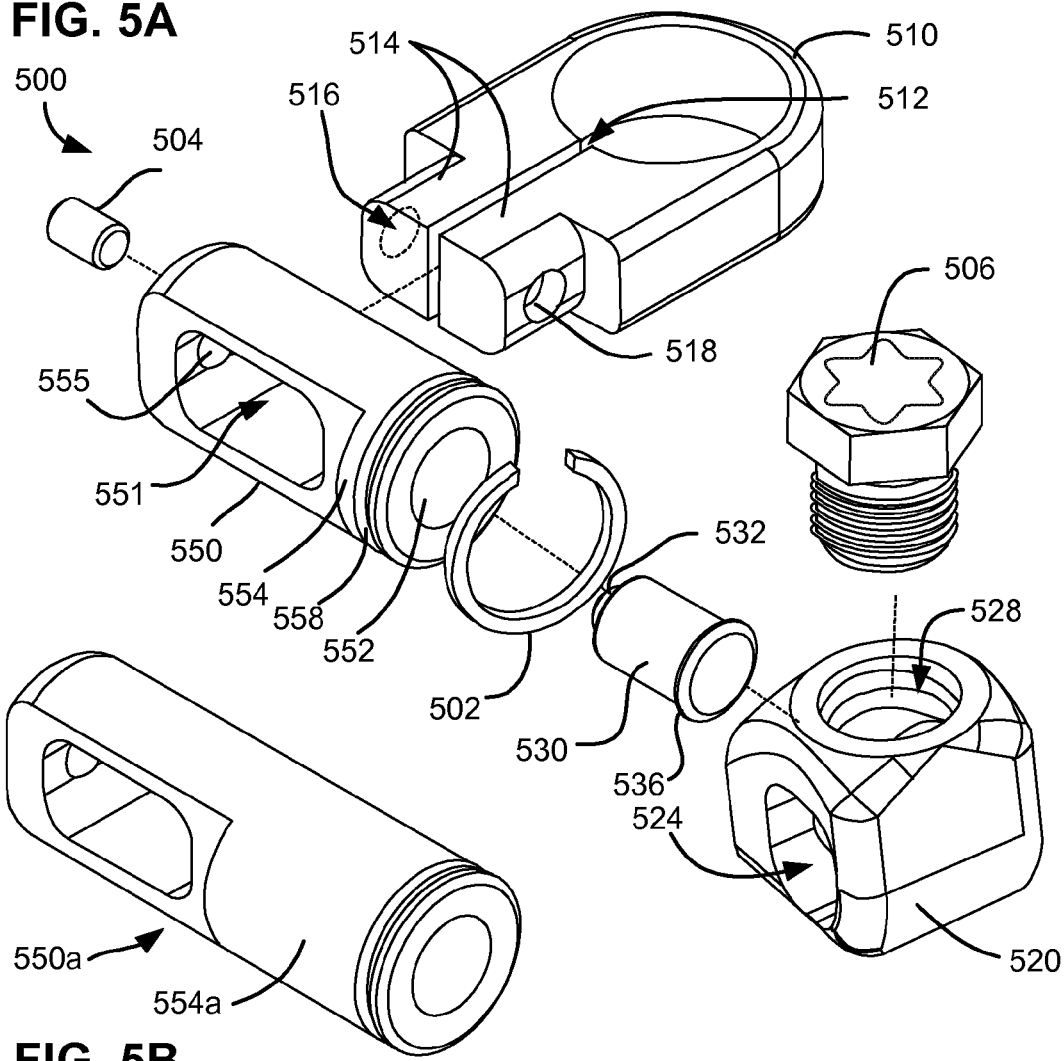
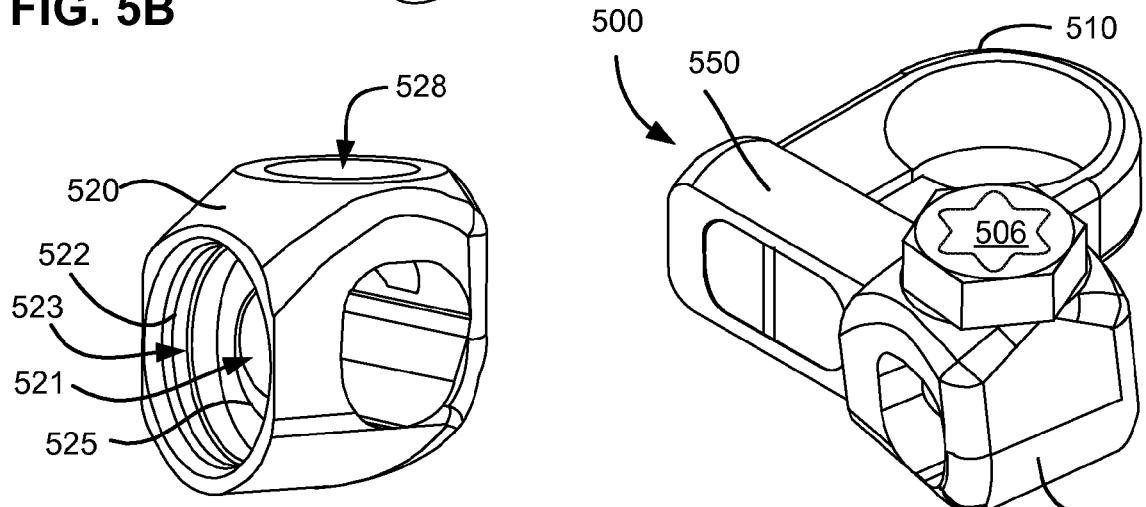

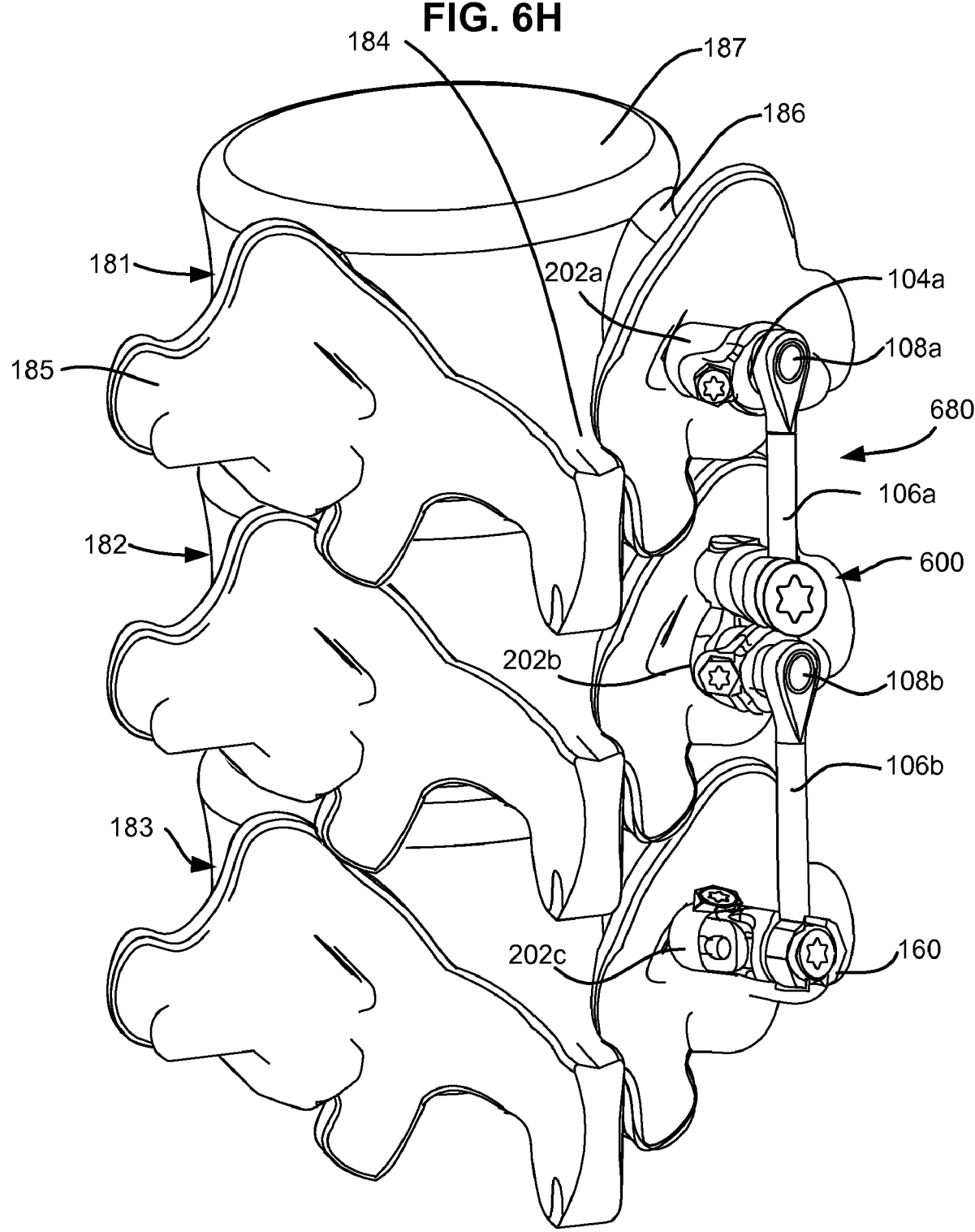

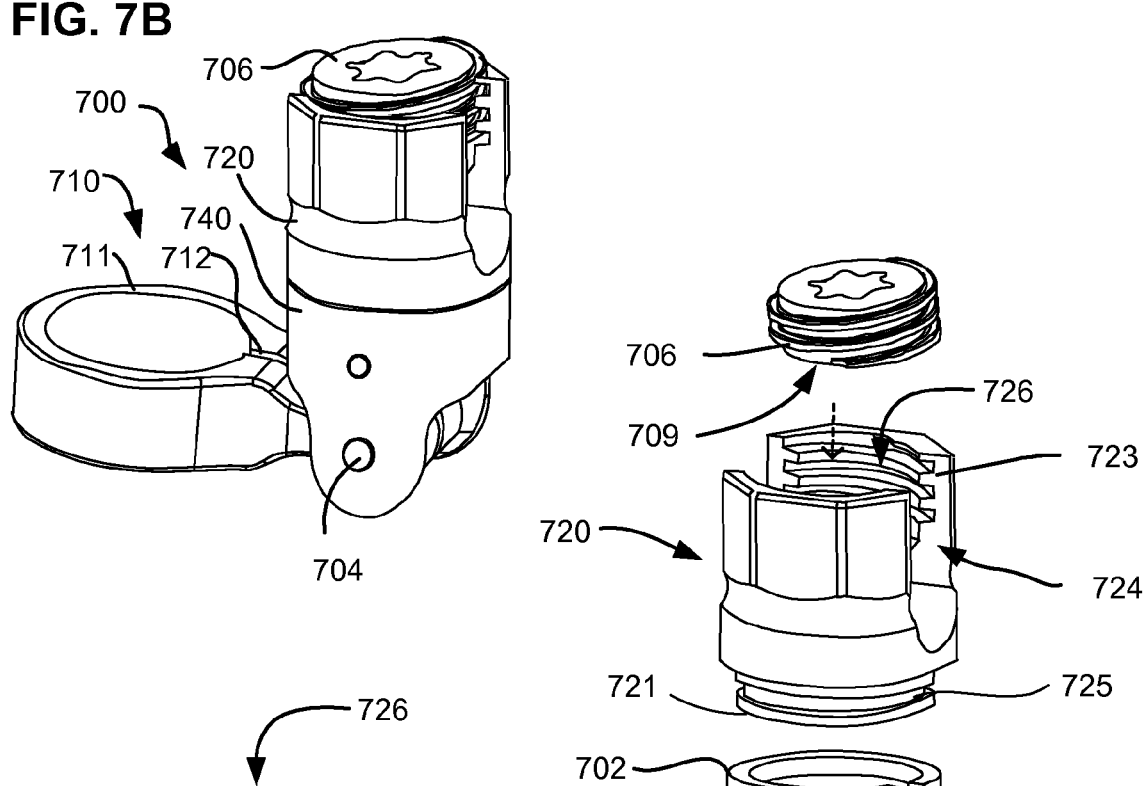
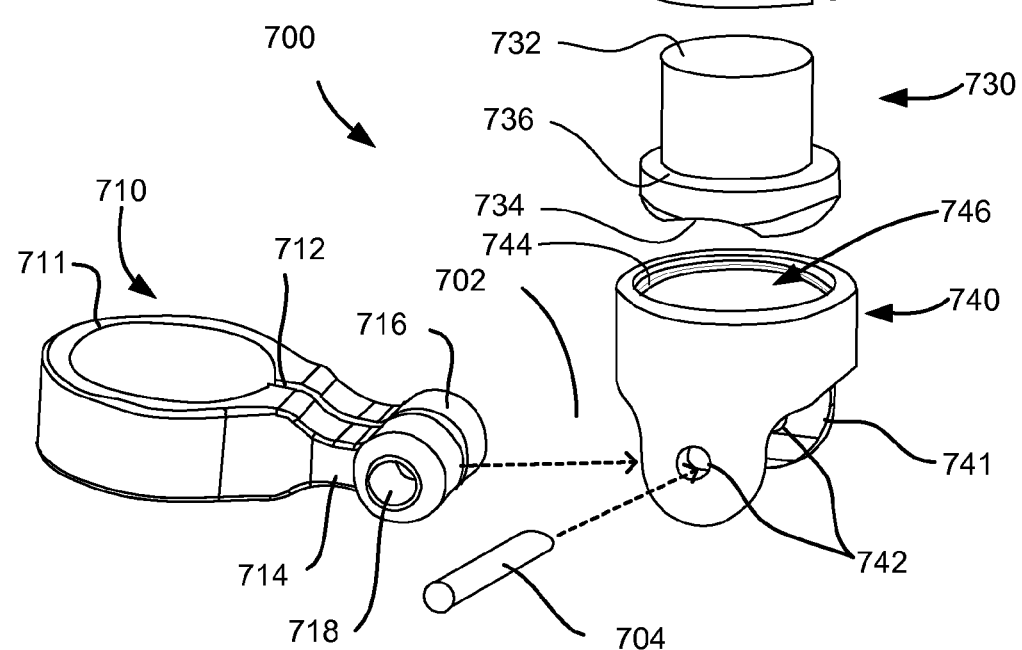
FIG. 7B
FIG. 7A

FIG. 7E
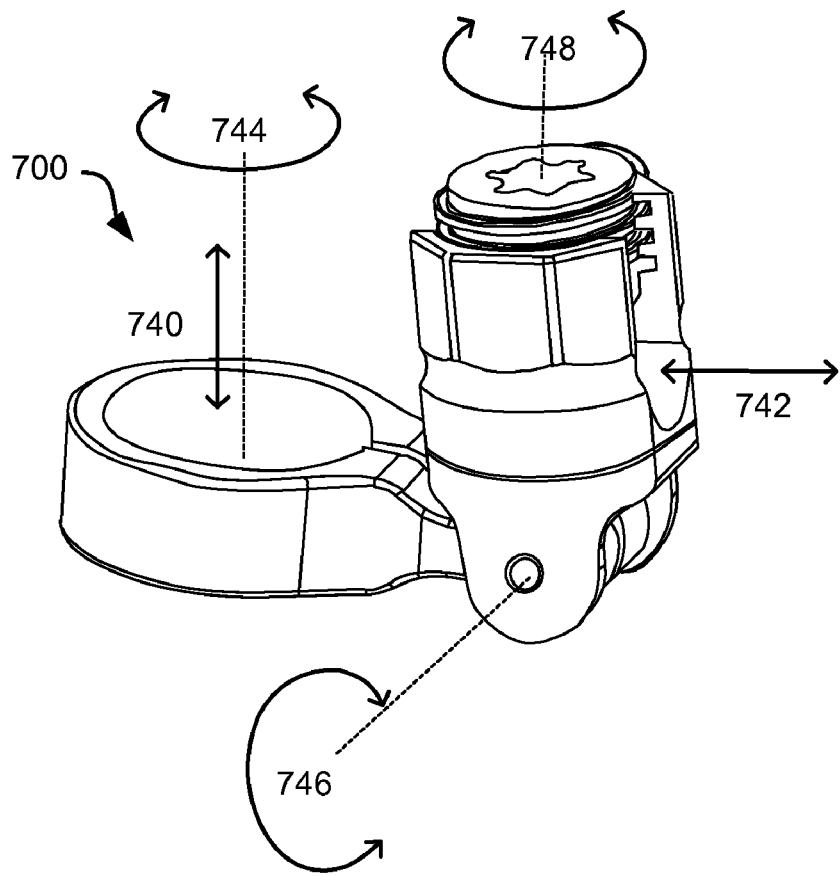
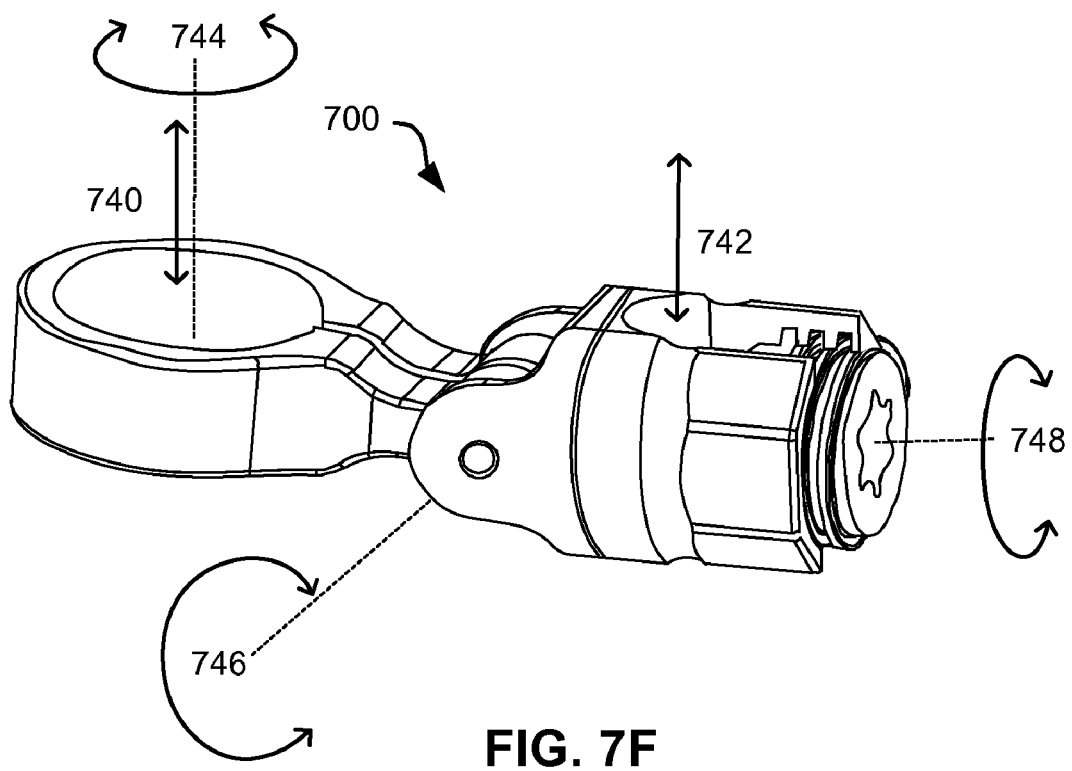
FIG. 7F

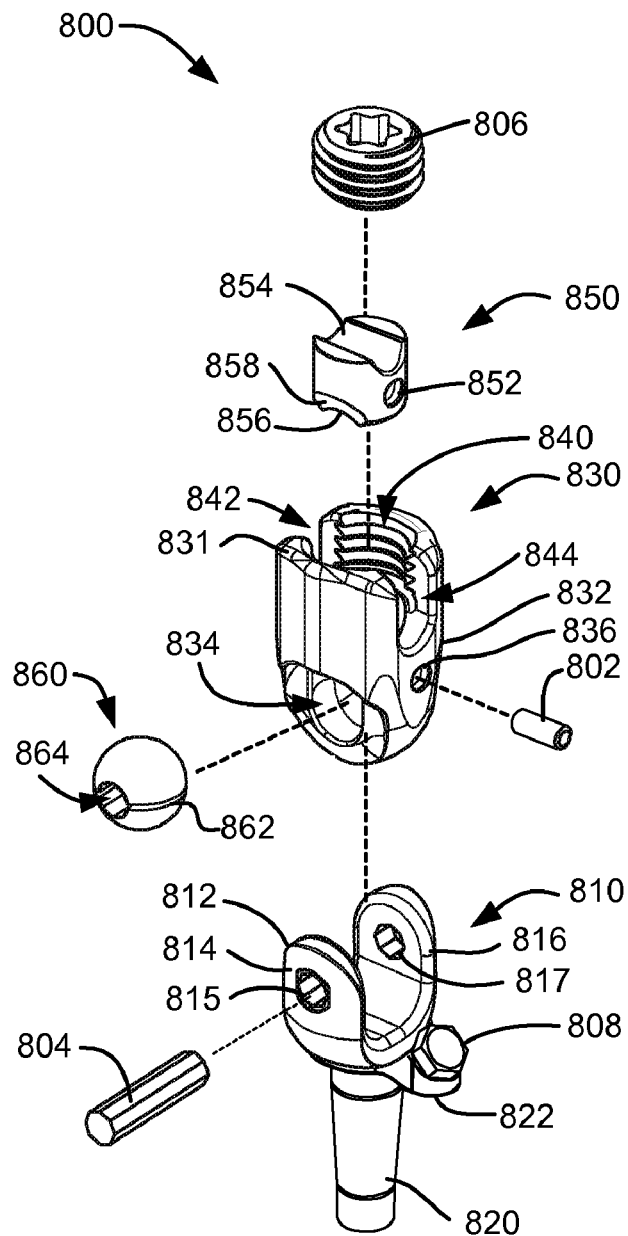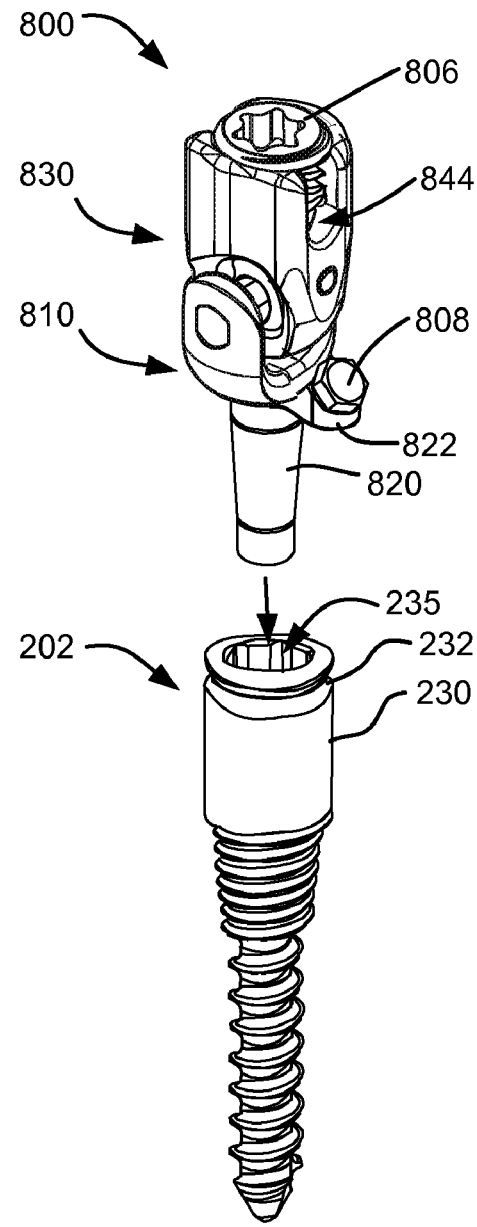

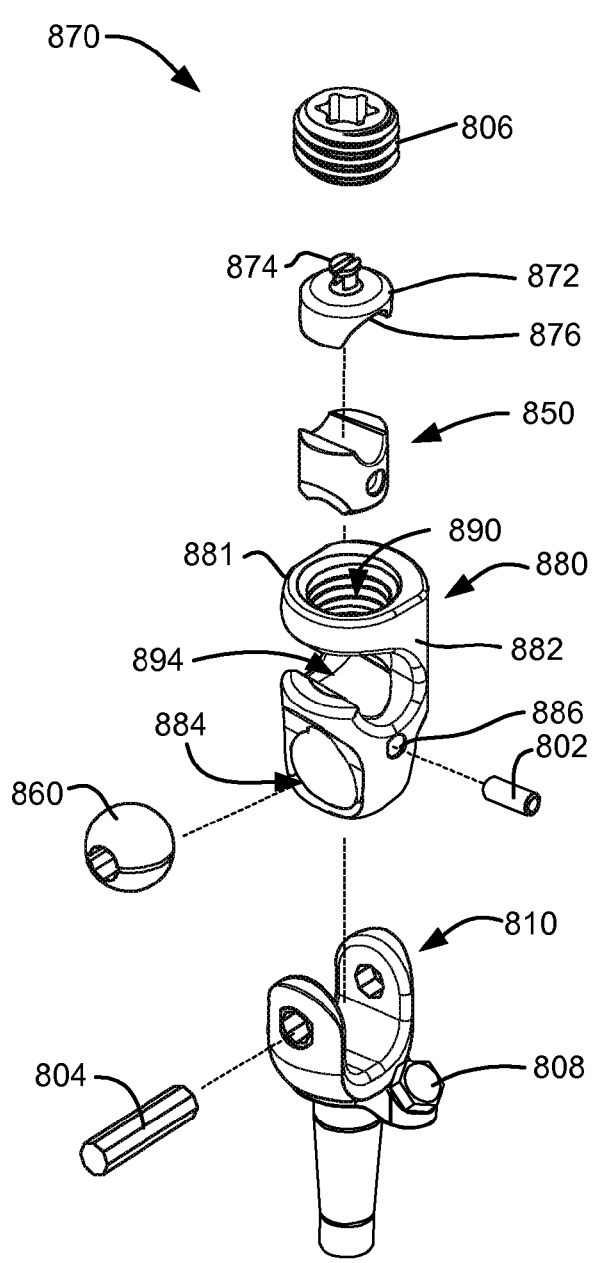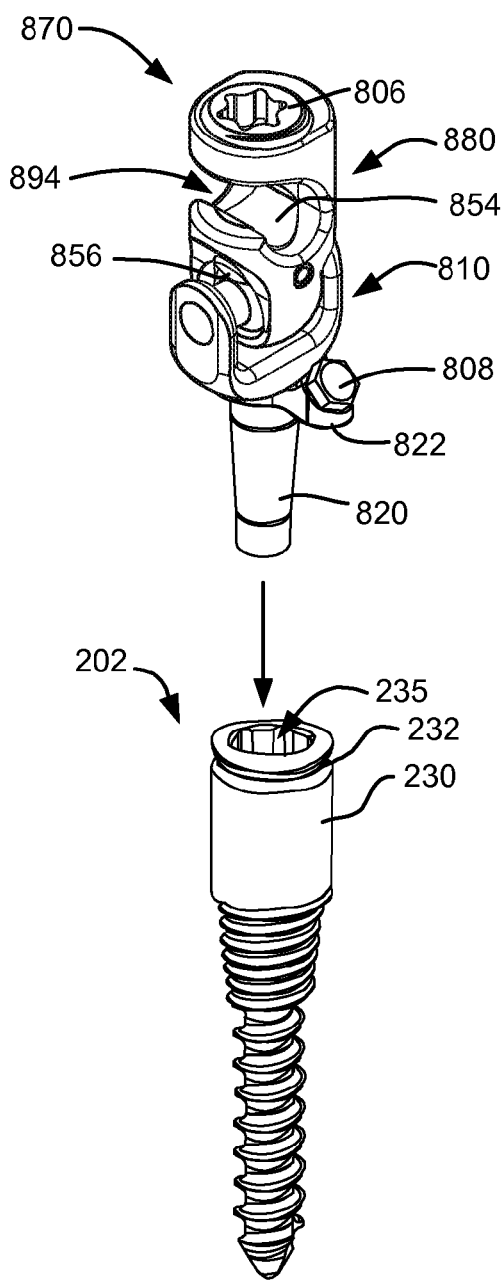
FIG. 8C
FIG. 8D

FIG. 8E
FIG. 8F
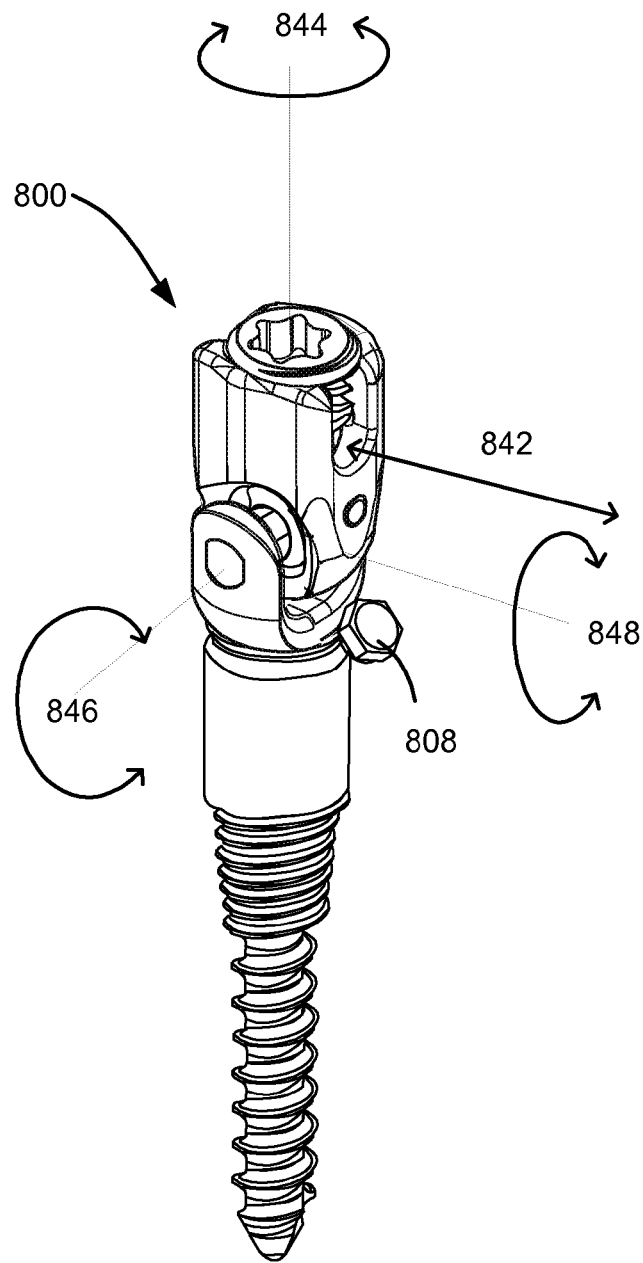
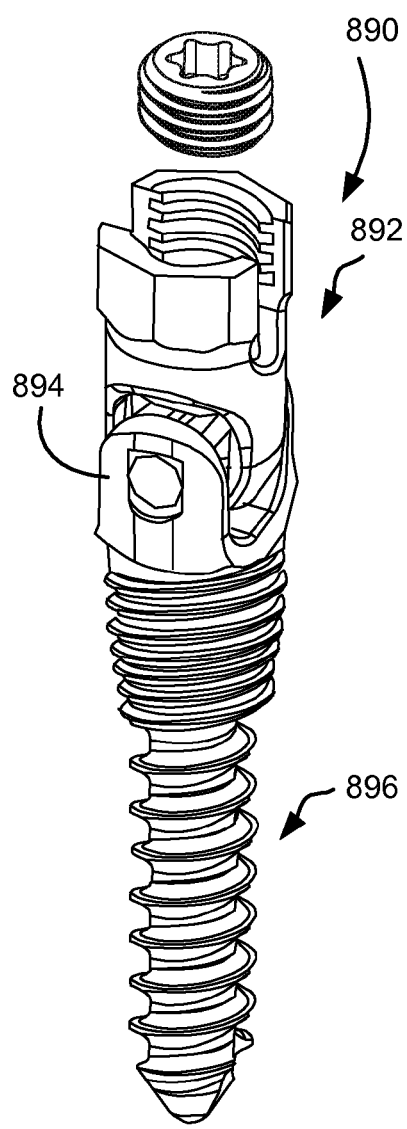

FIG. 11A
FIG. 11B
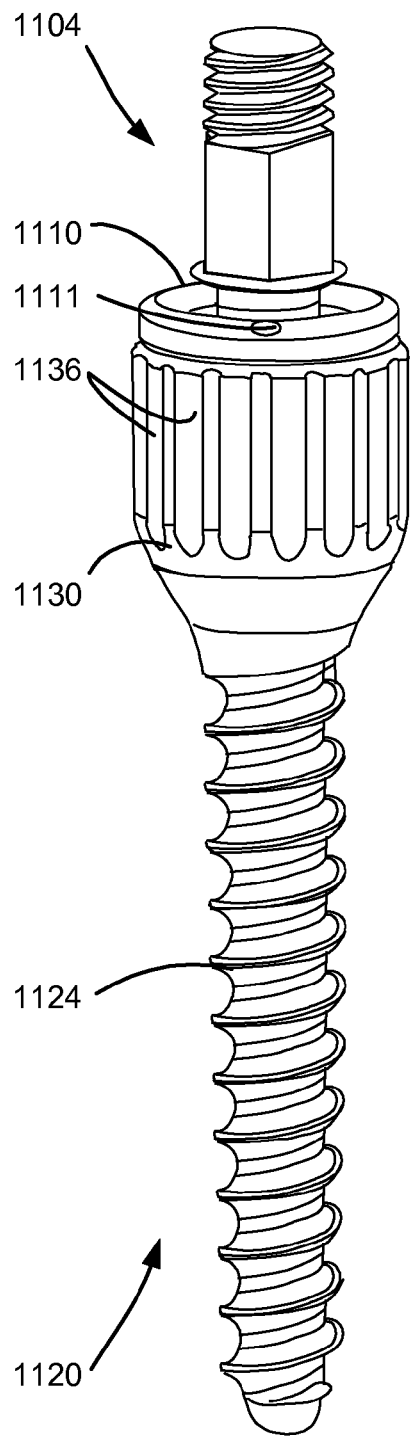
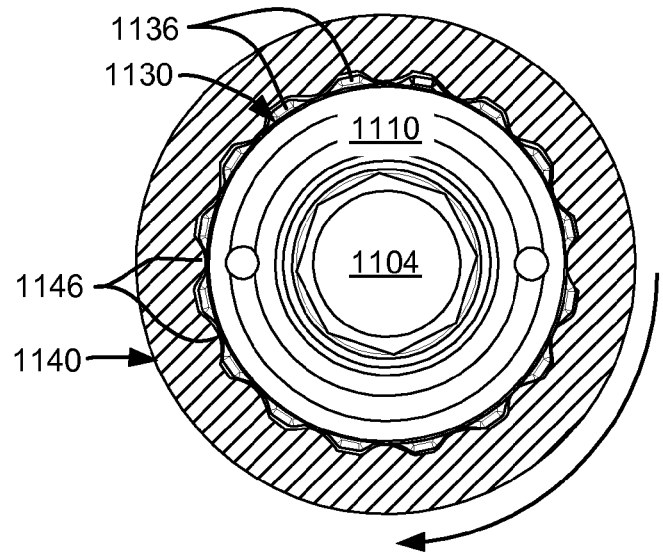
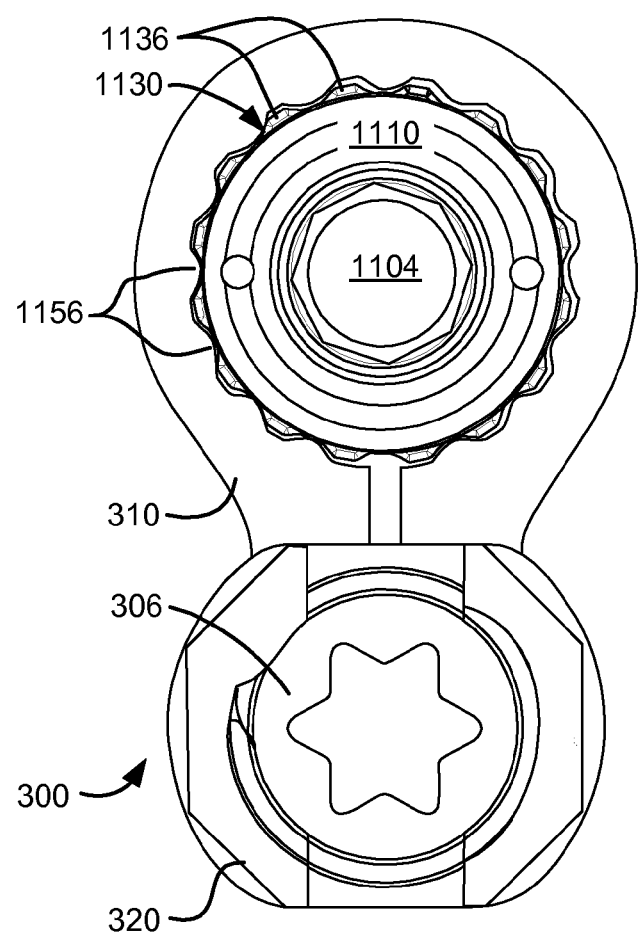
FIG. 11C

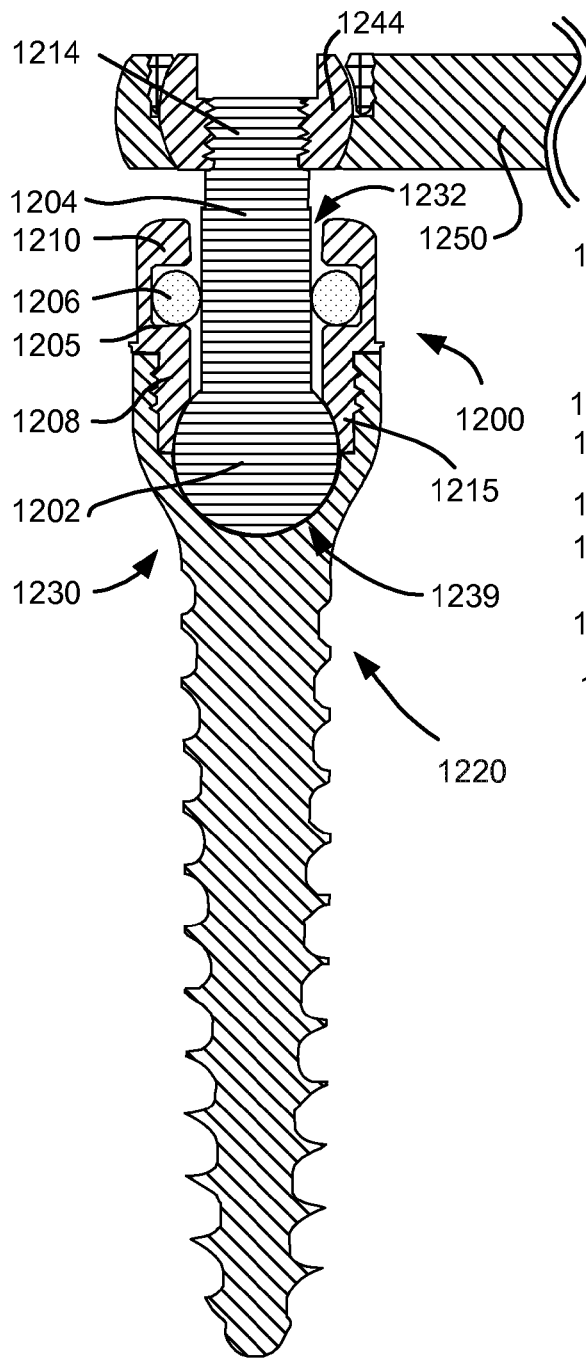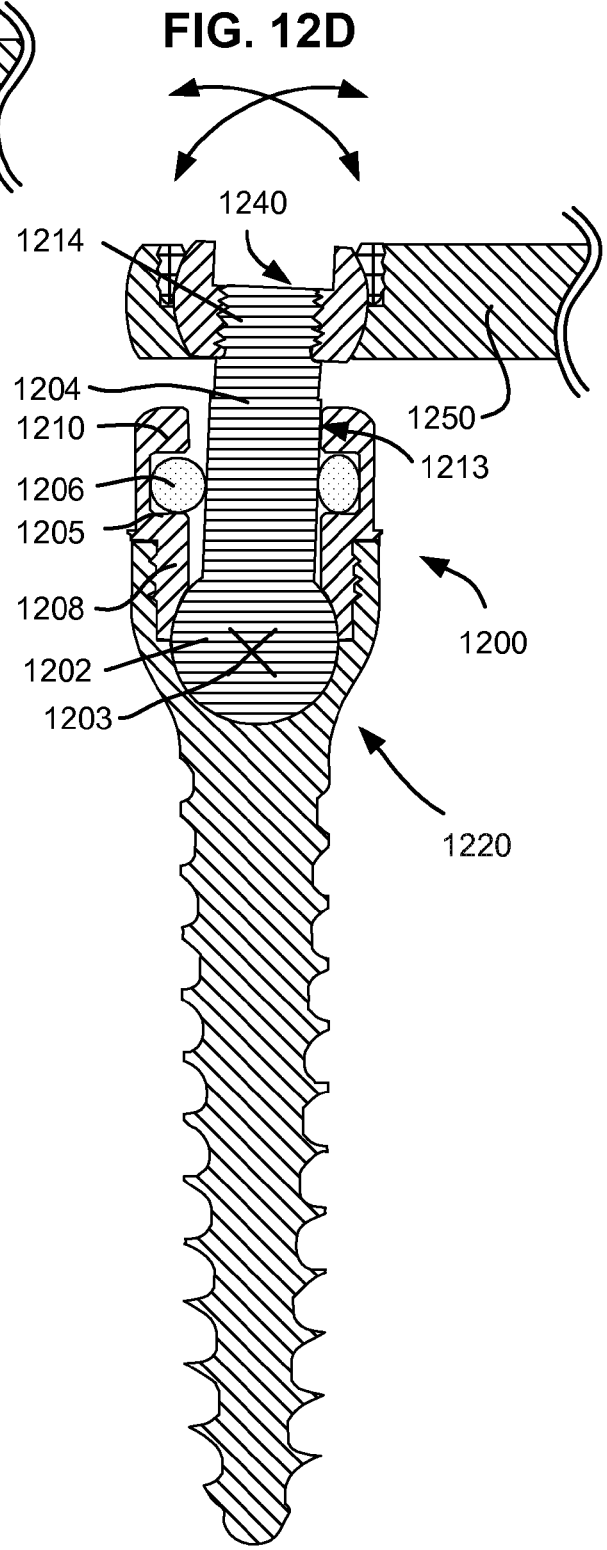

VERSATILE POLYAXIAL CONNECTOR ASSEMBLY AND METHOD FOR DYNAMIC STABILIZATION OF THE SPINE

CLAIM TO PRIORITY

This application claims priority to the following patents and patent applications:

U.S. Provisional Application No. 61/100,593 filed Sep. 26, 2008, entitled "A Spine Implant With A Deflection Rod System Selectively Alignable And Selectively Lockable To A Bone Anchor And Method"; and U.S. Provisional Application No. 61/100,625 filed Sep. 26, 2008, entitled "Versatile Components And Methods For Dynamic Stabilization"; and U.S. Provisional Application No. 61/119,651 filed Dec. 3, 2008, entitled "Load-sharing Component Having A Deflectable Post And Methods For Dynamic Spinal Stabilization"; and U.S. Provisional Application No. 61/122,658 filed Dec. 15, 2008, entitled "Load-sharing Component Having A Deflectable Post And Methods For Dynamic Spinal Stabilization"; and U.S. Provisional Application No. 61/144,426 filed Jan. 13, 2009, entitled "Load-sharing Component Having A Deflectable Post And Methods For Dynamic Spinal Stabilization"; and U.S. Provisional Application No. 61/225,478 filed Jul. 14, 2009, entitled "Load-sharing Component Having A Deflectable Post And Methods For Dynamic Spinal Stabilization"; and U.S. Provisional Application No. 61/167,789 filed Apr. 8, 2009, entitled "Load-sharing Component Having A Deflectable Post And Spring And Methods For Dynamic Spinal Stabilization"; and U.S. Provisional Application No. 61/217,556 filed Jun. 1, 2009, entitled "Load-sharing Component Having A Deflectable Post And Axially-Compressible Spring And Methods For Dynamic Spinal Stabilization".

The present application is a continuation-in-part of U.S. patent application Ser. No. 12/130,395, filed May 30, 2008, entitled "A Deflection Rod System For A Dynamic Stabilization And Motion Preservation Spinal Implantation System And Method" which claims priority to U.S. Provisional Application No. 61/031,598 filed Feb. 26, 2008 and entitled "A Deflection Rod System For A Dynamic Stabilization And Motion Preservation Spinal Implantation System And Method".

The present application is also a continuation-in-part of U.S, patent application Ser. No. 12/130,095, filed May 30, 2008, entitled "A Spine Implant With A Deflection Rod System Including A Deflection Limiting Shield Associated With A Bone Screw And Method" which claims priority to U.S. Provisional Application No. 61/057,340 filed May 30, 2008, entitled "A Spine Implant With A Deflection Rod System Aligned With A Bone Anchor And Method".

CROSS-REFERENCES TO RELATED APPLICATIONS

This application is related to all of the afore-mentioned patent applications. This application is also related to all of the following applications including:

U.S, patent application Ser. No. 12/566,478, filed Sep. 24, 2009, entitled "A Modular In-Line Deflection Rod And Bone Anchor System And Method For Dynamic Stabilization Of The Spine"; and U.S, patent application Ser. No. 12/566,485, filed Sep. 24, 2009, entitled "Versatile Polyaxial Connector Assembly And Method For Dynamic Stabilization Of The Spine"; and U.S, patent application Ser. No. 12/566,487, filed Sep. 24, 2009, entitled "Versatile Offset Polyaxial Connector And Method For Dynamic Stabilization Of The Spine"; and U.S. patent application Ser. No. 12/566,491, filed Sep. 24, 2009, entitled "Load-Sharing Bone Anchor Having A Deflectable Post and Method For Dynamic Stabilization Of The Spine"; and U.S. patent application Ser. No. 12/566,494, filed Sep. 24, 2009, entitled "Load-Sharing Component Having A Deflectable Post And Method For Dynamic Stabilization Of The Spine"; and U.S. patent application Ser. No. 12/566,498, filed Sep. 24, 2009, entitled "Load-Sharing Bone Anchor Having A Durable Compliant Member And Method For Dynamic Stabilization Of The Spine"; and U.S, patent application Ser. No. , 12/566,504, filed Sep. 24, 2009, entitled "Load-Sharing Bone Anchor Having A Deflectable Post With A Compliant Ring And Method For Stabilization Of The Spine"; and U.S. patent application Ser. No. 12/566,507, filed Sep. 24, 2009, entitled "Load-Sharing Bone Anchor Having A Deflectable Post With A Compliant Ring And Method For Stabilization Of The Spine"; and U.S. patent application Ser. No. 12/566,511, filed Sep. 24, 2009, entitled "Load-Sharing Bone Anchor Having A Deflectable Post And Method For Stabilization Of The Spine"; and U.S. patent application Ser. No. 12/566,516, filed Sep. 24, 2009, entitled "Load-Sharing Bone Anchor Having A Deflectable Post And Method For Stabilization Of The Spine"; and U.S, patent application Ser. No. 12/566,519, filed Sep. 24, 2009, entitled "Dynamic Spinal Rod And Method For Dynamic Stabilization Of The Spine"; and U.S, patent application Ser. No. 12/566,522, filed Sep. 24, 2009, entitled "Dynamic Spinal Rod Assembly And Method For Dynamic Stabilization Of The Spine"; and U.S, patent application Ser. No. 12/566,529, filed Sep. 24, 2009, entitled "Configurable Dynamic Spinal Rod And Method For Dynamic Stabilization Of The Spine"; and U.S, patent application Ser. No. 12/566,531, filed Sep. 24, 2009, entitled "A Spinal Prosthesis Having A Three Bar Linkage For Motion Preservation And Dynamic Stabilization Of The Spine"; and U.S. patent application Ser. No. 12/566,534, filed Sep. 24, 2009, entitled "Surgical Tool And Method For Implantation of A Dynamic Bone Anchor"; and U.S, patent application Ser. No. 12/566,547, filed Sep. 24, 2009, entitled "Surgical Tool And Method For Connecting A Dynamic Bone Anchor and Dynamic Vertical Rod"; and U.S, patent application Ser. No. 12/566,551, filed Sep. 24, 2009, entitled "Load-Sharing Bone Anchor Having A Deflectable Post And Centering Spring And Method For Dynamic Stabilization Of The Spine"; and U.S, patent application Ser. No. 12/566,553, filed Sep. 24, 2009, entitled "Load-Sharing Component Having A Deflectable Post And Centering Spring And Method For Dynamic Stabilization Of The Spine"; and U.S, patent application Ser. No. 12/566,559, filed Sep. 24, 2009, entitled "Load-Sharing Bone Anchor Having A Deflectable Post And Axial Spring And Method For Dynamic Stabilization Of The Spine".

All of the afore-mentioned patent applications are incorporated herein by reference in their entireties.

BACKGROUND OF INVENTION

Back pain is a significant clinical problem and the costs to treat it, both surgical and medical, is estimated to be over $2 billion per year. One method for treating a broad range of degenerative spinal disorders is spinal fusion. Implantable medical devices designed to fuse vertebrae of the spine to treat have developed rapidly over the last decade. However, spinal fusion has several disadvantages including reduced range of motion and accelerated degenerative changes adjacent the fused vertebrae.

Alternative devices and treatments have been developed for treating degenerative spinal disorders while preserving motion. These devices and treatments offer the possibility of treating degenerative spinal disorders without the disadvantages of spinal fusion. However, current devices and treatments suffer from disadvantages e.g., complicated implantation procedures; lack of flexibility to conform to diverse patient anatomy; the need to remove tissue and bone for implantation; increased stress on spinal anatomy; insecure anchor systems; poor durability, and poor revision options. Consequently, there is a need for new and improved devices and methods for treating degenerative spinal disorders while preserving motion.

SUMMARY OF INVENTION

The present invention includes a versatile spinal implant system and methods that can dynamically stabilize the spine while providing for the preservation of spinal motion. Embodiments of the invention provide a dynamic stabilization system which includes: versatile components, adaptable stabilization assemblies, and methods of implantation. An aspect of embodiments of the invention is the ability to stabilize two, three and/or more levels of the spine by the selection of appropriate components of embodiments of the invention for implantation in a patient. Another aspect of embodiments of the invention is the ability to accommodate particular anatomy of the patient by providing a system of versatile components which may be customized to the anatomy and needs of a particular patient and procedure. Another aspect of the invention is to facilitate the process of implantation and minimize disruption of tissues during implantation.

Thus, the present invention provides new and improved systems, devices and methods for treating degenerative spinal disorders by implanting a dynamic spinal stabilization assembly which supports the spine while preserving motion. These and other objects, features and advantages of the invention will be apparent from the drawings and detailed description which follow.

BRIEF DESCRIPTION OF THE DRAWINGS

FIGS. 1A and 1B are perspective views of a deflection system component mounted to an anchor system component in accordance with an embodiment of the present invention.

FIGS. 1C and 1D are perspective views of a connection system component mounted to an anchor system component in accordance with an embodiment of the present invention.

FIG. 2D is a sectional view of an alternative deflection rod assembly in accordance with an embodiment of the present invention.

FIG. 2E is a perspective view of an alternative deflection rod assembly and bone anchor in accordance with an embodiment of the present invention.

FIG. 2F is an alternate view of the deflection rod assembly of FIG. 2E in combination with a vertical rod.

FIGS. 3A to 3C are perspective and exploded views of a polyaxial connector and its components in accordance with an embodiment of the present invention.

FIGS. 3D to 3E are views illustrating the clamping action of the polyaxial connector of FIGS. 3A to 3C.

FIG. 3F is a perspective view illustrating the degrees of freedom of the polyaxial connector of FIGS. 3A to 3E.

FIGS. 4A to 4C are perspective and exploded views of a polyaxial connector and its components in accordance with an embodiment of the present invention.

FIGS. 4D to 4E are views illustrating the clamping action of the polyaxial connector of FIGS. 4A to 4C.

FIG. 4F is a perspective view illustrating the degrees of freedom of the polyaxial connector of FIGS. 4A to 4E.

FIGS. 5A to 5D are perspective and exploded views of a polyaxial connector and its components in accordance with an embodiment of the present invention.

FIG. 6H is a posterior view of a multi-level dynamic spine stabilization assembly utilizing the polyaxial connector of FIGS. 6A to 6G in accordance with an embodiment of the present invention.

FIGS. 7A and 7B are perspective and exploded views of an alternate polyaxial connector and its components in accordance with an embodiment of the present invention.

FIGS. 7E and 7F are perspective views illustrating the degrees of freedom of the polyaxial connector of FIGS. 7A to 7D.

FIGS. 8A and 8B are perspective and exploded views of a polyaxial connector and its components in accordance with an embodiment of the present invention.

FIGS. 8C and 8D are perspective and exploded views of an alternate polyaxial connector and its components in accordance with an embodiment of the present invention.

FIG. 8E is a perspective view illustrating the degrees of freedom of the alternate polyaxial connector of FIGS. 8A and 8B.

FIG. 8F is a perspective view of an integrated bone anchor and polyaxial connector.

FIG. 11A is a perspective view of an alternative bone anchor assembled with a deflection rod according to an embodiment of the invention.

FIG. 11B is a posterior view of the bone anchor and deflection rod of FIG. 11A showing engagement by a wrench in accordance with an embodiment of the invention.

FIG. 11C is a plan view of the bone anchor and deflection rod of FIG. 11A showing engagement by a connector in accordance with an embodiment of the invention.

FIG. 12C is a sectional view of the deflection rod assembly of FIGS. 12A and 12B.

FIG. 12D is a sectional view of the deflection rod assembly of FIGS. 12A and 12B showing deflection.

DETAILED DESCRIPTION OF THE PREFERRED EMBODIMENTS

Figure 1E:
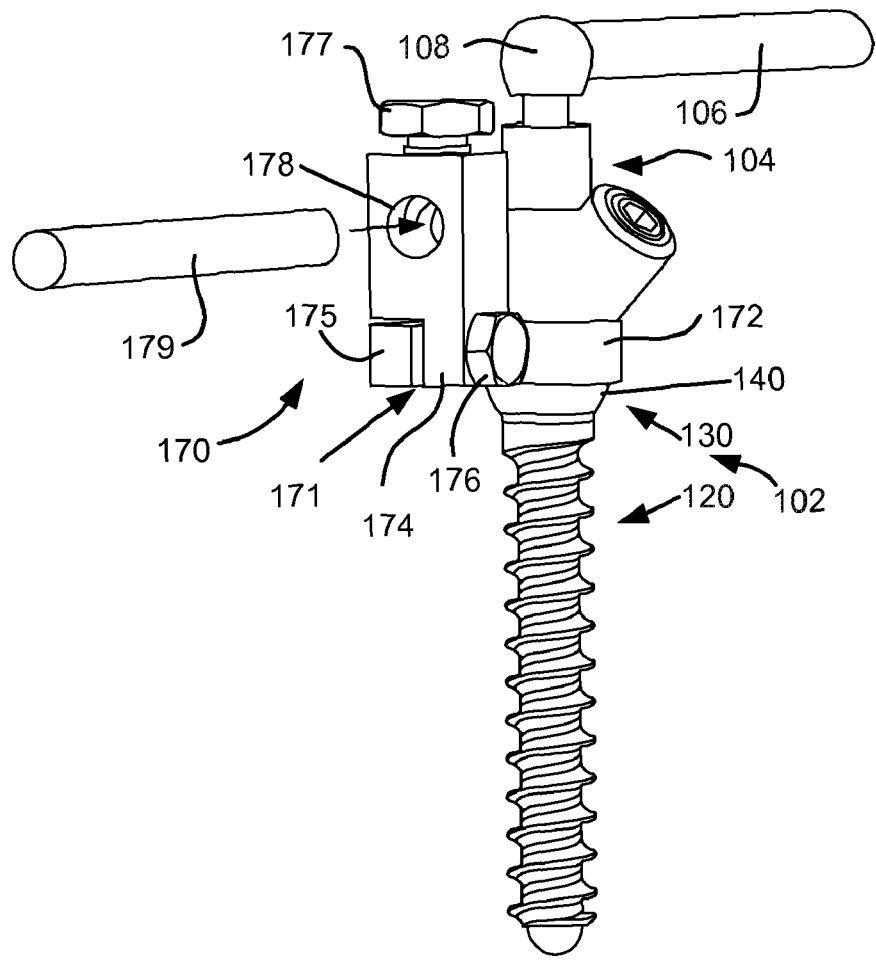
FIGS. 1E and 1F are perspective and posterior views of a deflection system component and a connection system component mounted to a single anchor system component in accordance with an embodiment of the present invention.

The present invention includes a versatile spinal implant system, components and methods which can dynamically stabilize the spine while providing for the preservation of spinal motion. Alternative embodiments can be used for spinal fusion. Embodiments of the invention include a construct with an anchor system, a deflection system, a vertical rod system and a connection system. The deflection system provides dynamic stabilization while reducing the stress exerted upon the bone anchors and spinal anatomy. The connection system includes connection components which allow for appropriate, efficient and convenient placement of the anchor system relative to the spine in order to reduce the force that is placed on the anchor system. The connection components have enhanced degrees of freedom which contribute to the ease of implantation of the anchor system.

An aspect of the invention is to stabilize the spine while preserving motion between the vertebrae of the spine through the use of appropriately selected bone anchors, deflection rods, vertical rods and adjustable connectors (and optionally horizontal rods) of embodiments of the invention.

Another aspect of embodiments of the invention is the ability to accommodate the particular anatomy of the patient by providing a system of components which may be customized to the anatomy and needs of a particular patient and a procedure that allows the implantation system to have enhanced degrees of freedom of placement of the implant.

Another aspect of the embodiments of the invention is to provide a modular system which can be customized to the needs of the patient. A deflection system can be selectively chosen for the particular patient as well the particular levels of the vertebrae of the spine that are treated. Further, the positioning of the embodiments of the invention can be selected to control stiffness and stability.

Another aspect of embodiments of the invention is the ability to stabilize two, three and/or more levels of the spine by the selection of appropriate embodiments and components of embodiments of the invention for implantation in a patient. Further embodiments of the invention allow for fused levels to be placed next to dynamically stabilized levels. Such embodiments of the invention enable vertebral levels adjacent to fusion levels to be shielded by providing a more anatomical change from a rigid fusion level to a dynamically stable, motion preserved, and more mobile level.

A further aspect of the invention is that the implant is constructed around features of the spine, e.g. the spinous processes, and, thus, such features do not need to be removed and the implant does not get in the way of the normal motion of the spine features and the spine features do not get in the way of the operation of the implant. As the load is carried along the deflection rod or loading rod, the embodiments of the invention can be made smaller in order to fit in more spaces relative to the spine.

A further aspect of the invention, due to the ease of implanting the anchor system, is the ability to accommodate the bone structure of the spine, even if adjacent vertebrae are misaligned with respect to each other.

Yet a further aspect of the invention is to provide for dynamic stabilization and motion preservation while preserving the bone and tissues of the spine in order to lessen trauma to the patient and to use the existing functional bone and tissue of the patient as optimally as possible in cooperation with embodiments of the invention.

A further aspect of the invention is to implant the embodiment of the invention with a procedure that does not remove or alter bone or tear or sever tissue. In an aspect of the invention the muscle and other tissue can be urged out of the way during the inventive implantation procedure. Accordingly, an aspect of the invention is to provide for a novel implantation procedure that is minimally invasive.

Still another aspect of the invention is the ability to maximize the range of motion of the spine after embodiments of the dynamic stabilization, motion preservation implant of the invention are implanted in a patient. Still another aspect of the invention is the preservation of the natural motion of the spine and the maintenance of the quality of motion as well as the wide range of motion so that the spine motion is as close to that of the natural spine as possible. Accordingly, this aspect of the invention is directed to restoring the normal motion of the spine.

Another aspect of embodiments of the invention is that embodiments can be constructed to provide for higher stiffness and fusion at one level or to one portion of the spine while allowing for lower stiffness and dynamic stabilization at another adjacent level or to another portion of the spine.

In specific embodiments of the present invention, a dynamic stabilization system is provided which includes adaptable components and methods for assembling a dynamic stabilization assembly which supports the spine while providing for the preservation of spinal motion. The dynamic stabilization system has an anchor system, a deflection system, a vertical rod system and a connection system. The anchor system anchors the construct to the spinal anatomy. The deflection system provides dynamic stabilization while reducing the stress exerted upon the bone anchors and spinal anatomy. The vertical rod system connects different levels of the construct in a multilevel assembly and may in some embodiments include compound deflection rods. The connection system includes coaxial connectors (coaxial or in-line with a bone anchor) and offset connectors (offset from the axis of a bone anchor) which adjustably connect the deflection system, vertical rod system and anchor system allowing for appropriate, efficient and convenient placement of the anchor system relative to the spine. Alternative embodiments can be used for spinal fusion.

Common reference numerals are used to indicate like elements throughout the drawings and detailed description; therefore, reference numerals used in a drawing may or may not be referenced in the detailed description specific to such drawing if the associated element is described elsewhere. The first digit in a three digit reference numeral indicates the series of figures in which the referenced item first appears. Likewise, the first two digits in a four digit reference numeral. Further, the terms "vertical" and "horizontal" are used throughout the detailed description to describe general orientation of structures relative to the spine of a human patient that is standing. This application also uses the terms proximal and distal in the conventional manner when describing the components of the spinal implant system. Thus, proximal refers to the end or side of a device or component closest to the hand operating the device, whereas distal refers to the end or side of a device furthest from the hand operating the device. For example, the tip of a bone screw that enters a bone would conventionally be called the distal end (it is furthest from the surgeon) while the head of the screw would be termed the proximal end (it is closest to the surgeon).

Figure 1F:
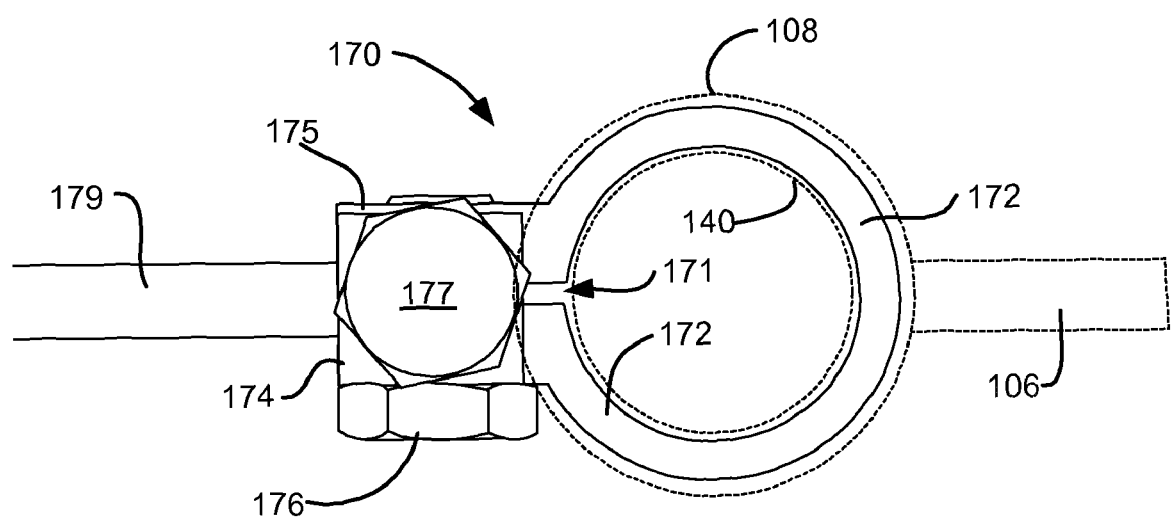
Figure 1G:
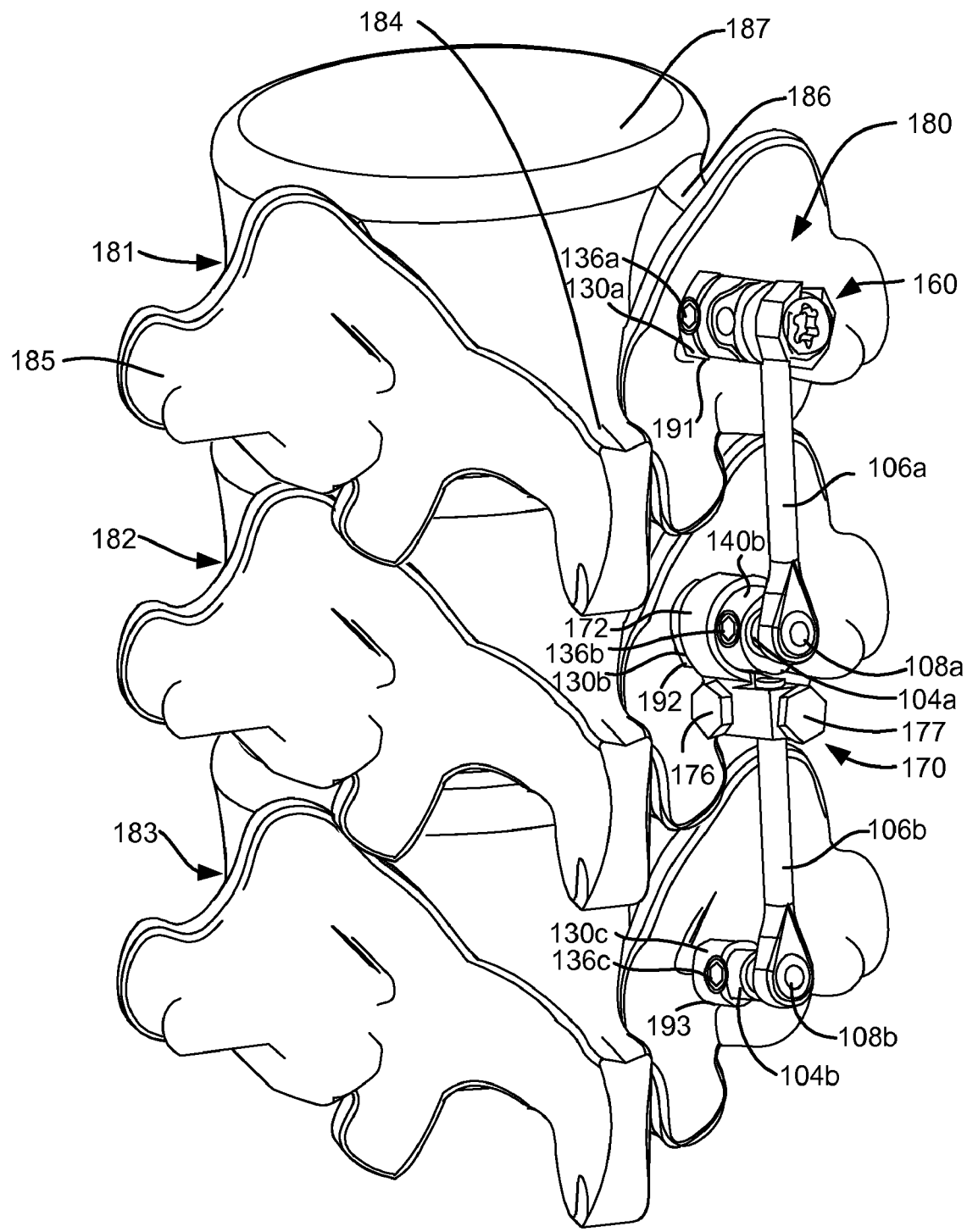
FIG. 1G is a posterior view of a multi-level dynamic stabilization assembly utilizing the components of FIGS. 1A to 1F in accordance with an embodiment of the present invention.

FIGS. 1A and 1B show components of the deflection system mounted to components of the anchor system in accordance with embodiments of the present invention. FIGS. 1C and 1D show examples of connection components mounted to anchor systems components without deflection rod assembly components. FIGS. 1E and 1F show examples of connection components mounted to anchor system in conjunction with deflection rod assembly components. FIG. 1G shows an example of a construct comprising a plurality of anchor system components, deflection rod assembly components and connection system components.

Referring now to FIGS. 1A and 1B, which show components of the dynamic stabilization assembly in accordance with the present invention. FIG. 1A shows a bone anchor 102 and a deflection rod 104 connected to a vertical rod 106 by a ball joint 108. Bone anchor 102 includes a bone screw 120 and housing 130.

Bone anchor 102 is an example of a component of the anchor system. As shown in FIG. 1A, bone anchor 102 is a bone screw 120 having one or more threads 124 which engage a bone to secure the bone anchor 102 onto a bone. The anchor system may include one or more alternative bone anchors known in the art, e.g. bone hooks, expanding devices, barbed devices, threaded devices, adhesive and other devices capable of securing a component to bone instead of or in addition to bone screw 120. Bone anchor 102 includes a housing 130 at the proximal end. Housing 130 comprises a cavity 132 (shown by dashed lines) for receiving deflection rod 104. Cavity 132 is coaxial with threaded bone screw 120. Housing 130 also comprises a fastener 134 for securing deflection rod 104 within housing 130. As shown in FIG. 1A, fastener 134 comprises a threaded screw hole 138 extending along an axis at an acute angle to the axis of the cavity 132. Threaded screw hole 138 receives a locking set screw 136 which, when seated (FIG. 1B), protrudes into the cavity 132 of housing 130 and against the deflection rod 104, where the deflection rod 104 is seated within the housing 130. The locking set screw 136 thereby secures the deflection rod 104 in place within the housing 130.

Deflection rod 104 is an example of a component of the deflection system. Deflection rod 104 is a component having controlled flexibility which allows for load sharing. The deflection rod 104 provides stiffness and support where needed to support the loads exerted on the spine during normal spine motion, which loads, the soft tissues of the spine are no longer able to accommodate since these spine tissues are either degenerated or damaged. Load sharing is enhanced by the ability to select the appropriate stiffness of the deflection rod or loading rod in order to match the load sharing characteristics desired. For embodiments of this invention, the terms "deflection rod" and "loading rod" can be used interchangeably. Deflection rods, deflection rod mountings and alternative deflection rods are described in more detail below in the section "Deflection Rods/Loading Rods."

Typically, bone anchor 102 is fixed to a bone in the position desired by a surgeon prior to installation of a deflection rod 104 and or other components. FIG. 1B shows deflection rod 104 installed in housing 130 of bone anchor 102. Deflection rod 104 is inserted into cavity 132 of housing 130. As shown in FIGS. 1A and 1B, deflection rod 104 is oriented in a co-axial or collinear or parallel orientation to a bone anchor screw. This arrangement simplifies implantation, reduces trauma to structures surrounding an implantation site, and reduces system complexity. Arranging the deflection rod 104 co-axial with a shaft of the bone anchor 102 can substantially transfer a moment force applied by the deflection rod 104 from a moment force tending to pivot or rotate the bone anchor 102 about the axis of the shaft, to a moment force tending to act perpendicular to the axis of the shaft. The deflection rod can thereby effectively resist repositioning of the deflection rod and/or bone anchor 102 without the use of locking screws or horizontal bars to resist rotation. Further examples of deflection rods are provided below.

Set screw 136 is positioned within threaded opening 138 of housing 130 and tightened to engage the exterior of deflection rod 104 within housing 130 thus securing deflection rod 104 within housing 130. The housing 130 permits the surgeon to select the bone anchor 102 and deflection rod 104 independently depending upon the functional needs and anatomy of the patient. For example, the surgeon may select a smaller bone screw for use in smaller bones, e.g. in the cervical region. The surgeon may also select a deflection rod 104 which has an appropriate stiffness for the patient. Further, if several deflection rods 104 are used in a patient, each deflection rod 104, if desired, can have a different stiffness.

Housing 130 also includes a coupling/outer surface 140 to which other components may be mounted. As shown in FIG. 1A, coupling 140 is the external cylindrical surface of housing 130. Housing 130 includes two mounting positions, one coaxial mounting position and one external mounting position. Thus, a single bone anchor 102 can serve as the mounting point for one, two or more components. A deflection rod 104 may be coaxially mounted in the cavity 132 of the housing and one or more additional components may be mounted to the coupling/outer surface 140 of the housing. For example, a component of the connection system may be mounted to the coupling/outer surface 140 of the housing— such a connector may be called an offset head or offset connector. In some applications, a component of the connection system may be coaxially mounted in the cavity 132 in place of a deflection rod 104—such a connector may be called a coaxial head or coaxial connector.

In some embodiments of the present invention, a connection system component, e.g. a polyaxial connector may be mounted in the cavity 132 of a bone anchor 102 to secure the bone anchor to a vertical rod. For example, FIGS. 1C and 1D show coaxial head 160 which is a polyaxial connector which is coaxially mounted within the cavity 132 of the housing 130 of bone anchor 102. Coaxial head 160 is an example of a coaxial head or coaxial connector. Bone anchor 102 is the same bone anchor previously described with respect to FIGS. 1A and 1B. Coaxial head 160 comprises a rod 162 which is designed to fit within cavity 132 of housing 130. Rod 162 and cavity 132 may in some case be circular in section (e.g. cylindrical), in which case, rod 162 can rotate within cavity 132 until locked into place by fastener 134. Rod 162 may be provided with a groove by which fastener 134 may, in a first position, secure rod 162 against removal from cavity 132 without preventing rotation of rod 162 within cavity 132. In alternative embodiments, rod 162 may be polygonal in section such that it fits in one of a fixed number of possible positions. The ability to coaxially mount coaxial head 160 to a bone anchor 102 has several advantages over a standard polyaxial bone screw in which a polyaxial connector is an integral part of the device and may not be removed or exchanged. The bone anchor 102 is simpler to install and there is no risk of damage to the polyaxial connector during installation. A single coaxial head can be manufactured and designed to mount to a range of different bone anchors thus allowing bone anchors to be selected as appropriate for the patient's anatomy. After the bone anchor is installed, the orientation of the coaxial head can be adjusted without changing the screw depth (this is not possible in a standard polyaxial bone screw without also turning the screw). After the bone anchor is implanted one of a range of different coaxial heads may be installed without requiring removal of the bone anchor. Likewise, if a revision is required, the coaxial head may be exchanged for a different component without necessitating removal of the bone anchor 102. Coaxial heads/connectors, coaxial head/connector mountings and alternative coaxial heads/connectors are described in more detail below in the section "Versatile Coaxial Heads."

Referring again to FIGS. 1C and 1D, attached to rod 162 of coaxial head 160 is a yoke 164. Yoke 164 is connected to a ball 165 by a hexagonal pin 162. A saddle 163 is also mounted to ball 165 such that saddle 163 can pivot about two orthogonal axes relative to yoke 164. Saddle 163 has an aperture 168 through which a vertical rod may be passed. On one side of aperture 168 is a plunger 169. On the other side of aperture 168 is a locking set screw 167. When a rod 106 (not shown) is positioned within aperture 168 and locking set screw 167 is tightened down as shown in FIG. 1D, the locking set screw 167 forces the rod 106 down onto the plunger 169. Plunger 169 is, in turn, forced down by rod 106 against ball 165. Plunger 169 engages ball 165, and ball 165 engages rod 106, to lock saddle 163 in position relative to yoke 164 and secure a rod (e.g. vertical rod 106) to saddle 163. In this way, tightening set screw 167 secures the rod 106 and locks the position and orientation of coaxial head. Additional, coaxial heads for coaxial mounting to bone anchors are described in detail below.

As described above, bone anchor 102 has a housing which can accept one coaxially-mounted component (e.g. a coaxial head) and one externally-mounted component (e.g. an offset connector). FIGS. 1E and 1F show a component of the connection system which may be mounted externally to the housing 130 of bone anchor 102 in conjunction with a coaxially-mounted deflection rod. FIG. 1E shows a perspective view of connector 170 mounted externally to housing 130 of bone anchor 102 in which a deflection rod 104 is coaxially mounted. Connector 170 is an example of a component of the connection system and may be termed an offset head or offset connector. FIG. 1F shows a plan view of the connector 170.

As shown in FIGS. 1E and 1F, connector 170 comprises a clamp ring 172 at each end of which there is formed an ear 174 and 175. A screw 176 passes through ear 174 into a threaded hole in ear 175. By tightening screw 176, ears 174 and 175 can be pulled together reducing the gap 171 in clamp ring 172. When gap 171 is at its largest size, clamp ring 172 is designed to be only slightly larger than the exterior diameter of a housing 130 (shown by dashed line in FIG. 1F). Thus, clamp ring 172 may rotate around housing 130 and slide up and down housing 130 to be positioned and oriented as desired by the surgeon. When gap 171 is reduced by tightening screw 176, the inner diameter of clamp ring 172 is forced into contact with the outer surface 140 of a housing 130. Thus, clamp ring 172 fixes connector 170 in place and secures connector 170 to housing 130 of bone anchor 102.

As shown in FIG. 1E, connector 170 also has an aperture 178 for receiving a rod 179. Rod 179 may be a vertical rod (e.g. a second vertical rod 106). Aperture 178 passes all the way through ear 175 so that a rod 179 may slide into and through aperture 178. A screw 177 is mounted in a threaded hole which intersects aperture 178. When screw 177 is tightened, it either contacts rod 179 directly or forces another component into contact with rod 179 thereby locking rod 179 relative to connector 170 and securing rod 179 to connector 170. In an alternative design, the axis of aperture 178 may be rotated through 90 degrees such that it is parallel to the axis of screw 176.

Connector 170 provides three degrees of freedom in attachment of rod 179 to bone anchor 102. As used herein, the degrees of freedom (DOF) of a connector are the set of independent displacements and/or rotations that specify the orientation and position of the aperture for receiving the rod. For example, connector 170 may rotate around housing 130 and may slide up and down housing 130 prior to tightening screw 176. Rod 179 may also slide in and out of aperture 178. These are the only degrees of freedom (DOF) for this connector. Connector 170 thus has limited flexibility with respect to the orientation of vertical rod 179 relative to the longitudinal axis of bone anchor 102. The angle that rod 179 makes with the longitudinal axis of bone anchor 102 cannot be varied with connector 170. Connector 170, as shown, requires that rod 179 be perpendicular to the axis of bone anchor 102. However, connectors having greater degrees of freedom (DOF) and thereby providing more flexibility for assembly of the dynamic stabilization assembly are described below. Offset connectors, offset connector mountings and alternative offset connectors are described in more detail below in the section "Versatile Offset Connectors/Heads."

The components introduced in FIGS. 1A-1F may be used to construct a dynamic stabilization assembly for one or more levels of the spine of a patient. A one level assembly is preferably used to span one disk space and be secured to the vertebra above the disk space and secured to the vertebra below the disk space. A two-level assembly spans two disk spaces with the assembly attached to the first and second vertebrae which are on either side of a first disk space and also attached to the second and third vertebrae which are on either side of a second disk space. It is to be understood that while a one-level assembly will generally be attached to two adjacent vertebrae and a two-level assembly will generally be attached to three adjacent vertebrae, that in other embodiments, the systems can be attached to non-adjacent vertebra. Thus, the one-level assembly can be secured to two vertebrae that are not adjacent. Similarly, the two-level assembly can be attached to three vertebrae, some or all of said vertebrae not being adjacent to each other.

FIG. 1G shows one example of a two-level dynamic stabilization assembly 180 utilizing the components introduced in FIGS. 1A-1F. FIG. 1G shows how the components may be assembled and implanted in the spine of a patient to provide a multilevel dynamic stabilization assembly which provides dynamic stabilization of the spine and load sharing. Note that an identical or similar construct would preferably be implanted on the left side of the spine. Dynamic stabilization assembly 180 spans three vertebrae 181, 182 and 183 and thus two levels of the spine 181-182 and 182-183. Vertical rods 106a, 106b are connected to the levels. Each vertical rod is secured at one end to a deflection rod 104a, 104b by a ball joint 108a, 108b and at the other end to a bone anchor 191, 192 through a connector 170 or coaxial head 160. The dynamic stabilization assembly 180 provides controllable flexibility and load sharing at each level of the spine.

FIG. 1G shows three adjacent vertebrae 181, 182 and 183. Bone anchors 191, 192 and 193 have been implanted in each of the vertebrae 181, 182 and 183 on the right side of the spinous process 184 between the spinous process 184 and the transverse process 185. The threads 124 (not shown but see bone anchor 102 of FIGS. 1A-1E) have been fully implanted in the vertebrae 181, 182 and 183. In preferred procedures, the bone screw 120 is directed so that it is implanted within one of the pedicles 186 angled towards the vertebral body 187. As shown in FIG. 1G, the housing 130 of each bone anchor 102 remains partly or completely exposed above the surface of the vertebrae so that one or more of a connection system component and deflection system component can be secured to the bone anchor.

Referring again to FIG. 1G, a bone anchor 193 is implanted in vertebra 183. A deflection rod 104b is connected by a ball joint 108b to a first vertical rod 106b (see FIGS. 1A and 1B) and is installed in the housing 130c of bone anchor 193. Deflection rod 104b is secured within housing 130c of bone anchor 193 by tightening of locking set screw 136c. Vertical rod 106b is rotated about ball joint 108b to align vertical rod 106b towards bone anchor 192 implanted in vertebra 182. The free end of the vertical rod 106b is positioned in the aperture 178 of a connector 170 as shown in FIGS. 1E and 1F. Aperture 178 is aligned with vertical rod 106b by sliding clamp ring 172 up and down and rotating clamp ring 172 around the exterior surface 140b of housing 130b of bone anchor 192. When aperture 178 is properly aligned, screw 176 is tightened to secure connector 170 to housing 130b of bone anchor 192. Screw 177 is tightened to secure connector 170 to vertical rod 106b (see FIGS. 1E and 1F).

A second deflection rod 104a connected by a second ball joint 108a to a second vertical rod 106a is mounted in the cavity of the housing of the bone anchor 192. Second deflection rod 104a is secured within housing 130b of bone anchor 192 by tightening locking set screw 136b. Vertical rod 106a is rotated about ball joint 108a to align vertical rod 106a towards bone anchor 191 implanted in vertebra 181. The free end of the second vertical rod 106a is positioned in the aperture 168 of a coaxial head 160 (as shown in FIGS. 1C and 1D). Aperture 168 of coaxial head 160 is aligned with vertical rod 106a by rotating rod 162 within housing 130a and pivoting saddle 163 relative to yoke 164 around ball 165. When aperture 168 is properly aligned, locking set screw 136a is tightened to secure connector 160 to housing 130 of bone anchor 191. Locking set screw 167 is likewise tightened to secure coaxial head 160 to vertical rod 106a and lock together saddle 163 and yoke 164 in fixed relation to ball 165 (see FIGS. 1C and 1D).

It should be noted that dynamic stabilization assembly 180 does not require horizontal bars or locking screws thereby reducing the exposure of tissue and/or bone to foreign bodies compared to systems with this additional hardware. The dynamic stabilization assembly of FIG. 1G thereby has a small footprint, potentially reducing the amount of displacement of tissue and/or bone, reducing trauma to tissue and/or bone during surgery. Further, the smaller footprint can reduce the amount of tissue that needs to be exposed during implantation.

The particular dynamic stabilization assembly shown in FIG. 1G is provided by way of example only. It is an aspect of preferred embodiments of the present invention that a range of components be provided and that the components may be assembled in different combinations and organizations to create different assemblies suitable for the functional needs and anatomy of different patients. Also, deflection rods having different force deflection characteristics may be incorporated at different spinal levels in accordance with the anatomical and functional requirements. Dynamic stabilization may be provided at one or more motion segments and in some cases dynamic stabilization may be provided at one or more motion segments in conjunction with fusion at an adjacent motion segment. Particular dynamic stabilization assemblies may incorporate combinations of the bone anchors, vertical rods, deflection rods, offset and coaxial connectors described herein, in the related applications incorporated by reference, and standard spinal stabilization and/or fusion components, for example screws, rods and polyaxial screws.

Deflection Rods/Loading Rods

One feature of embodiments of the present invention is load sharing provided by embodiments, and, in particular, the deflection rod or loading rod of the embodiments. The soft tissues of the spine are no longer able to accommodate the loads exerted on the spine during normal spine motion since these spine tissues are either degenerated or damaged. The deflection rod provides stiffness and support where needed to support the loads exerted on the spine during normal spine motion thereby recovering improved spine function without sacrificing all motion.

In the embodiment shown in FIGS. 1A and 1B, the deflection rod 104 includes an inner rod, an outer sleeve, and a shield and deflection guide positioned about the sleeve. The shield and deflection guide can also be referred to as a shield and/or a deflection guide. The inner rod can be made of a super elastic material such as Nitinol, the outer sleeve can be made of a biocompatible polymer, e.g. PEEK, and the shield and deflection guide can be made of a bio-compatible material, for example, titanium. The shield and deflection guide is shaped to be inserted within the cavity of the housing portion of a bone anchor. (See, e.g. FIGS. 1A and 1B). The deflection system can be designed with different amounts of stiffness by selecting among different deflection rods. By selection of materials and dimensions, the deflection rods can be provided in a range from a highly rigid configuration to a very flexible configuration and still provide dynamic stability to the spine.

A deflection rod assembly of the deflection system can be conveniently mounted in the bone anchor after the bone anchor is implanted in the bone. Because the deflection rod is not pre-mounted to the bone anchor, the bone anchor can be implanted in the spine of a patient followed by the mounting of the deflection rods. Such an arrangement enhances the ease by which such a system can be implanted in a patient. By changing the configuration of the outer dimensions of shield and deflection guides as appropriate for other spine implant systems, the deflection rods of the deflection system can be conveniently mounted on a wide variety of spine implant systems and other bone implant systems and provide the novel attributes of the deflection rod assembly to that other system. Moreover, load sharing is enhanced by the ability to select the appropriate stiffness of the deflection rod or loading rod in order to match the load sharing characteristics desired. The stiffness of a dynamic stabilization assembly can be selected as needed for a particular patient. By selecting the appropriate stiffness of the deflection rod or loading rod to match the physiology of the patient and the loads that the patient places on the spine, a better outcome is realized for the patient.

Furthermore, each of the deflection rods in the dynamic stabilization assembly can have a different stiffness or rigidity or flexibility. Thus, in the same assembly, a first deflection rod can have a first flexibility or stiffness or rigidity, and a second deflection rod can have a second different flexibility or stiffness or rigidity depending on the needs of the patient. In an embodiment, deflection rods can have different deflection properties for each level and/or side of the dynamic stabilization assembly depending on the user's needs. In other words, one portion of a dynamic stabilization assembly may offer more resistance to movement than the other portion based on the design and selection of different deflection rods having different stiffness characteristics, if that configuration benefits the patient.

Figure 2A:
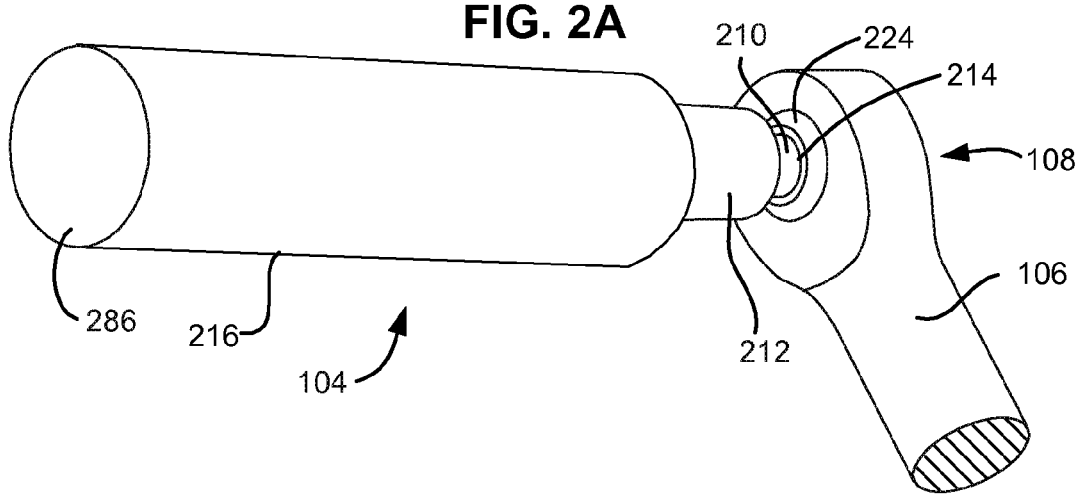
FIG. 2A is a perspective view of a deflection rod assembly in accordance with an embodiment of the present invention.

Referring now to FIG. 2A which shows an enlarged view of deflection rod 104 of FIGS. 1A-1B. Deflection rod 104 includes an inner rod 210 preferably made of, for example, a super elastic material e.g. Nitinol, and an outer shell 212 made of, for example, PEEK. These elements can be fit into a shield 216 to make up the deflection rod 104 of this embodiment. The free end 214 of the inner rod 210 is connected by a ball joint 108 to the end of vertical rod 106.

Figure 2B:
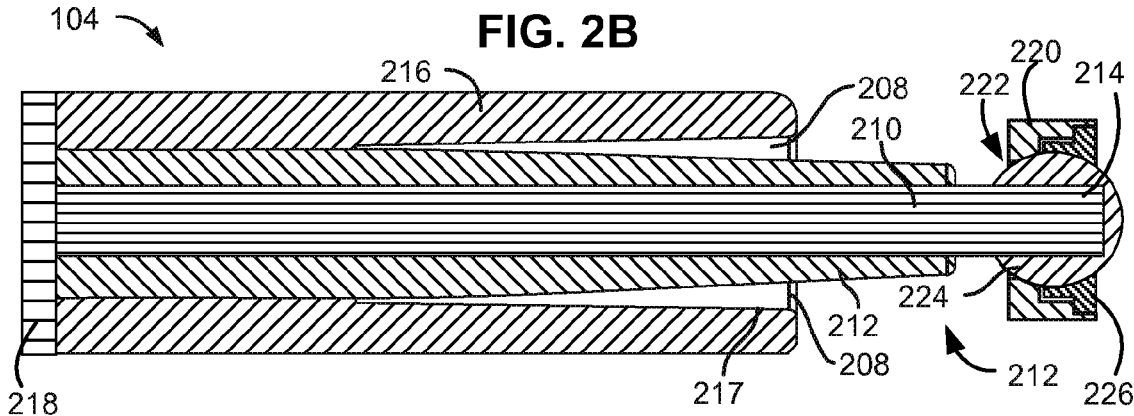
FIG. 2B is a sectional view of the deflection rod assembly of FIG. 2A.

Referring now to FIG. 2B, the connection between vertical rod 106 (shown in FIG. 2A) and inner rod 210 of deflection rod 104 is illustrated in greater detail. Vertical rod 106 includes disk-shaped housing 220 at one end. The free end 214 of the inner rod 210 is passed through an aperture 222 in disk-shaped housing 220 of the vertical rod 106. The diameter of the inner rod 210 is smaller than the diameter of the aperture 222. Once the free end 214 of the inner rod 210 is passed through the aperture 222, a ball 224 is attached to inner rod 210 using threading, fusing, gluing, press fit and/or laser welding techniques, for example. The diameter of the aperture 222 is less than the diameter of the ball 224 to prevent the ball 224 from passing back through the aperture 222. Once the ball 224 is positioned within the disk-shaped housing 220 of vertical rod 106, a retaining ring 226 is threaded, fused, glued, press fit and/or laser welded, for example, to free end 214 of the vertical rod 106, thereby securing the ball 224 to the vertical rod 106 in a ball joint connection 108 (as shown in FIG. 2A). In this configuration, the vertical rod 106 is allowed to rotate and/or have tilting and/or swiveling movements about a center which corresponds with the center of ball 224 of ball joint 108. Ball 224 can also be displaced relative to shield 216 by deflection of the free end 214 of inner rod 210.

Referring again to FIG. 2B, the inner rod 210 and outer shell 212 may be press fit into shield 216. The outer shell 212 may also have surface features to restrain the outer shell 212 from slipping out of the shield 216. For example, the outer shell may have ridges, barbs, threads or the like to engage the outer shell 212. Alternatively, a biocompatible adhesive may be used to bond the outer shell 212 to the shield 216. In some embodiments, a base 218 may be attached to inner rod 210 to prevent inner rod 210 from being pulled out of outer shell 212 and/or shield 216. The base 218 may be attached by laser welding, soldering or other bonding technology. For example, a base 218 in the form of a Nitinol disk may be laser welded to the base (distal end) 218 of a Nitinol inner rod 210. Alternatively, the base 218 may mechanically engage the inner rod 210 using, for example, threads. For example, a lock ring, toothed locking washer, cotter pin or other mechanical device can be used to secure inner rod 210 within shield 216.

As shown in FIG. 2B, the inner rod 210 of the deflection rod 104 is cylindrical and the outer shell 212 is tapered, and thus is configured to become gradually narrower going from the base 218 to the free end 214 of the inner rod 210. The inner surface 217 of the shield 216 in this embodiment forms a cone shape with a smaller diameter closer to base 218 (the distal end) and a larger diameter closer to the proximal end (adjacent the free end 214 of the inner rod 210). Thus, the inner rod 210 has a space 208 to flex from the shield/deflection guide 216. The inner surface 217 of the shield and deflection guide 216 of the deflection rod 104 serves as a guide for the inner rod 210 to effectively control and limit the deflection for the inner rod 210. Other shapes of inner rod 210, outer shell 212 and shield 216 may be used.

In a preferred embodiment of a deflection rod may have the following preferred dimensions:
Inner Nitinol rod having a diameter of about 0.080 inches;
Outer titanium shell having a major diameter of about 0.165 inches and the tapered portion tapers at about 2.5 degrees per side;
Shield and deflection guide having a housing diameter of about 0.265 inches;

Deflection rod is secured to the deflection guide along a length of about 0.200 inches from the end of the deflection rod;

The deflection rod has a working length from the end of the system to the center of the ball joint of about 1.040 less the press fit length of about 0.200 which is length of about 0.840;

The overall length of the deflection rod is about 1.100 inches;

The spherical ball in the ball and socket joint that secures the vertical rod to the deflection rod has a diameter of about 0.188 inches; and The vertical rod has a diameter of about 0.150 inches. The dimensions can be varied substantially to achieve the characteristics desired in particular circumstances.

With the configuration shown in FIG. 2B, portions of inner rod 210 can deflect until the outer shell 212 of that portion comes in contact with the inner surface 217 of the shield 216. Successive portions of the inner rod 210 closer to the free end 214 can still deflect until successive portions of outer shell 212 come into contact with the inner surface 217 of the shield 216. Accordingly, the conical shape of the inner surface 217 of the shield 216 provides a deflection guide 216 which controls the amount and location of deflection of the inner rod 210 along the inner rod 210 from the base (fixed end) 218 of the inner rod 210 to the free end 214 of the inner rod 210, where the inner rod extends past shield 216. The shape of the outer shell 212 and the inner surface 217 of the shield and deflection guide thereby define the range of motion and the stiffness which are characteristic of the deflection rod. By changing the shape of the outer shell 212 and the inner surface 217 of the shield 216 these characteristics can be changed.

By changing the rate of change of the diameters and/or the diameters of the outer shell and the inner surface of the shield and deflection guide, these characteristics can be changed. Thus, the stiffness of components of the deflection rod can be, for example, increased by increasing the diameter of the outer shell and/or by decreasing the diameter of the inner surface of the shield and deflection guide as both approach where the inner rod extends from the outer shell. Additionally, increasing the diameter of the inner rod will increase the stiffness of the deflection rod while decreasing the diameter of the inner rod will decrease the stiffness of the deflection rod. The taper of the inner surface of the shield and deflection guide can be configured to approach the natural dynamic motion of the spine, while giving dynamic support to the spine in that region. In addition to changing the dimensions, changing the materials which comprise the components of the deflection rod can also affect the stiffness and range of motion of the deflection rod. For example, making the inner rod out of titanium or steel would provide for more stiffness than making, for example, the inner rod out of Nitinol. Further, making the outer shell out of a material that is stiffer than PEEK would provide for a stiffer outer shell.

Figure 2C:
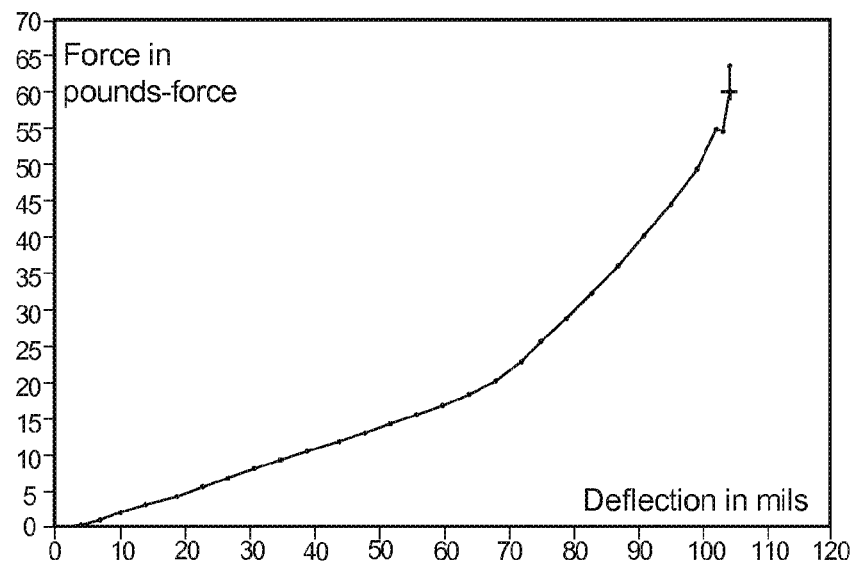
FIG. 2C is a graph showing a deflection/force curve for the deflection rod assembly of FIG. 2A.

FIG. 2C is a graph showing one preferred deflection of the inner rod and outer shell in accordance with a deflection force on the inner rod where the vertical rod is connected to the inner rod. The deflection rod tested to generate the force/deflection curve shown in FIG. 2C has a PEEK outer shell having a diameter of is about 0.165 inches at its largest diameter and an inner rod made of Nitinol of 0.080 inches in diameter. The working length of the deflection rod was about 1.04 inches. FIG. 2C provides an example of a specific amount of deflection in response to a given load on the spine and the deflection rod. The load/deflection g curve of FIG. 2C demonstrates that the deflection rod tested responds more stiffly as the load increases.

The force/deflection curve of a deflection rod can be customized based on the choice of dimensions and materials. It is contemplated, for example, that the deflection rod can be made in stiffness that can replicate a 70% range of motion and flexibility of the natural intact spine, a 50% range of motion and flexibility of the natural intact spine and a 30% range of motion and flexibility of the natural intact spine for providing in a kit for a doctor to use.

The graph of FIG. 2C depicts a deflection rod that is a little stiffer than a 70% stiffness deflection rod. As is evident from FIG. 2C, the deflection/force curve is non-linear. As the deflection increases, the stiffness of the deflection rod increases such that the force required per unit of additional deflection increases rapidly in response to the load placed on the spine and deflection rod. As depicted in FIG. 2C, as load or force is first applied to the deflection rod by the spine, the deflection of the deflection rod responds about linearly to the increase in the load. After about 0.060 inches of deflection, the deflection rod responds in a non-linear manner. In this region, a greater amount of load or force needs to be placed on the deflection rod in order to obtain the same amount of deflection that was realized prior to this point. Further, the rate of change in the amount of deflection based on the force applied can also be a non-linear function. Accordingly, the deflection rod of this example offers dynamic stabilization by providing a range of motion where the load supported increases about linearly as the deflection increases and then with increased deflection the load supported increases more rapidly in a non-linear manner in order to provide dynamic stabilization.

The deflection system of the present invention provides, in some embodiments, the ability to control stiffness for extension, flexion, lateral bending and axial rotation, and to control stiffness for each of these motions independently of the other motions. The characteristics of the deflection rods can be changed by, for example, adjusting the inner surface 217 of the shield and deflection guide 216 and these characteristics need not be symmetric. For example, as shown in FIG. 2D, a bias can be introduced in the deflection rod 104 by having the inner surface 217 vary asymmetrically relative to the outer shell 212 and inner rod 210. As shown in FIG. 2D, the inner surface 217 of shield 216 is designed such that gap 208a on the upper side is larger than gap 208b on the lower side. Thus, inner rod 210 and the outer shell 212 may deflect more in the direction of gap 208a than in the direction of gap 208b. In embodiments where the deflection rod 104 has different force-deflection response in different directions, it is important to ensure that the deflection rod 104 is implanted in the correct orientation. The deflection rod 104 is therefore provided with discernable visual or physical characteristics (e.g. an arrow, color, indentation or other observable indicator) which guide the surgeon to the correct orientation of implantation.

Varying the shape of the inner surface 217 of shield 216 is one way to control stiffness for extension, flexion, lateral bending and axial rotation independently. For example, if the upper portion of the inner surface 217 is more distantly spaced from the outer shell 212 than the lower portion of the inner surface 217, deflection rod 104 can deflect more when the spine is placed in flexion and can deflect less when the spine is placed in extension. In effect, this arrangement is more restrictive with respect to movement of the spine with the spine in extension and less restrictive with respect to the movement of the spine with the spine in flexion. Conversely, if the lower portion of the inner surface 217 is more distantly spaced from the outer shell 212 than the upper portion of the inner surface 217, the deflection rod 104 can deflect more when the spine is placed in extension and can deflect less when the spine is placed in flexion. In effect, this arrangement is more restrictive with respect to movement of the spine in flexion and less restrictive with respect to the movement of the spine in extension.

An alternative way to control stiffness for extension, flexion, lateral bending and axial rotation independently is to vary the thickness and/or flexibility of the material of the outer shell 212. Accordingly, certain embodiments of the present invention can vary the stiffness and selectively vary the orientation and direction that the stiffness is felt by varying the structure of the implantation system of the invention. Further, in the deflection response and flexibility and motion of a left deflection rod can be different from that of a right mounted deflection rod in the disclosed embodiments.

FIG. 2E shows an alternative embodiment of a deflection rod 204 for use with a different design of bone anchor 202. The embodiment of FIG. 2E illustrates a different mechanism for securing the deflection rod 204 to the bone anchor 202. In this embodiment the housing 230 of bone anchor 202 has a coupling in the form of a groove 238 around the proximal end of housing 230. Deflection rod 204 has a collar 240 attached to the proximal end of the shield 246. The collar 240 may be formed in one piece with the deflection shield 246. A threaded aperture 241 passes through collar 240. A screw 242 is fitted in threaded aperture 224. When the deflection rod 204 is properly seated with housing 230 of bone anchor 202, screw 242 may be tightened so that it engages the groove 238 around the proximal end of housing 230 of bone anchor 202. Collar 240 seats against the proximal end of bone anchor 202. Screw 242 can be tightened to a first level where it engages groove 238 sufficiently to prevent removal of deflection rod 204 while still allowing rotation of deflection rod 204 within housing 230. Subsequently, screw 242 may be further tightened to completely secure deflection rod 204 to housing 230 and prevent any further movement of shield 246 relative to cavity 235. The same coupling system may be added to other components, e.g. the coaxial head 160 of FIGS. 1C and 1D, to secure the components to the bone anchor 202.

FIG. 2E also demonstrates some alternative features of bone anchor 202. For example, the cavity 235 of housing 230 contains structural features 231 within the housing which allow a driver to be inserted to drive the bone anchor 202 into the bone before installation of the deflection rod 204. It should also be noted that in bone anchor 202, the threaded section extends partly over the housing 230. Put another way, the cavity into which deflection rod 204 is received, extends into the threaded region of bone anchor 202. This is advantageous in that ball 224 is thereby lowered closer to the surface of the vertebra into which bone anchor 202 is installed. Note, also, that the threads in the region covering the housing (the proximal end of the threaded region) are finer in pitch than the threads near the tip of the bone anchor (the distal end). This is because the proximal threads are designed to engage the harder compact bone at the surface of the vertebra. The coarser threads are better for engaging the spongy cancellous bone interior to the vertebra.

FIG. 2F shows an alternate view of the deflection rod 204 of FIG. 2E. FIG. 2F shows, in addition, a vertical rod 248 attached to ball 224 of deflection rod 204 to form a ball joint 249. Vertical rod 248 can pivot about ball joint 249 with three degrees of freedom. Vertical rod 248 can rotate around the longitudinal axis of deflection rod 204 as shown by arrow 280. Vertical rod 248 can pivot about an axis perpendicular to the axis of deflection rod 204 and the vertical rod 248 as shown by arrow 282. Vertical rod 248 may also rotate around the long axis of vertical rod 204 as shown by arrow 284. Where vertical rod 248 is straight (as shown by dotted line), rotation of vertical rod 248 about its long axis has no effect on the position and orientation of the free end 286 of vertical rod 248. However, in some cases it may be useful to put a bend 247 in the vertical rod 248. Bend 247 may be from 1 to 90 degrees but is preferably less than 45 degrees and more preferably less than 15 degrees. With bend 247 in vertical rod 248, rotation of vertical rod 248 about its long axis where it meets ball joint 249 changes the orientation and position of free end 286 of vertical rod 248. The change in orientation of free end 286 of vertical rod 248 can be used to facilitate alignment of free end 286 of vertical rod 248 with an offset connector (shown in FIG. 1E) or coaxial head and thereby facilitate assembly of a dynamic stabilization assembly.

Figure 2G:
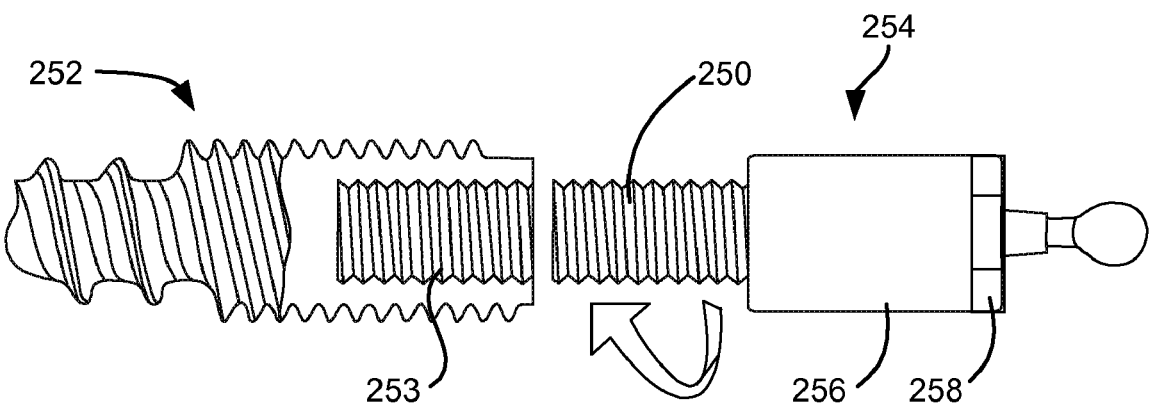
FIG. 2G is a perspective view of an alternative deflection rod assembly and bone anchor in accordance with an embodiment of the present invention.

FIG. 2G illustrates another mechanism for connecting a deflection rod 254 to a bone anchor 252. As illustrated in FIG. 2G, deflection rod 254 is provided with a threaded region 250 which mates with a threaded cavity 253 in the proximal end of bone anchor 252. After implantation of bone anchor 252 into a vertebra, the threaded portion 250 of deflection rod 254 is installed in the threaded cavity 253 and tightened to secure the deflection rod 254 to the bone anchor 252. Note also, that the external surface 256 of the deflection rod 254 is a surface to which an offset connector may be mounted (e.g. connector 170 of FIG. 1E). The deflection rod 254 also has surface features 258 (for example a bolt head pattern) so that it may be engaged by a driver to tighten deflection rod 254 to bone anchor 252. Additionally, locking features may be provided to lock the deflection rod 254 to bone anchor 252. Other methods and devices may be used to fasten the deflection rod into the cavity of the bone anchor including, for example, cotter pins, cams, interference fittings, press fitting, clips, tabs, adhesives, welding, screws, bayonet fittings, and other mechanical interference fittings. In preferred embodiments, the fastener or fastening method is reversible so that the deflection rod may be removed and or exchanged, if necessary or desired, without removing the bone anchor.

Figure 2H:
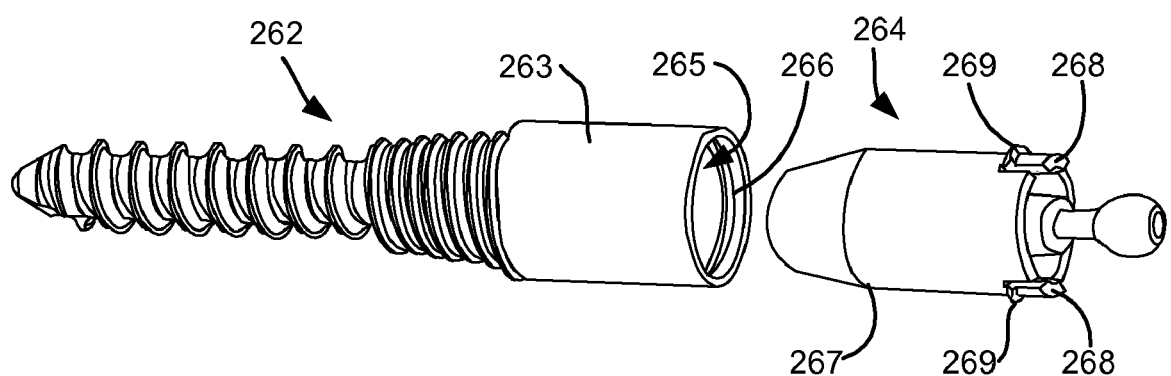
FIG. 2H is a perspective view of an alternative deflection rod assembly and bone anchor in accordance with an embodiment of the present invention.

FIG. 2H shows another alternative mechanism for connecting a deflection rod 264 to a bone anchor 262. Housing 263 of bone anchor 262 includes a coaxial cavity 265 to accommodate deflection rod 264. Cavity 265 has a coupling comprising a groove 266 inside the cavity adjacent the proximal end of cavity 265. The shield 267 of deflection rod 264 includes two tabs 268 each carrying a protrusion 269 for engaging the groove 266 within cavity 265. The protrusions 269 are ramped so that the tabs 268 deflect inwards as deflection rod 264 is inserted into cavity 265. When deflection rod 264 is properly located in cavity 265, tabs 268 spring outwards so that protrusions 269 engage groove 266 and then oppose withdrawing deflection rod 264 from cavity 265. However, if it desired to remove deflection rod 264, a tool may be used to push tabs 268 towards one another thereby releasing the protrusions 269 from the groove 266 and permitting removal of deflection rod 264. Offset connectors may be mounted to the outside surface of housing 263. Alternative coaxial connectors/heads may be mounted within cavity 266 using the same mechanical features as deflection rod 264.

Figure 2I:
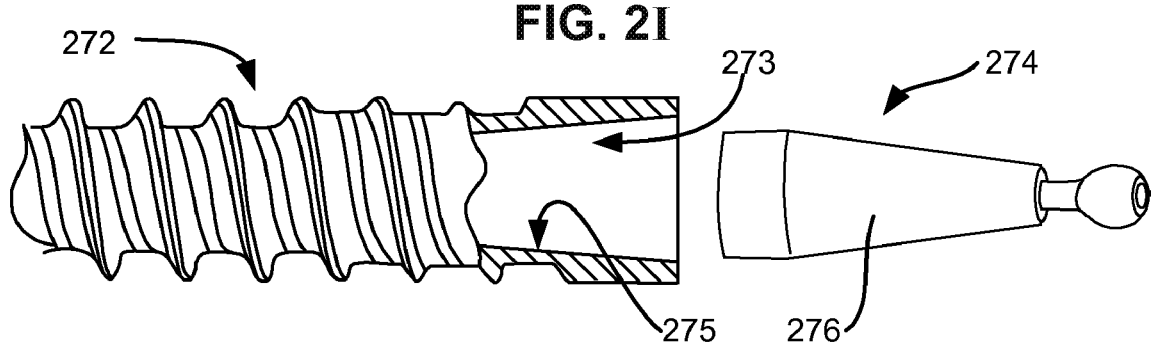
FIG. 2I is a perspective view of an alternative deflection rod assembly in accordance with an embodiment of the present invention.

FIG. 2I illustrates another alternative embodiment in which a bone anchor 272 has a cavity 273 for receiving a deflection rod 274. In this embodiment, deflection rod 274 has no guide/shield element. However, a guide surface 275 is formed by the sides of cavity 273 of the bone anchor 272. The deflection rod 274 can be mated with the cavity 273 and guide surface 275 applying similar techniques to mate the components of previously described embodiments. The guide surface controls and limits deflection of deflection rod 274 in the same way as previously described for the guide surface of a shield. Thus, in this embodiment, the geometry of the outer shell 276 of deflection rod 274 and the guide surface 275 can be configured to provide the desired performance characteristics (in combination with the materials and dimensions of the deflection rod 274). Forming the guide surface 275 in the bone anchor 272 can potentially reduce a thickness otherwise required to accommodate a separate shield element.

Versatile Offset Connectors/Heads

As described above, connector 170 of FIG. 1E has 3 degrees of freedom ("DOF") with respect to the position and orientation of a rod. While these degrees of freedom may be sufficient in some situations, they may not be sufficient in other situations. Thus, it is desirable to have a range of different connectors which are all compatible with the anchor system and deflection system. The connectors may have different attributes, including for example, different degrees of freedom, range of motion, and amount of offset, which attributes may be more or less appropriate for a particular relative orientation and position of two bone anchors and/or patient anatomy. It is desirable that each connector be sufficiently versatile to connect a rod to a bone anchor in a range of positions and orientations while being simple for the surgeon to adjust and secure. It is desirable to provide a set of connectors which allows the dynamic stabilization system to be assembled in a manner that adapts a particular dynamic stabilization assembly to the patient anatomy rather than adapting the patient anatomy for implantation of the assembly (such as by removing tissue\bone to accommodate the system). In a preferred embodiment, the set of connectors comprising the connection system have sufficient flexibility to allow the dynamic stabilization system to realize a suitable dynamic stabilization assembly in all situations that will be encountered within the defined patient population FIGS. 3A-3F show an embodiment of in-line connector 300 for connecting a bone anchor to a vertical rod with more degrees of freedom than the connector of FIG. 1E. In-line connector 300 mounts externally of the housing of a bone anchor and is thus an example of an offset head/connector. In-line connector 300 comprises six components and allows for two degrees of freedom of orientation and two degrees of freedom of position in connecting a vertical rod to a bone anchor. FIG. 3A shows an exploded view of the in-line connector 300 revealing the components. The six components of in-line connector are dowel pin 302, pivot pin 304, locking set screw 306, clamp ring 310, saddle 320 and plunger 330.

Clamp ring 310 comprises a ring 311 with a gap 312. Clamp ring 310 is sized such that it can slide freely up and down the housing of a bone anchor and rotate around the housing when the ring 311 is relaxed. However when the gap 312 is forced closed, the clamp ring 310 grips the housing and prevents the clamp from moving in any direction. On each side of gap 312 is an ear 314. Each ear 314 terminates in a cylindrical surface 316 having an aperture 318. The ears 314 are inserted into a lower clevis 321 of saddle 320.

Saddle 320 is generally cylindrical with bore 326 along the longitudinal axis. Saddle 320 includes a lower clevis 321 and an upper clevis 323. Bore 326 communicates between the upper clevis 323 and lower clevis 321. The lower clevis 321 is sized to receive ears 314 of clamp ring 310 through the side of clevis 321. The lower clevis 321 also has a pair of apertures 322 for receiving pivot pin 304. Pivot pin 304 passes through apertures 322 and also through apertures 318 of clamp ring 310 thereby securing clamp ring 310 into lower clevis 321. Note that the apertures 318 of clamp ring 310 are slightly larger than the diameter of pivot pin 304 so that ears 314 have a small range of travel about pivot pin 304 in addition to being able to rotate around pivot pin 304 over a range of about 180 degrees. Thus, even with pivot pin 304 in position, ears 314 have some vertical range of travel within the lower clevis 321 of saddle 320.

Plunger 330 is received into a bore 326 in saddle 320 which communicates between the upper clevis 323 and lower clevis 321. Bore 326 is shown in FIG. 3B which presents an alternate view of saddle 320. Referring again to FIG. 3A, the lower surface 332 of plunger 330 is concave with the same curvature as the cylindrical surface 316 of ears 314 of clamp ring 310. When installed through the bore 326 in saddle 320, the lower surface 332 of plunger 330 rests on the cylindrical surface 316 of ears 314. The upper surface 334 of plunger 330 protrudes into the slot 324 of the upper clevis 323 of the saddle 320. Plunger 330 also has a notch 336 in the upper surface. Notch 336 is positioned so that it can be engaged by dowel pin 302 when dowel pin 302 is inserted through aperture 327 or saddle 320. Plunger 330 is thereby captured within bore 326 of saddle 320 but has a range of travel up and down bore 326.

The slot 324 of the upper clevis 323 of saddle 320 is sized to receive a rod which may be a vertical rod e.g. vertical rod 106 of FIG. 1A. Slot 324 is threaded adjacent the open end of slot 324 and configured to engage set screw 306. FIG. 3C, shows a perspective view of connector 300 after assembly of the six components.

FIGS. 3D and 3E illustrate the clamping action of connector 300. As shown in FIG. 3D, when assembled, with set screw 306, connector 300 defines an aperture 308 for receiving a rod 338 (shown in section). Aperture 308 is bordered on the upper side by the lower surface 309 of set screw 306, on the lower side by the upper surface 334 of plunger 330; and on each side by the sides of slot 324. As shown in FIG. 3E, when set screw 306 is tightened against a rod 338 within aperture 308 of connector 300, the rod 338 pushes down on the upper surface 334 of plunger 330. Plunger 330 slides within bore 326 of saddle 320. The lower surface 332 of plunger 330 pushes down upon the cylindrical surface 316 of ears 314 of clamp ring 310. The ears 314 of clamp ring 310 are, in turn, forced against a pair of ramps 328 at the end of lower clevis 321 of saddle 320. Ramps 328 force ears 314 together securing clamp ring 310 to the housing of a bone anchor. In this way, operation of the single set screw 306 serves to lock the clamp ring 310 to the housing of the bone anchor, fix saddle 320 in a fixed position relative to clamp ring 310 and secure a rod 338 within the aperture 308 of connector 300.

As shown in FIG. 3F, connector 300 provides four degrees of freedom with respect to rod placement. Connector 300 provides two linear degrees of freedom. First, clamp ring 310 can slide up and down the housing of the bone anchor within the range of travel provided by the housing surface as shown by arrow 340. Second, the rod can slide in and out of the aperture 308 of connector 300 as shown by arrow 342. Connector 300 also provides two angular degrees of freedom. First, clamp ring 310 can rotate around the axis of the housing of a bone anchor as shown by arrow 344. Second, the saddle 320 of connector 300 can pivot about the axis of pivot pin 304 as shown by arrow 346. This axis is orthogonal to the axis of the bone anchor. The four degrees of freedom provide sufficient degrees of freedom to connect a vertical rod from one bone anchor to another bone anchor (so long as the linear and angular displacement is within range.

The in-line connector of FIGS. 3A-3F may be used to construct a dynamic stabilization assembly for one or more levels of the spine of a patient. FIG. 3G shows one example of a two-level dynamic stabilization assembly 380 utilizing the in-line connector introduced in FIGS. 3A-3F. FIG. 3G shows how the components may be assembled and implanted in the spine of a patient to provide a multilevel dynamic stabilization assembly which provides dynamic stabilization of the spine and load sharing. Note that an identical or similar construct would preferably be implanted on the left side of the spine. Dynamic stabilization assembly 380 spans three vertebrae 181, 182 and 183 and thus two levels of the spine 181-182 and 182-183. A vertical rod 106a or 106b is connected across each of the levels. Each vertical rod is secured at one end to a deflection rod 104a or 104b by a ball joint 108a or 108b and at the other end to a bone anchor 202a, 202b or 202c through a connector. The deflection rod provides controllable flexibility and load sharing at each level of the spine.

Figure 3G:
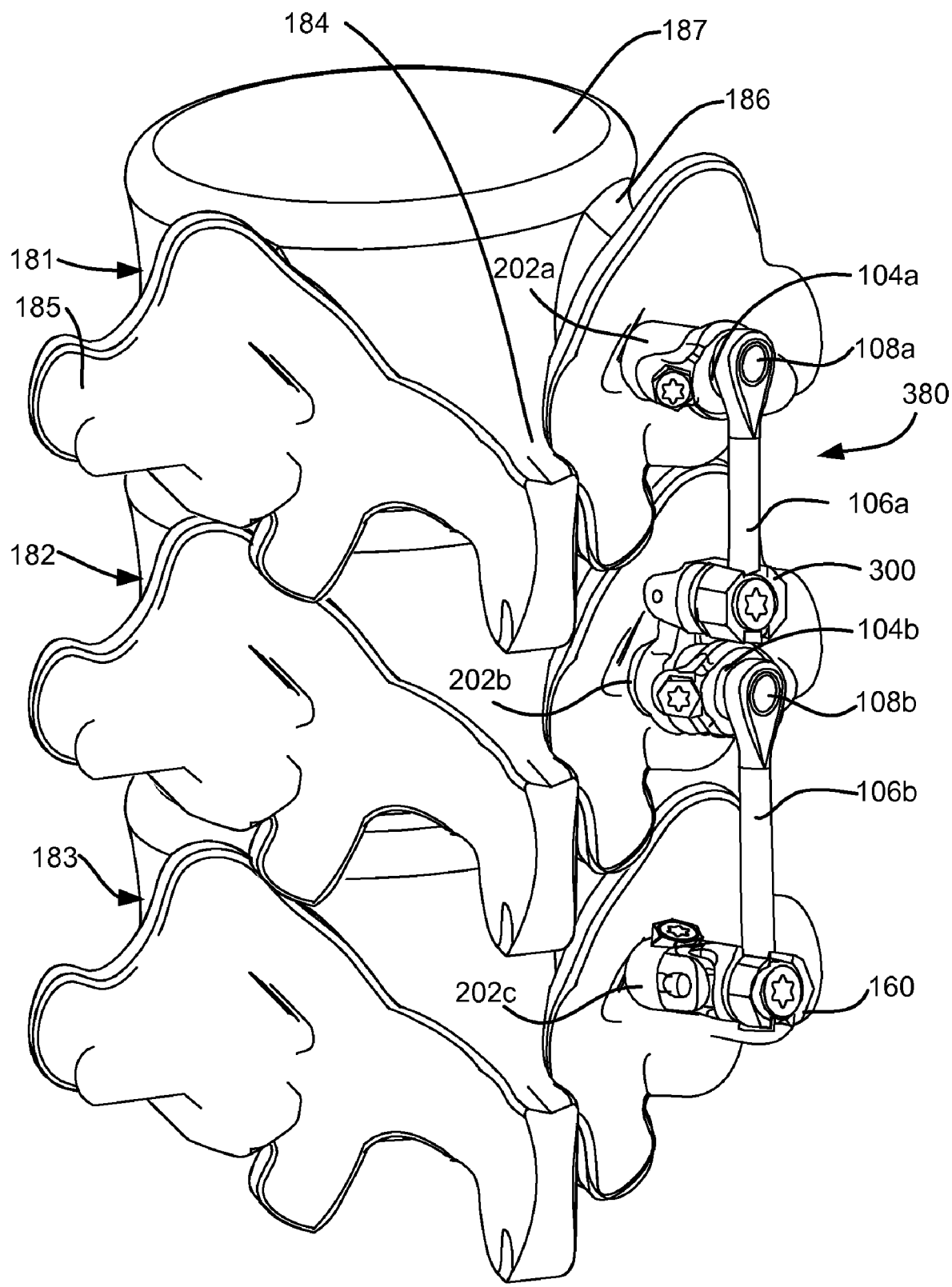
FIG. 3G is a posterior view of a multi-level dynamic stabilization assembly utilizing the polyaxial connector of FIGS. 3A to 3F in accordance with an embodiment of the present invention.
Figure 3H:
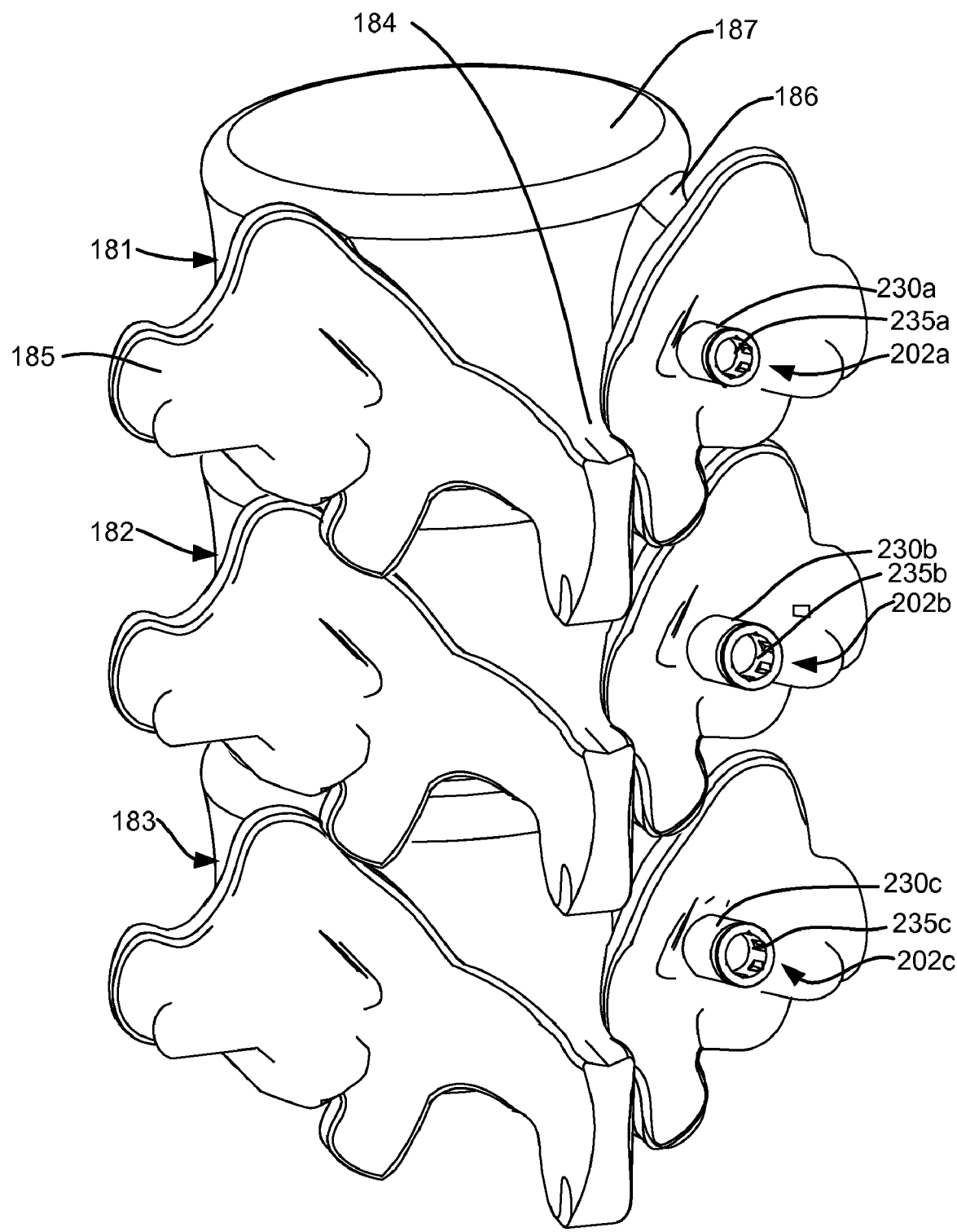
FIG. 3H is a posterior view of the anchor system components of the dynamic stabilization assembly of FIG. 3G.

Referring to FIG. 3H, which shows three adjacent vertebrae 181, 182 and 183. As a preliminary step, bone anchors 202a, 202b and 202c have been implanted in the vertebrae 181, 182 and 183 on the right side of the spinous process 184 between the spinous process 184 and the transverse process. A driver is inserted into the cavity 235a, 235b, 235c in order to drive the threaded portion of each bone anchor into the bone. The threaded region of each bone anchor is fully implanted in the vertebrae 181, 182 and 183. In preferred procedures, the bone anchor is directed so that the threaded portion is implanted within one of the pedicles 186 angled towards the vertebral body 187. As shown in FIG. 3H, the housing 230a, 230b, 230c of each bone anchor remains partly or completely exposed above the surface of the vertebrae so that one or more of a connection system component and deflection rod component could be secured to each bone anchor 202a, 202b and 202c. Coaxial components may be coaxially mounted inside each of cavities 235a, 235b, and 235c. Offset heads/connectors may also be externally-mounted to the outside surface of each of housings 230a, 230b and 230c.

Referring again to FIG. 3G, a coaxial head 160 is installed in bone anchor 202c. An in-line connector 300 is mounted externally to the housing of bone anchor 202b. A deflection rod 104a is coaxially mounted in the housing of bone anchor 202a. A deflection rod 104b is coaxially mounted in the housing of bone anchor 202b. A vertical rod 106a connects vertebra 202a and vertebra 202b. Vertical rod 106a is connected at one end to deflection rod 104a by ball joint 108a. Vertical rod 106a is connected at the other end by in-line connector 300 to bone anchor 202b. A second vertical rod 106b connects vertebra 202b and vertebra 202c. Vertical rod 106b is connected at one end to deflection rod 104b by ball joint 108b. Vertical rod 106b is connected at the other end by coaxial head 160 to bone anchor 202c.

The dynamic stabilization assembly 380 of FIG. 3G thus has a vertical rod 106a, 106b stabilizing each spinal level (202a-202b and 202b-202c). Each of the vertical rods 106a, 106b is secured rigidly at one end to a bone anchor (202b, 202c). Each of the vertical rods 106a, 106b is secured at the other end by a ball joint 108a, 108b to a deflection rod 104a, 104b thereby allowing for some movement and load sharing by the dynamic stabilization assembly. Connector 300 and coaxial head 160 permit assembly of dynamic stabilization assembly 380 for a wide range of different patient anatomies and/or placement of bone anchors 202a, 202b and 202c.

Figure 4G:
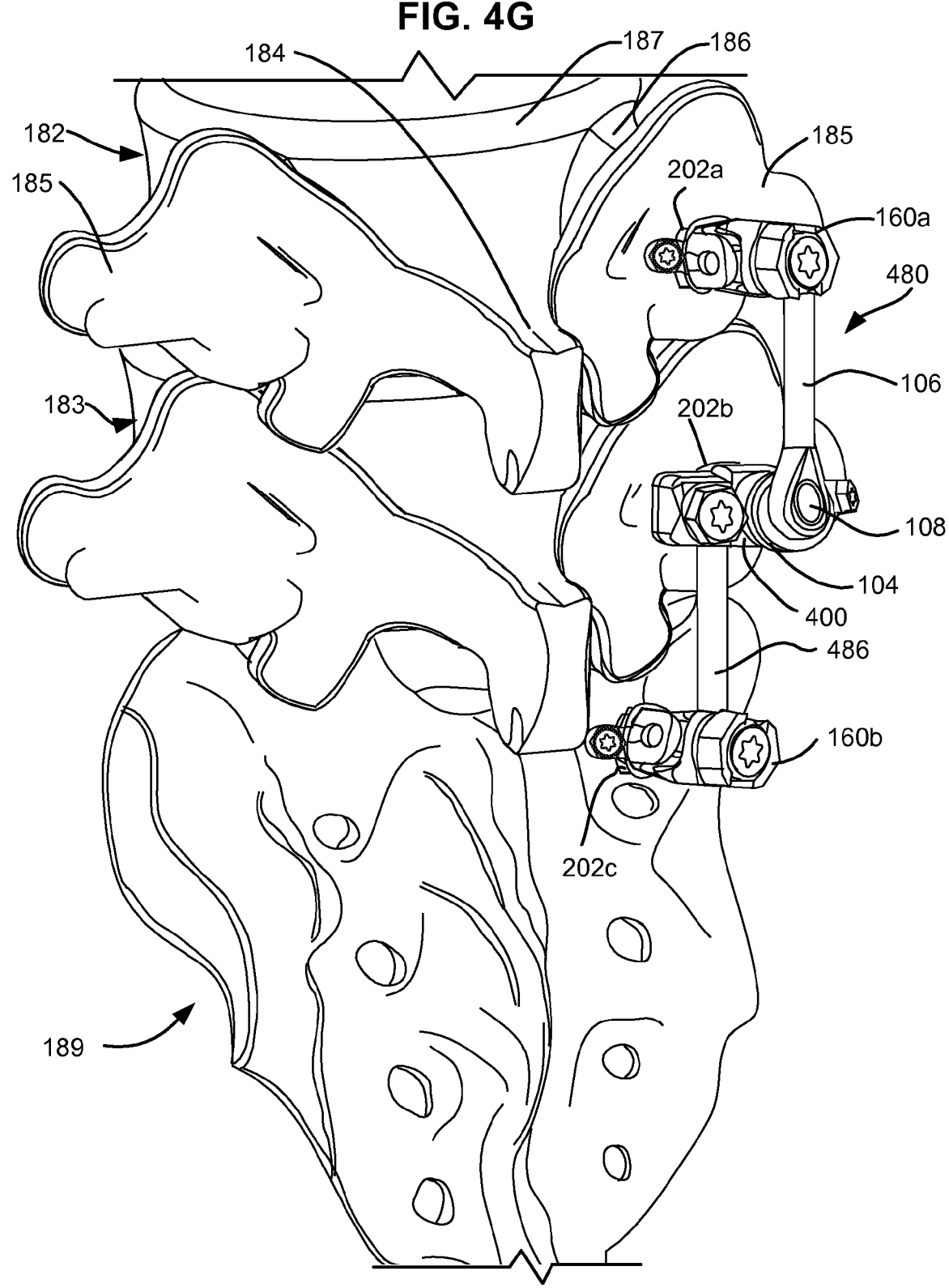
FIG. 4G is a posterior view of a multi-level dynamic stabilization assembly utilizing the polyaxial connector of FIGS. 4A to 4E in accordance with an embodiment of the present invention.

FIGS. 4A-4G show a side-swivel connector 400 for connecting a bone anchor to a vertical rod with more degrees of freedom than the connector of FIG. 1E. Side-swivel connector 400 mounts externally to the housing of a bone anchor and is thus an example of an offset head/connector. Side-swivel connector 400 comprises five components and allows for two linear degrees of freedom and two angular degrees of freedom in connecting a vertical rod to a bone anchor. FIG. 4A shows an exploded view of the side-swivel connector 400 revealing the components. The five components of side-swivel connector are snap ring 402, locking screw 406, clamp ring 410, swivel 420 and plunger 430.

Clamp ring 410 comprises a ring with a bore 412. Clamp ring 410 is sized such that it can slide freely up and down the housing of a bone anchor and rotate around the housing before the clamp is locked. However, when the plunger 430 is pushed through bore 412, the clamp ring 410 grips the housing and prevents the clamp 410 from moving in any direction. On one side of clamp ring 410 is a cylindrical extension 414. Bore 412 passes through the middle of cylindrical extension 414. Cylindrical extension 414 has a groove 418 on its outer surface. The groove 418 is sized so that snap ring 402 fits entirely within the groove 418 when snap ring 402 is compressed.

The first end 432 of plunger 430 is inserted into bore 412 of clamp ring 410. Plunger 430 has a lip 436 at its second end 434 so that it cannot fall entirely through bore 412. Snap ring 402 is expanded slightly and pushed over cylindrical extension 414 of clamp ring 410 until snap ring 402 snaps into groove 418 of cylindrical extension 414.

As shown in FIG. 4C, swivel 420 has an aperture 421 for receiving tubular extension 414 of clamp ring 410. Aperture 421 has a groove 422 sized to engages snap ring 402. Snap ring 402 is compressed as tubular extension 414 is inserted into aperture 421. However, when tubular extension is inserted the correct distance into aperture 421, groove 418 becomes aligned with groove 422 and snap ring 402 can expand into groove 422. When snap ring 402 has expanded into groove 422 a portion of snap ring 402 remains within each of grooves 422 and 418. Cylindrical extension 414 is thus locked into aperture 421 of swivel 420. Cylindrical extension 414 can, however, rotate within aperture 421. Furthermore, plunger 430 may still slide somewhat in and out of bore 412 of clamp ring 410. Swivel 420 has a channel 424 for receiving a vertical rod. The aperture 421 intersects channel 424. Second end 434 of plunger 430 protrudes slightly into the channel 424 when assembled. However, a lip 425 on bore 412 prevents plunger 430 from slipping too far into channel 424. Swivel 420 also has a threaded aperture 428 sized to fit locking screw 406. FIG. 4B, shows a perspective view of connector 400 after assembly of the six components.

FIGS. 4D and 4E illustrate the clamping action of connector 400 to clamp a rod 438 to the housing 439 of a bone anchor. As shown in FIG. 4D, connector 400 has a channel 424 for receiving a rod 438 (shown in section). As shown in FIG. 4D, locking screw 406 protrudes into one side of channel 424 and plunger 430 protrudes into another portion of the channel 424. Clamp ring 410 receives the housing 439 (shown by dashed lines) of a bone anchor and has enough room that clamp ring 410 may slide up and down on housing 439 and rotate around housing 439.

As shown in FIG. 4E, when set screw 406 is tightened against a rod 438 within channel 424 of connector 400, the set screw pushes rod 438 against a ramp 428 at the opposite side of channel 424 from locking screw 406. Ramp 428 pushes rod 438 against plunger 430. Plunger 430 is forced by rod 438 through bore 412 in clamp ring 410. The first end 432 of plunger 430 is thereby forced against the side of the housing 439 of the bone anchor preventing further movement of the housing 439 relative to clamp ring 410. The force of plunger 430 against housing 439 also applies force between grooves 418 and 422 (see FIGS. 4A and 4C) and locking ring 402 which serves to prevent further rotation of swivel 420 relative to clamp ring 410. In this way, operation of the single set screw 406 serves to lock the clamp ring 410 to the housing 439 of the bone anchor, and fix swivel 420 in a fixed position relative to clamp ring 410 and secure rod 438 within the channel 424 of connector 400.

As shown in FIG. 4F, side-swivel connector 400 provides four degrees of freedom with respect to rod placement. Connector 400 provides two linear degrees of freedom. First, clamp ring 410 can slide up and down the housing of the bone anchor within the range of travel provided by the housing surface as shown by arrow 440. Second, the rod can slide in and out of the channel 424 of connector 400 as shown by arrow 442. These linear degrees of freedom are not necessarily orthogonal because the angle between the channel 424 and the axis of the clamp ring 410 is variable. However, during typical operation, the axis of channel 424 and clamp ring 410 will be approximately perpendicular and thus the degrees of freedom are relatively independent. Connector 400 also provides two angular degrees of freedom. First, clamp ring 410 can rotate around the axis of the housing of a bone anchor as shown by arrow 444. Second, the swivel 420 of connector 400 can pivot about the axis of the tubular extension 414 (see FIG. 4A) of the clamp ring 410. This axis is orthogonal to the axis of the bone anchor. The four degrees of freedom provide sufficient degrees of freedom to connect a vertical rod from one bone anchor to another bone anchor (so long as the linear and angular displacement is within range).

The side-swivel connector of FIGS. 4A-4F may be used to construct a dynamic stabilization assembly for one or more levels of the spine of a patient. FIG. 4G shows one example of a two-level dynamic stabilization assembly 480 utilizing the side-swivel connector of FIGS. 4A-4F. FIG. 4G shows how the components may be assembled and implanted in the spine of a patient to provide a multilevel dynamic stabilization assembly which provides dynamic stabilization of the spine and load sharing. Note that an identical or similar construct would preferably be implanted on the left side of the spine. Dynamic stabilization assembly 480 spans two vertebrae 182 (L4) and 183 (L5) and the sacrum 189 (S1) thus two levels of the spine (L4-L5 and L5-S1 ). A vertical rod 106 connected across the L4-L5 levels. Vertical rod 106 is secured at one end to a deflection rod 104 by a ball joint 108 and at the other end to a bone anchor 202a through a connector 160a. The deflection rod provides controllable flexibility and load sharing at the L4-L5 level of the spine. Vertical rod 486 connects the L5-S1 level. Vertical rod 486 is secured at one end to bone anchor 202b by a side-swivel connector 400. Vertical rod 486 is secured at the other end to bone anchor 202c by a coaxial head 160b. There is no deflection rod at this level—this system is designed to hold the sacrum and L5 vertebra in fixed relationship to each other—possibly in conjunction with a fusion of the vertebra and sacrum.

Bone anchors 202a, 202b are implanted in vertebrae 182 and 183 on the right side of the spinous process 184 between the spinous process 184 and the transverse process 185. Bone anchor 202c is implanted in the sacrum transverse of the sacral crest and superior of the first sacral foramina. The threaded region (not shown but see bone anchor 202 of FIG. 2E) of the bone anchors 202a, 202b and 202c have been fully implanted in the vertebrae 182, 183 and sacrum 189. In preferred procedures, the bone anchor is directed so that it is implanted within an area of high bone density, e.g. the pedicles 186 of the vertebrae angled towards the vertebral body 187. As shown in FIG. 4G, the housing of each bone anchor remains partly or completely exposed above the surface of the vertebrae so that one or more of a connection system component and deflection system component could be secured to each bone anchor 202a, 202b and 202c.

Referring again to FIG. 4G, a coaxial head 160a is coaxially mounted in bone anchor 202a and another coaxial head 160b is coaxially mounted in bone anchor 202c. A side-swivel connector 400 is externally mounted to the housing of bone anchor 202b. A deflection rod 104 is coaxially mounted in the housing of bone anchor 202b A vertical rod 106 connects vertebrae 182 and 183. Vertical rod 106 is connected at one end to deflection rod 104 by ball joint 108. Vertical rod 106 is connected at the other end by coaxial head 160a to bone anchor 202a. A second vertical rod 486 connects bone anchors 202b and 202c. Vertical rod 486 is connected at one end to bone anchor 202b by side-swivel connector 400. Vertical rod 486 is connected at the other end by coaxial head 160a to bone anchor 202b.

The dynamic stabilization assembly 480 of FIG. 4G provides dynamic stabilization at the L4-L5 level and fixed stabilization at the L5-S1 level. Connector 400 and coaxial head 160a permit assembly of dynamic stabilization assembly 480 for a wide range of different patient anatomies and/or placement of bone anchors 202a, 202b and 202c. Side-swivel connector 400 is particularly useful where, as here, there is slight lateral displacement between the bone anchor positions on either side of a level.

Figure 5E:
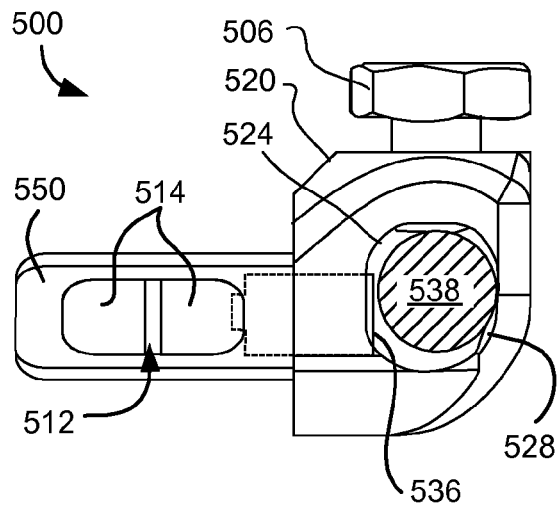
FIGS. 5E to 5F are views illustrating the clamping action of the polyaxial connector of FIGS. 5A to 5D.

FIGS. 5A-5G show an offset-swivel connector 500 for connecting a bone anchor to a vertical rod with more degrees of freedom than the connector of FIG. 1E. Offset-swivel connector 500 mounts externally of the housing of a bone anchor and is, thus, an example of an offset head/connector. Offset-swivel connector 500 comprises seven components and allows for two linear degrees of freedom and two angular degrees of freedom in connecting a vertical rod to a bone anchor. Offset-swivel 500 has similar functionality to side-swivel 400 but with the addition of a lateral offset from the bone anchor which may be useful in connecting bone anchors that are laterally offset from one another for example connecting a bone anchor on the sacrum to a bone anchor to a lumbar vertebra (S1 to L5). FIG. 5A shows an exploded view of the offset-swivel connector 500 revealing the components. The seven components of offset-swivel connector 500 are snap ring 502, pin 504, locking screw 506, clamp ring 510, swivel 520, plunger 530, and offset adapter 550. FIG. 5B shows an alternative size of an offset adapter component 550a. FIG. 5C is a view of the swivel component 520. FIG. 5D shows a perspective view of connector 500 after assembly of the seven components.

The clamp ring 510 comprises a ring with a gap 512. Clamp ring 510 is sized such that it can slide freely up and down the housing of a bone anchor and rotate around the housing when the ring is relaxed. However, when the gap 512 is forced closed, the clamp ring 510 grips the housing and prevents the clamp from moving in any direction. On each side of gap 512 is an ear 514. Each ear 514 has an aperture 516, 518. The ears 514 are designed to mate with a channel in the offset adapter 550.

Offset adapter 550 has a rectangular channel 551 designed to receive the ears 514 of clamp ring 510. Offset adapter has an aperture 555 at one end for receiving pin 504. When pin 504 is inserted through aperture 555 it engages the aperture 516 of clamp ring 510 thereby securing clamp ring 510 to offset adapter 550. On one side of offset adapter 550 is a cylindrical extension 554. A channel 552 passes through the middle of cylindrical extension 554. Cylindrical extension 554 has a groove 558 on its outer surface. The groove 558 is sized so that snap ring 502 fits entirely within the groove 558 when snap ring 502 is compressed. The first end 532 of plunger 530 is inserted into channel 552 of offset adapter 550. Plunger 530 has a protrusion 532 at one end that is designed to fit into aperture 518 of clamp ring 510 securing it into offset adapter 550. Plunger 530 has a lip 536 at the other end, so that it cannot fall entirely through channel 552. Snap ring 502 is expanded slightly and pushed over cylindrical extension 554 of clamp ring 510 until snap ring 502 snaps into groove 558 of cylindrical extension 554.

Note that if greater lateral displacement is required, all that is necessary is to increase the length of cylindrical extension 554. An alternative length of offset adapter 550a is shown in FIG. 5B which is the same in all respects as the offset adapter 550 of FIG. 5A except that cylindrical extension 554a is longer than cylindrical extension 554.

As shown in FIG. 5C, swivel 520 has an aperture 521 for receiving tubular extension 554 of offset adapter 550. Aperture 521 has a groove 522 sized to engage snap ring 502. Snap ring 502 is compressed as tubular extension 554 is inserted into aperture 521. However, when tubular extension 554 is inserted the correct distance into aperture 521, groove 558 becomes aligned with groove 522 and snap ring 502 can expand into groove 522. When snap ring 502 has expanded into groove 522 a portion of snap ring 502 remains within each of grooves 522 and 558. Offset adapter 550 is thus locked into aperture 521 of swivel 520. Cylindrical extension 554 can, however, rotate within aperture 521. Furthermore, plunger 530 may still slide somewhat in and out of channel 552 of offset adapter 550.

Referring again to FIG. 5A, swivel 520 has a channel 524 for receiving a vertical rod. The aperture 521 intersects channel 524. The lip 536 of plunger 530 protrudes slightly into the channel 524 when assembled. However, a lip 525 on channel 523 prevents plunger 530 from slipping too far into channel 524. Swivel 520 also has a threaded aperture 528 sized to fit locking screw 506.

Figure 5F:
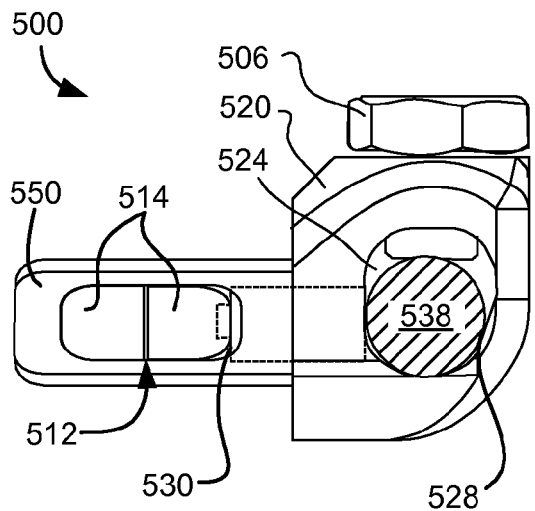

FIGS. 5E and 5F illustrate the clamping action of offset-swivel connector 500 to clamp a rod 538 to the housing of a bone anchor. As shown in FIG. 5E, connector 500 has a channel 524 for receiving a rod 538 (shown in section). As shown in FIG. 5D, locking screw 506 protrudes into one side of the channel 524 and lip 536 of plunger 530 protrudes into another portion of the channel 524. Clamp ring 510 receives the housing of a bone anchor and has enough room that clamp ring 510 (shown in FIG. 5G) may slide up and down on the housing and rotate around the housing.

As shown in FIG. 5F, when set screw 506 is tightened against a rod 538 within channel 524 of connector 500, the set screw pushes rod 538 against a ramp 528 at the opposite side of channel 524 from locking screw 506. Ramp 528 pushes rod 538 against lip 536 of plunger 530. Plunger 530 is then forced by rod 538 through channel 552 in offset adapter 550. The end plunger 530 bearing protrusion 532 is thereby forced against one ear 514 of clamp ring 510 closing gap 512 and preventing further movement of the clamp ring 510 relative to the housing. The force of plunger 530 against ears 514 also applies force between grooves 558 and 522 and locking ring 502 which serves to prevent further rotation of swivel 520 relative to offset adapter 550. In this way, operation of the single set screw 506 serves to lock the clamp ring 510 to the housing of the bone anchor and fix swivel 520 in a fixed position relative to offset adapter 550, and secure rod 538 within the channel 524 of connector 500.

Figure 5G:
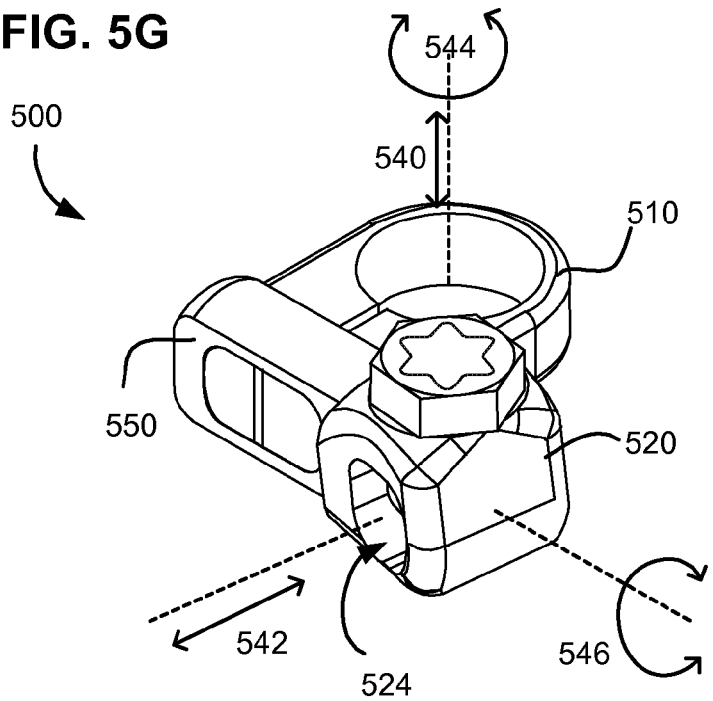
FIG. 5G is a perspective view illustrating the degrees of freedom of the polyaxial connector of FIGS. 5A to 5F.

As shown in FIG. 5G, offset-swivel connector 500 provides the same four degrees of freedom with respect to rod placement as the side-swivel connector 400. Connector 500 provides two linear degrees of freedom. First, clamp ring 510 can slide up and down the housing of the bone anchor within the range of travel provided by the housing surface as shown by arrow 540. Second, the rod can slide in and out of the channel 524 of connector 500 as shown by arrow 542. These linear degrees of freedom are not necessarily orthogonal because the angle between the channel 524 and the axis of the clamp ring 510 is variable. However, during typical operation the axis of channel 524 and the clamp ring will be approximately perpendicular and thus the degrees of freedom are relatively independent. Connector 500 also provides two angular degrees of freedom. First, clamp ring 510 can rotate around the axis of the housing of a bone anchor as shown by arrow 544. Second, the swivel 520 of connector 500 can pivot about the axis of the tubular extension 514 of the clamp ring 510. This axis is orthogonal to the axis of the bone anchor. The four degrees of freedom provide sufficient degrees of freedom to connect a vertical rod from one bone anchor to another bone anchor so long as the linear and angular displacement is within range.

Figure 5H:
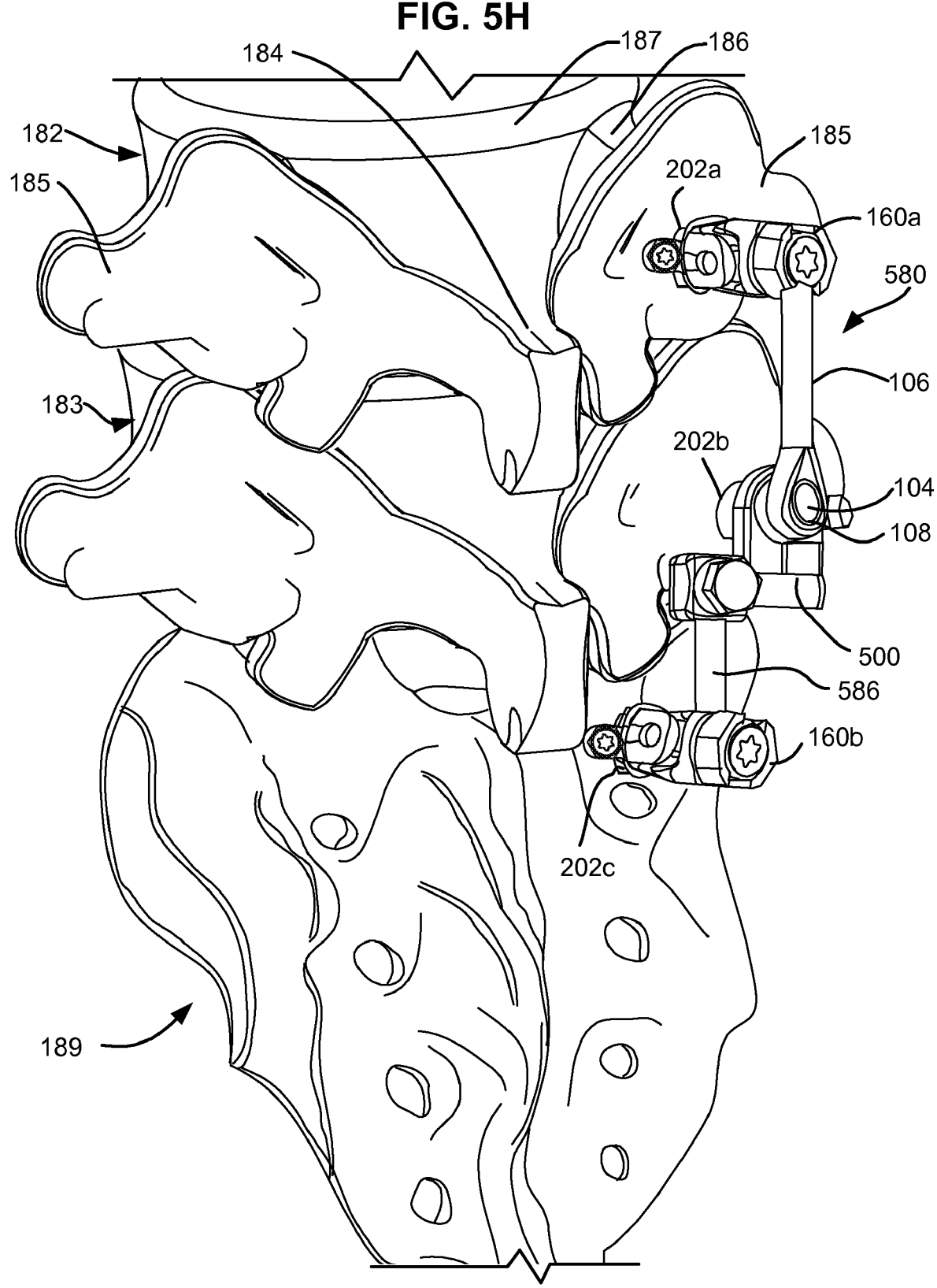
FIG. 5H is a posterior view of a multi-level dynamic stabilization assembly utilizing the polyaxial connector of FIGS. 5A to 5F in accordance with an embodiment of the present invention.

The offset-swivel connector of FIGS. 5A to 5G may be used to construct a dynamic stabilization assembly for one or more levels of the spine of a patient. FIG. 5H shows one example of a two-level dynamic stabilization assembly 580 utilizing the offset-swivel connector 500 of FIGS. 5A to 5G. FIG. 5H shows how the components may be assembled and implanted in the spine of a patient to provide a multilevel dynamic stabilization assembly which provides dynamic stabilization of the spine and load sharing. Note that an identical or similar construct would preferably be implanted on the left side of the spine.

As shown in FIG. 5H, dynamic stabilization assembly 580 spans two vertebrae 182 (L4) and 183 (L5) and the sacrum 189 (S1) thus two levels of the spine (L4-L5 and L5-S1). A vertical rod 106 is connected across the L4-L5 levels. Vertical rod 106 is secured at one end to a deflection rod 104 by a ball joint 108 and at the other end to a bone anchor 202a through a coaxial head 160a. The deflection rod 104 provides controllable flexibility and load sharing at the L4-L5 level of the spine. Vertical rod 586 connects the L5-S1 level. Vertical rod 586 is secured at one end to bone anchor 202b by an offset-swivel connector 500. Vertical rod 586 is secured at the other end to bone anchor 202c by a coaxial head 160b. There is no deflection rod at this level—this system is designed to hold the sacrum and L5 vertebra in fixed relationship to each other—possibly in conjunction with a fusion of the vertebra and sacrum.

As shown in FIG. 5H, bone anchors 202a, 202b are implanted in vertebrae 182 and 183 on the right side of the spinous process 184 between the spinous process 184 and the transverse process 185. Bone anchor 202c is implanted in the sacrum transverse (on the right side) of the sacral crest and superior of the first sacral foramina. The threaded region (not shown but see bone anchor 202 of FIG. 2E) of the bone anchors 202a, 202b and 202c have been fully implanted in the bone of vertebrae 182, 183 and sacrum 189. In preferred procedures, the bone anchors are directed so that they are implanted within an area of high bone density, e.g. the pedicles 186 of the vertebrae angled towards the vertebral body 187. As shown in FIG. 5H, the housing of each bone anchor remains partly or completely exposed above the surface of the vertebrae so that one or more of a connection system component and deflection system component could be secured to each bone anchor 202a, 202b and 202c.

The dynamic stabilization assembly 580 of FIG. 5H provides dynamic stabilization at the L4-L5 level and fixed stabilization at the L5-S1 level. Connector 500 and coaxial heads 160a and 160b permit assembly of dynamic stabilization assembly 580 for a wide range of different patient anatomies and/or placement of bone anchors 202a, 202b and 202c. Offset-swivel connector 500 is particularly useful where, as here, there is lateral displacement in bone anchor position on either side of a level. It is a relatively simple matter to manufacture a range of offset-swivels having different amounts of lateral displacement. Only the length of offset adapter 550 and plunger 530 needs to be changed—all the other parts may be kept the same. FIG. 5B shows an offset adapter 550*a* having a larger lateral displacement than offset adapter 550 of FIG. 5A. Thus, offset-swivel adapter may be supplied to the surgeon in different sizes with the surgeon choosing the connector most suitable for the particular anatomy of the patient.

Figure 6A:
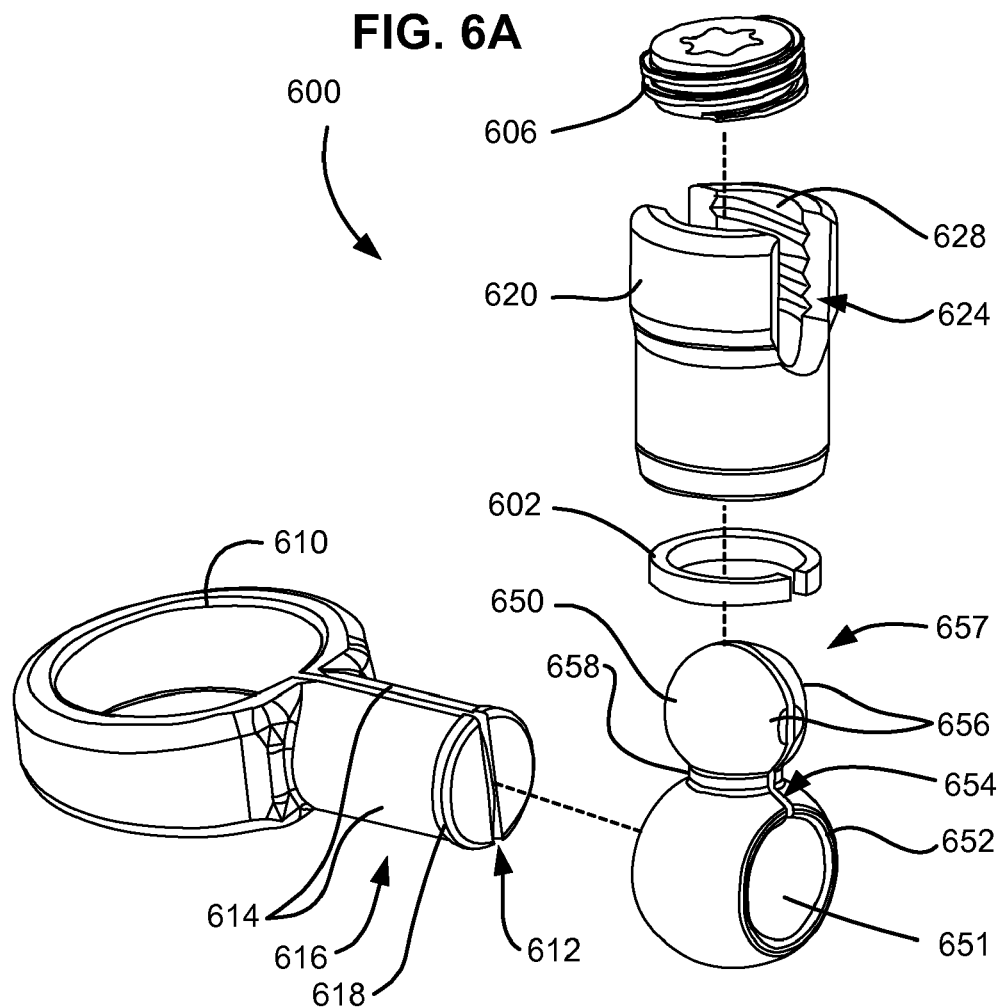
FIGS. 6A to 6C are perspective and exploded views of a polyaxial connector and its components in accordance with an embodiment of the present invention.
Figure 6B:
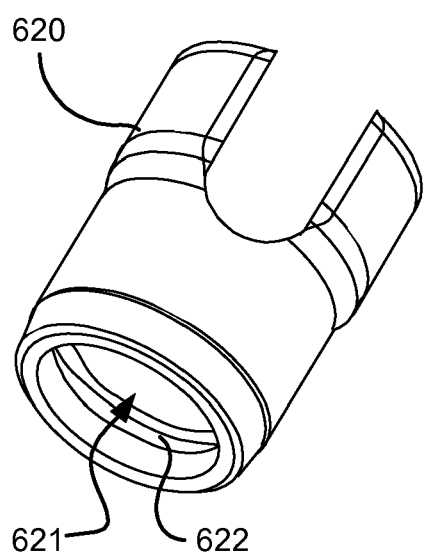
Figure 6C:
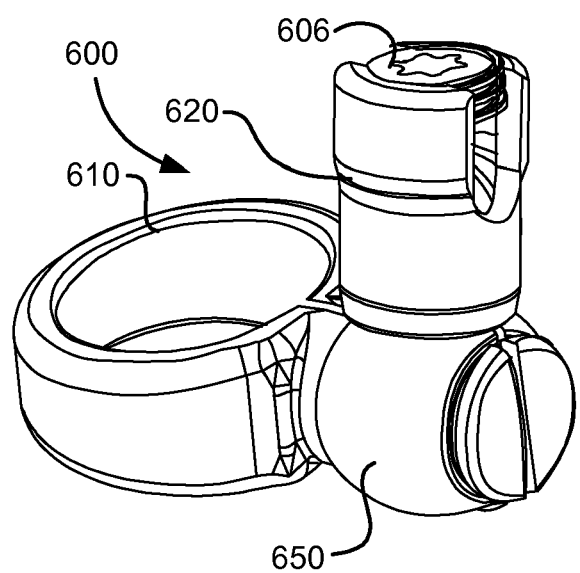

FIGS. 6A-6H show a polyaxial-swivel connector 600 for connecting a bone anchor to a vertical rod with more degrees of freedom than the connector of FIG. 1E. Polyaxial-swivel connector 600 mounts externally of the housing of a bone anchor and is thus an example of an offset head/connector. Polyaxial-swivel connector 600 comprises five components and allows for two linear degrees of freedom and three angular degrees of freedom in connecting a vertical rod to a bone anchor. Polyaxial-swivel 600 has similar functionality to side-swivel 400 but with the addition of a second axis of rotation. FIG. 6A shows an exploded view of the polyaxial-swivel connector 600 revealing the components. The five components of polyaxial-swivel connector are snap ring 602, locking screw 606, clamp ring 610, swivel 620, and swivel adapter 650. FIG. 6B shows an alternative view of swivel 620. FIG. 6C shows a perspective view of connector 600 after assembly of the five components.

The clamp ring 610 comprises a ring with a gap 612. Clamp ring 610 is sized such that it can slide freely up and down the housing of a bone anchor and rotate around the housing when the ring is relaxed. However, when gap 612 is forced closed, the clamp ring 610 grips the housing and prevents the clamp from moving in any direction. On each side of gap 612 is an ear 614. The ears 614 together form a cylindrical extension 616. The cylindrical extension 616 is designed to mate with a channel in the swivel adapter 650. The cylindrical extension 616 has a lip 618 to retain the cylindrical extension 616 within the channel of the swivel adapter 650 after assembly.

Swivel adapter 650 has a cylindrical channel 651 designed to receive the ears 614 of clamp ring 610. When cylindrical extension 616 is inserted fully through cylindrical channel 651, lip 618 engages swivel adapter 650 to retain ears 614 within swivel adapter 650. Swivel adapter may, however, rotate around the axis of cylindrical extension 616 of clamp ring 610.

Cylindrical channel 651 of swivel adapter 650 is surrounded by a ring 652 having a gap 654. On either side of gap 654 is an ear 656 extending from ring 652. Together, the ears 656 form a spherical extension 657 of ring 652 through which gap 654 is continued. Swivel adapter 650 may rotate around cylindrical extension 616 while gap 654 is open. However, when gap 654 is closed, swivel adapter 650 is clamped to cylindrical extension 616 and may not move. Between ring 652 and spherical extension 657 is a valley 658. Valley 658 is sized to receive snap ring 602. Snap ring 602 may be slipped over spherical extension 657 into valley 658.

As shown in FIG. 6B, swivel 620 has an aperture 621 for receiving spherical extension 657 of swivel adapter 650. Aperture 621 has a groove 622 sized to engage snap ring 602. Snap ring 602 is compressed as spherical extension 657 is inserted into aperture 621. However, when spherical extension 657 is inserted the correct distance into aperture 621, valley 658 becomes aligned with groove 622 and snap ring 602 can expand into groove 622. When snap ring 602 has expanded into groove 622 a portion of snap ring 602 remains within each of valley 658 and groove 622. Swivel adapter 650 is thus locked into aperture 621 of swivel 620. Spherical extension 657 can still rotate within aperture 621. Referring again to FIG. 6A, swivel 620 has a slot 624 for receiving a vertical rod. The aperture 621 intersects slot 624. Slot 624 has a threaded opening 628 sized to fit locking screw 606.

Figure 6D:
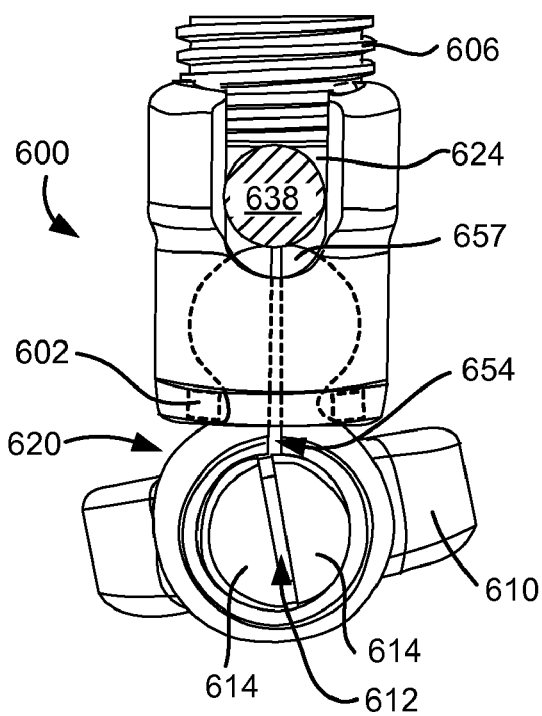
FIGS. 6D to 6E are views illustrating the clamping action of the polyaxial connector of FIGS. 6A to 6C.
Figure 6E:
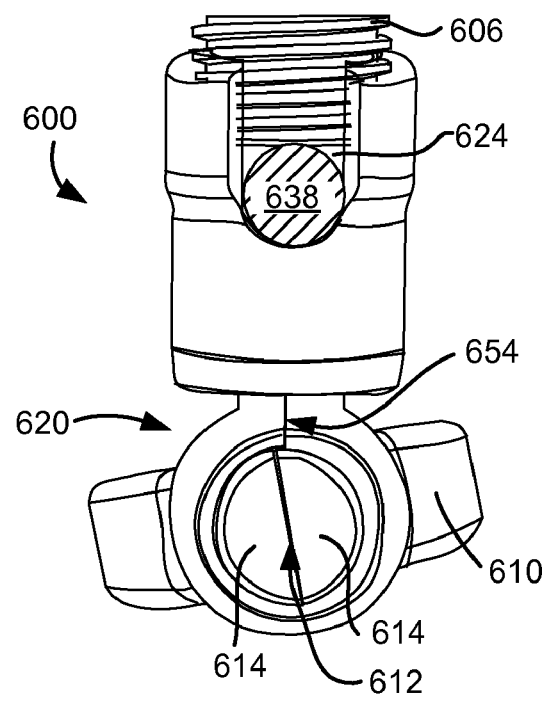

FIGS. 6D and 6E illustrate the clamping action of polyaxial-swivel connector 600 to clamp a rod 638 to the housing of a bone anchor. As shown in FIG. 6E, connector 600 has a slot 624 for receiving a rod 638 (shown in section). As shown in FIG. 6D, locking screw 606 protrudes into one side of the slot 624 and the spherical extension 657 of swivel adapter 650 protrudes into the other end of slot 624. As shown in FIG. 6D, when set screw 606 is tightened against a rod 638 within slot 624 of connector 600, the set screw 606 pushes rod 638 against a spherical extension 657 of swivel connector 650. As spherical extension 657 is pushed downward, it is squeezed by snap ring 602 forcing closed gap 654. The closing of gap 654 likewise forces closed gap 612 between the ears 614 of clamp ring 610. The pressure of the spherical extension 657 against snap ring 602 locks swivel adapter 650 to swivel 620. The closing of gap 654 locks swivel adapter 650 to cylindrical extension 616. The closing of gap 612 locks clamp ring 610 to the housing of the bone anchor. In this way, operation of the single set screw 606 serves to lock the clamp ring 610 to the housing of the bone anchor, and fix swivel 620 in a fixed position relative to swivel adapter 650, and secure rod 638 within the slot 624 of connector 600.

Figure 6F:
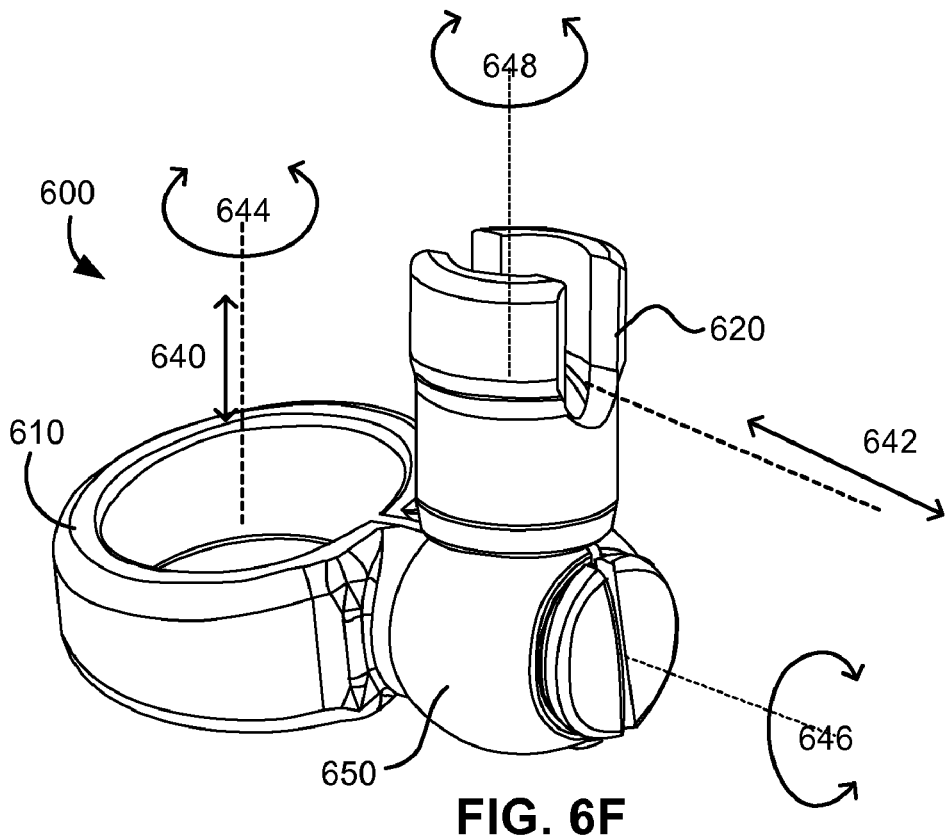
FIGS. 6F and 6G are perspective views illustrating the degrees of freedom of the polyaxial connector of FIGS. 6A to 6E.
Figure 6G:
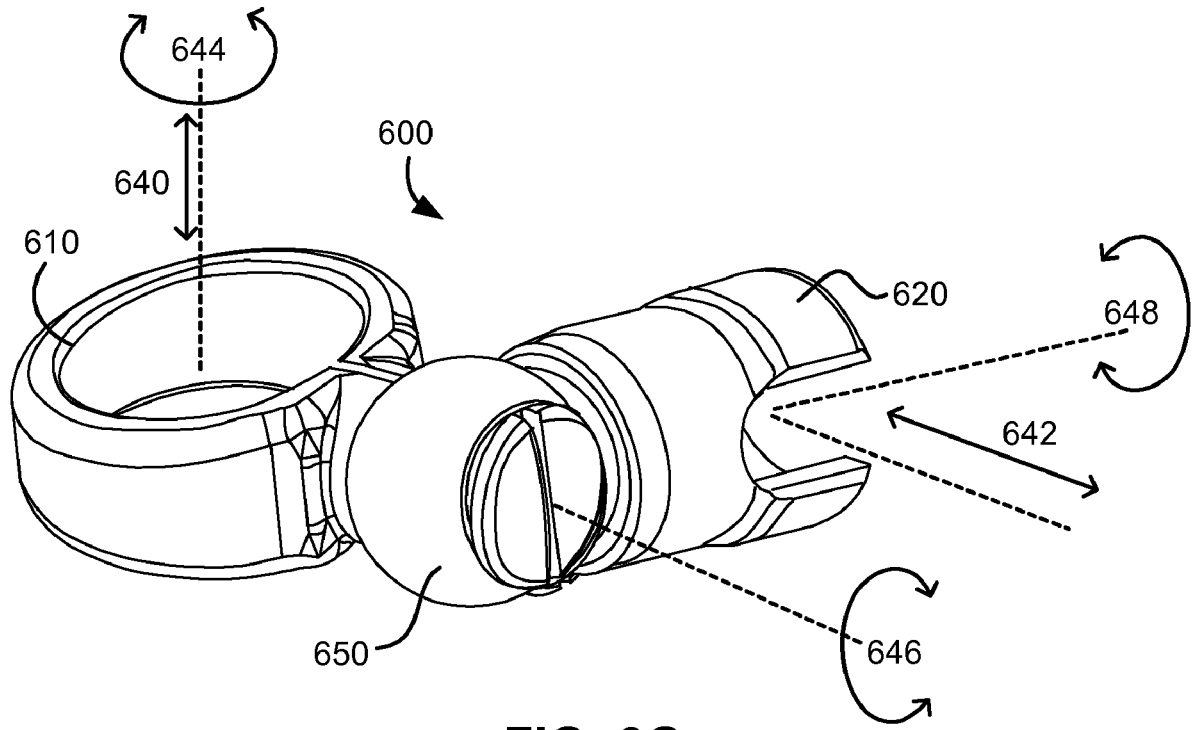

As shown in FIGS. 6F and 6G, polyaxial-swivel connector 600 provides five degrees of freedom with respect to rod placement. Connector 600 provides two linear degrees of freedom. First, clamp ring 610 can slide up and down the housing of the bone anchor within the range of travel provided by the housing surface as shown by arrow 640. Second, the rod can slide in and out of slot 624 of connector 600 as shown by arrow 642. These linear degrees of freedom are not necessarily orthogonal because the angle between slot 624 and the axis of the clamp ring 610 is variable. However, during typical operation the axis of slot 624 and the clamp ring will be approximately perpendicular and thus the degrees of freedom are relatively independent. Connector 600 also provides three angular degrees of freedom. First, clamp ring 610 can rotate around the axis of the housing of a bone anchor as shown by arrow 644. Second, swivel 620 of polyaxial-swivel connector 600 can pivot about the axis of the cylindrical extension 616 of the clamp ring 610 as shown by arrow 646. This axis is orthogonal to the axis of the bone anchor. Third, the swivel 620 can rotate around the spherical extension 657 of the swivel adapter 650 as shown by arrow 648. This axis is parallel to the axis 644 as shown in FIG. 6F and does not provide a truly independent degree of freedom. Note, however, that if the swivel adapter 650 is rotated 90 degrees around the cylindrical extension 616 the axis becomes perpendicular to the other two axes of rotation as shown in FIG. 6G. With the swivel adapter positioned as in FIG. 6G, the axes of angular rotation of polyaxial swivel connector 600 are all perpendicular. The four/five degrees of freedom provide sufficient degrees of freedom to connect a vertical rod from one bone anchor to another bone anchor (so long as the linear and angular displacement is within range).

The polyaxial-swivel connector of FIGS. 6A to 6G may be used to construct a dynamic stabilization assembly for one or more levels of the spine of a patient. FIG. 6H shows one example of a two-level dynamic stabilization assembly 680 utilizing the polyaxial-swivel connector 600 introduced in FIGS. 6A-3F. FIG. 6H shows how the components may be assembled and implanted in the spine of a patient to provide a multilevel dynamic stabilization assembly which provides dynamic stabilization of the spine and load sharing. Note that an identical or similar construct would preferably be implanted on the left side of the spine. Dynamic stabilization assembly 680 spans three vertebrae 181, 182 and 183 and thus two levels of the spine 181-182 and 182-183. A vertical rod 106a or 106b is connected across each of the levels. Each vertical rod is secured at one end to a deflection rod 104a by a ball joint 108a, 108b and at the other end to a bone anchor 202 through a connector. The deflection system provides controllable flexibility and load sharing at each level of the spine.

FIG. 6H shows three adjacent vertebrae 181, 182 and 183. Bone anchors 202a, 202b and 202c have been implanted in each of the vertebrae 181, 182 and 183 on the right side of the spinous process 184 between the spinous process 184 and the transverse process. The threaded region (not shown but see bone anchor 202 of FIG. 2E) of the bone anchors 202a, 202b and 202c have been fully implanted in the vertebrae 181, 182 and 183. In preferred procedures, the bone anchor is implanted so that it is implanted within one of the pedicles 186 angled towards the vertebral body 187. As shown in FIG. 6H, the housing of each bone anchor remains partly or completely exposed above the surface of the vertebrae so that one or more of a connection system component and deflection system component could be secured to each of bone anchors 202a, 202b and 202c.

Referring again to FIG. 6H, a coaxial head 160 is installed in bone anchor 202c. A polyaxial-swivel connector 600 is externally mounted to the housing of bone anchor 202b. A deflection rod 104a is coaxially mounted in the housing of bone anchor 202a. A deflection rod 104b is coaxially mounted in the housing of bone anchor 202b. A vertical rod 106a connects vertebra 202a and vertebra 202b. Vertical rod 106a is connected at one end to deflection rod 104a by ball joint 108a. Vertical rod 106a is connected at the other end by polyaxial-swivel connector 600 to bone anchor 202b. A second vertical rod 106b connects vertebra 202b and vertebra 202c. Vertical rod 106b is connected at one end to deflection rod 104b by ball joint 108b. Vertical rod 106b is connected at the other end by coaxial head 160 to bone anchor 202C.

The dynamic stabilization assembly 680 of FIG. 6H thus has a vertical rod 106a, 106b stabilizing each spinal level (202a-202b and 202b-202c). Each of the vertical rods 106a, 106b is secured rigidly to a bone anchor (202b, 202c). Each of the vertical rods 106a, 106b is secured at the other end by a ball joint to a deflection rod thereby allowing for some movement and load sharing by the dynamic stabilization assembly. Connector 600 and coaxial head 160 permit assembly of dynamic stabilization assembly 680 for a wide range of different patient anatomies and/or placement of bone anchors 202a, 202b and 202c.

Figure 7C:
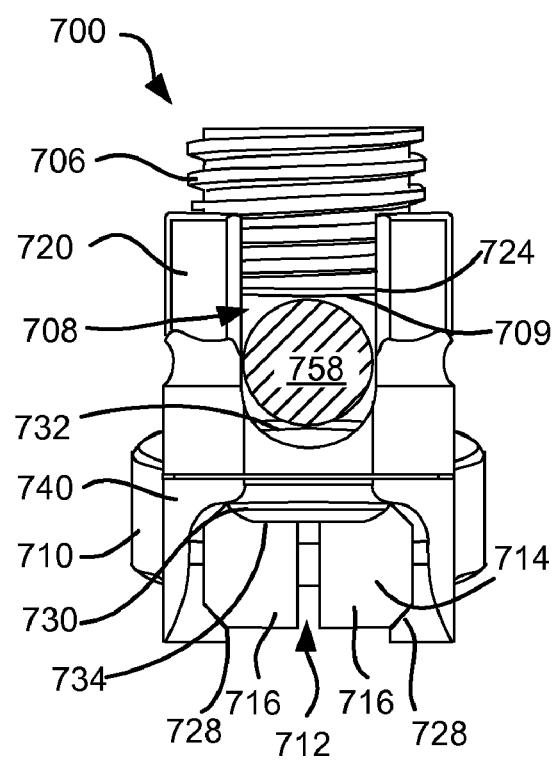
FIGS. 7C to 7D are views illustrating the clamping action of the polyaxial connector of FIGS. 7A and 7B.

FIGS. 7A-7F show an alternative polyaxial connector 700 for connecting a bone anchor to a vertical rod with more degrees of freedom than the connector of FIG. 1E. Polyaxial connector 700 mounts externally of the housing of a bone anchor and is thus an example of an offset head/connector. Polyaxial connector 700 comprises seven components and allows for three degrees of freedom of orientation and two degrees of freedom of position in connecting a vertical rod to a bone anchor. FIG. 7A shows an exploded view of the in-line connector 700 revealing the components. The seven components of in-line connector are pivot pin 704, locking set screw 706, snap ring 702, clamp ring 710, saddle 720, plunger 730 and adapter 740.

Clamp ring 710 comprises a ring 711 with a gap 712. Clamp ring 710 is sized such that it can slide freely up and down the housing of a bone anchor and rotate around the housing when the ring 711 is relaxed. However when the gap 712 is forced closed, the clamp ring 710 grips the housing and prevents the clamp from moving in any direction. On each side of gap 712 is an ear 714. Each ear 714 terminates in a cylindrical surface 716 having an aperture 718. The ears 714 are inserted into a clevis 741 of adapter 740.

Adapter 740 is generally cylindrical with a bore 746 along the longitudinal axis. Adapter 740 includes a clevis 741. Bore 746 intersects clevis 741. The clevis 741 is sized to receive ears 714 of clamp ring 710 through the side of clevis 741. Clevis 741 also has a pair of apertures 742 for receiving pivot pin 704. Pivot pin 704 passes through apertures 742 and also through apertures 718 of clamp ring 710 thereby securing clamp ring 710 into clevis 741. Note that the apertures 718 of clamp ring 710 are slightly larger than the diameter of pivot pin 704 so that ears 714 have a small range of travel about pivot pin 704 in addition to being able to rotate around pivot pin 704 over a range of about 180 degrees. Thus, even with pivot pin 704 in position, ears 714 have some vertical range of travel within the clevis 741 of adapter 740. Close to the opposite end of adapter 740 bore 746 has a groove 744 sized and configured to receive snap ring 702.

Plunger 730 is received into a bore 746 in adapter 740. The lower end of plunger 730 is the same diameter as the bore 746 of adapter 740. Plunger 730 has a step 736 where the plunger diameter is reduced in size to the interior diameter of the bore 726 of saddle 720. Referring again to FIG. 7A, the lower surface 732 of plunger 730 is concave with the same curvature as the cylindrical surface 716 of ears 714 of clamp ring 710. When installed through the bore 726 in saddle 720, the lower surface 732 of plunger 730 rests on the cylindrical surface 716 of ears 714. The upper surface 734 of plunger 730 protrudes out of the bore 746 into the bore 726 of saddle 720. Step 736 prevents plunger 730 from travelling entirely into bore 726. Thus, when saddle 720 is connected to adapter 740, plunger 730 is trapped between ears 714 and saddle 720 while still having a range of motion within bore 746. Plunger 730 is thereby captured within bore 746 of adapter 740 but has a range of travel up and down bore 746.

Saddle 720 is generally cylindrical with bore 726 along the longitudinal axis. Saddle 720 has clevis 723. Bore 726 communicates between the clevis 723 and lower end 721 of saddle 720. The lower end 721 is sized to fit within bore 746 of adapter 740. The lower end 721 has a groove 725 sized and configured to receive snap ring 702. Snap ring 702 can be inserted into groove 725 and compressed so that lower end 721 of saddle 720 may be inserted into bore 746 with upper end 732 of plunger 730 received into bore 726 of adapter 720. When groove 725 of saddle 720 is aligned with groove 744 of adapter 740 snap ring expands into groove 744. The expansion of snap ring 702 locks adapter 740 to saddle 720 while permitting saddle 720 to rotate relative to adapter 740.

Clevis 723 of saddle 720 includes slot 724 is sized to receive a rod which may be a vertical rod, e.g. vertical rod 106 of FIG. 1A. Bore 726 is threaded adjacent the open end of slot 724 and configured to engage set screw 706. When assembled, upper surface 732 of plunger 730 protrudes pass the base of slot 724. FIG. 7B shows a perspective view of connector 700 after assembly of the six components.

Figure 7D:
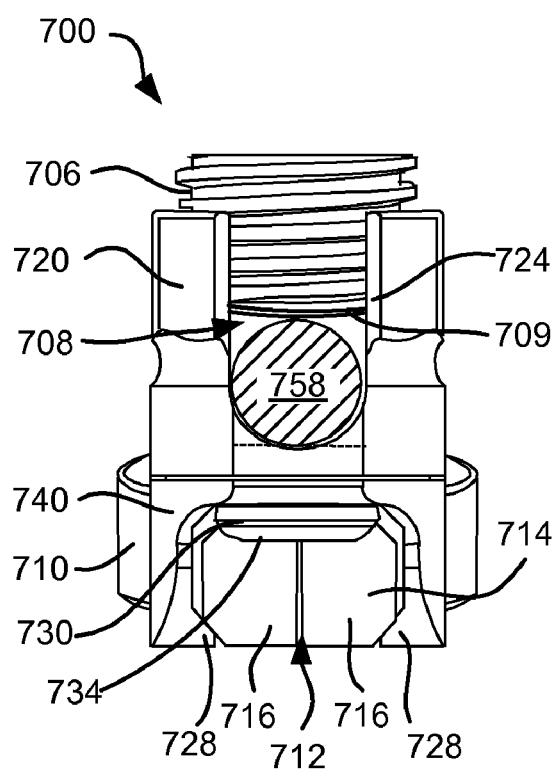

FIGS. 7C and 7D illustrate the clamping action of connector 700. As shown in FIG. 7C, when assembled, with set screw 706, connector 700 defines an aperture 708 for receiving a rod 758 (shown in section). Aperture 708 is bordered on the upper side by the lower surface 709 of set screw 706, on the lower side by the upper surface 734 of plunger 730; and on each side by the sides of slot 724. As shown in FIG. 7E, when set screw 706 is tightened against a rod 758 within aperture 708 of connector 700, the rod 758 pushes down on the upper surface 734 of plunger 730. Plunger 730 slides within bore 726 of saddle 720 and bore 746 of adapter 740. The lower surface 732 of plunger 730 pushes down upon the cylindrical surface 716 of ears 714 of clamp ring 710. The ears 714 of clamp ring 710 are in turn forced against a pair of ramps 728 at the end of lower clevis 721 of saddle 720. Ramps 728 force ears 714 together closing gap 712 and securing clamp ring 710 to the housing of a bone anchor. In this way, operation of the single set screw 706 serves to lock the clamp ring 710 to the housing of the bone anchor, fix saddle 720 in a fixed position relative to adapter 740, fix adapter 740 relative to clamp ring 710 and secure a rod 738 within the aperture 708 of connector 700. Configured as shown in FIG. 7E, connector 700 can be used in similar fashion to the in-line connector 300 shown in FIGS. 3A-3G and be used to assemble a multilevel dynamic stabilization assembly similar to that shown in FIG. 3G.

As shown in FIG. 7F, connector 700 provides five degrees of freedom with respect to rod placement. Connector 700 provides two degrees of freedom of position. First, clamp ring 710 can slide up and down the housing of the bone anchor within the range of travel provided by the housing surface as shown by arrow 740. Second, the rod can slide in and out of the aperture 708 of connector 700 as shown by arrow 742. Connector 700 also provides three degrees of freedom with respect to orientation. First, clamp ring 710 can rotate around the axis of the housing of a bone anchor as shown by arrow 744. Second, the adapter 740 of connector 700 can pivot about the axis of pin 704 as shown by arrow 746. This axis is orthogonal to the axis of the bone anchor. Third, the saddle 720 can pivot about the axis of bores 726, 746 as shown by arrow 748. This last degree of freedom is redundant of the rotation around the housing with the connector in the position shown. However, as shown in FIG. 7F, as the angle of adapter 740 to clamp ring 710 is varied, the axis of rotation of saddle 720 ceases to be parallel to axis of rotation of the clamp ring 710 around the housing. However, the four plus degrees of freedom provide sufficient degrees of freedom to connect a vertical rod from one bone anchor to another bone anchor (so long as the linear and angular displacement is within range. Configured as shown in FIG. 7F, connector 700 can be used in similar fashion to the swivel connector 400 shown in FIGS. 4A-4G and be used to assemble a multilevel dynamic stabilization assembly similar to that shown in FIG. 4G.

Versatile Coaxial Heads

As described above with respect to FIGS. 1C and 1D, in some embodiments of the present invention, a connection system component e.g. a coaxial head/connector may be mounted in the cavity of a bone anchor to secure the bone anchor to a vertical rod. One advantage of this approach is that a range of sizes of bone anchors may be designed to fit the coaxial head thus allowing the bone anchor most appropriate for the implant location to be selected. Another advantage is that the coaxial head can be selected and attached to the bone anchor after the bone anchor is implanted in the bone which simplifies implantation of the bone anchor. FIGS. 8A-8D illustrate alternative designs for coaxial heads which may be used with the coaxial bone anchor 202 of FIG. 2E.

FIGS. 8A and 8B show views of one preferred embodiment of a coaxial head 800 for use with coaxial bone anchor 202 of FIG. 2E. FIG. 8A shows an exploded view illustrating the internal components and assembly of the coaxial head 800. The components of coaxial head 800 include dowel pin 802, pin 804, locking set screw 806, locking screw 808, yoke 810, saddle 830, plunger 850 and compression ball 860. FIG. 8B shows the coaxial head 800 assembled and prepared for installation in a bone anchor 202.

Referring to FIG. 8A, this coaxial head 800 includes a yoke 810 including rod 820 connected to a U-shaped head 812 with arms 814, 816. Rod 820 is connected to the U-shaped head 812 of yoke 810. The rod 820 is sized to be received in the cavity 235 of the housing 230 of a bone anchor 202. Rod 820 is sufficiently long to ensure a secure mating between coaxial head 800 and a bone anchor but need not entirely fill cavity 235 of the bone anchor. A low profile threaded screw housing 822 is connected to the rod adjacent to head 812. Screw housing 822 holds screw 808 in position to engage groove 232 at the proximal end of housing 230 of bone anchor 202.

Each of the arms 814, 816 of yoke 810 includes an aperture 815, 817 through which pin 804 can be placed. The pin 804 can be laser welded or force fit or glued into the yoke 810, as desired. The pin 804 can be smooth or roughened as discussed below. Further, the pin 804 can be cylindrical or be comprised of multiple sides as shown in FIG. 8A. In FIG. 8A, pin 804 has six sides and one or more of the accommodating apertures 815, 817 can also include mating sides in order to fix the position of the pin 804 in the yoke 810.

A compression sphere 860 is placed over the pin 804. The compression sphere 860 can have a roughened surface if desired to assist in locking the sphere in place as described below. The compression sphere 860 can include one or more slits 862 to assist in compressing the sphere 860 about the pin 804. The compression sphere 860 has an inner bore 864 that is cylindrical or with multiple sides in order to conform and be received over the pin 804. One or more spacer rings can be used to space the compression ring from the yoke 810 in order to assist in providing the range of motion and degrees of freedom that are advantageous to the embodiments of the invention.

Mounted about the compression sphere 860 is the saddle 830. Saddle 830, includes a cylindrical body 832 with a lower end having an aperture 834 that can receive the compression sphere 860. The aperture 834 can have a concave surface as depicted in FIG. 8A. Accordingly, the compression sphere 860 fits inside of the concave surface of aperture 834 and is free to move therein until restrained as described below. As is evident from the figures, the lower end of the cylindrical body 832 about the aperture 834 has some of the material removed in order to accommodate relative motion of the yoke 810. Essentially, the portion of the cylindrical body 832 adjacent to the arms 814, 816 of the yoke 810 is removed to accommodate the yoke 810 and the range of motion of the yoke.

The saddle 830 of the coaxial head 800 includes an internal cylindrical bore 840 which is preferably substantially parallel to a longitudinal axis of the saddle 830. This bore 840 is open to the aperture 834 and is open and preferably substantially perpendicular to the upper end 831 of the saddle 830. At the upper end 831 of the saddle 830, the bore 840 is threaded and can accept the locking set screw 806. Along the sides, beginning at the upper end 831 are defined aligned U-shaped slots 842, 844 that extend through the saddle 830 from the outer surface to the bore 840. These U-shaped slots are open to the upper end 831 of saddle 830 in order to have the locking set screw 806 accepted by the threads of bore 840. Plunger 850 is positioned in the bore 840 between the set screw 806 and the compression sphere 860. The plunger 850 can slide somewhat in the bore 840, but the plunger 850 is restrained by a dowel pin 802 received through aperture 836 in saddle 830 and into aperture 852 in plunger 850. Thus, the plunger 850, until locked into position, can move somewhat in bore 840.

The plunger 850 has a generally cylindrical body so that the plunger 850 can fit into bore 840. The plunger 850 has a concave upper surface 854. This surface 854 is shaped to fit a rod, for example a vertical rod e.g. vertical rod 106 of FIG. 1A. The plunger 850 includes a concave lower surface 856 which can accommodate the compression sphere 860. Adjacent to the lower concave surface 856 there is an additional concavity 858 on either side of plunger 850 which is used to accommodate the relative motion of arms 814, 816 of yoke 810. The concave surfaces 854 and 856 can be roughened, if desired, to assist in locking the saddle 830 relative to the yoke 810.

When coaxial head 800 is assembled as shown in FIG. 8B, rod 820 may be inserted into the cavity 235 of the housing 230 of bone anchor 202. Yoke 810 can then be rotated to the desired orientation. Locking screw 808 can then be tightened to lock coaxial head 800 to bone anchor 202. A rod may be inserted into slots 842, 844 before or after locking coaxial head 800 to bone anchor 202. With a rod received in the U-shaped slots 842, 844, the locking set screw 806, when tightened, presses against the rod. The rod consequently can press against upper surface 854 of the plunger 850. Plunger 850 consequently slides through bore 840 until lower surface 856 contacts and presses upon compression sphere 860. Consequently, compression sphere 860 is compressed against pin 804. Thus the rod is locked relative to the saddle 830 and the saddle 830 is locked relative to the yoke 810. The design is advantageous in that tightening the locking set screw 806 urges the elements together and causes the resultant locking both of the coaxial head 800 and the rod.

FIGS. 8C and 8D show views of a second preferred embodiment of a coaxial head 870 for use with coaxial bone anchor 202 of FIG. 2E. FIG. 8C shows an exploded view illustrating the internal components and assembly of the coaxial head 870. The components of coaxial head 870 include dowel pin 802, pin 804, locking set screw 806, locking screw 808, yoke 810, saddle 880, plunger 850, upper plunger 872 and compression ball 860. Thus, in this embodiment, saddle 880 and upper plunger 872 are the only differences between coaxial head 870 and coaxial head 800 of FIGS. 8A-8B. FIG. 8D shows the coaxial head 870 assembled and prepared for installation in a bone anchor 202.

Referring to FIG. 8C, coaxial head 870 includes dowel pin 802, pin 804, locking set screw 806, locking screw 808, yoke 810, plunger 850 and compression ball 860 as previously described. Mounted about the compression sphere 860 is saddle 880. Saddle 880, includes a cylindrical body 882 with a lower aperture 884 that can receive the compression sphere 860. The aperture 884 can have a concave surface as depicted in FIG. 8C. Accordingly, the compression sphere 860 fits inside of the concave surface of aperture 884 and is free to move therein until restrained as described below. As is evident from the figures, the lower end of the cylindrical body 882 about the aperture 884 has some of the material removed in order to accommodate relative motion of the yoke 810. Essentially, the portion of the cylindrical body 882 adjacent to yoke 810 is removed to accommodate the yoke 810 and the relative motion of the yoke.

The saddle 880 of coaxial head 870 includes an internal cylindrical bore 890 which is preferably substantially parallel to a longitudinal axis of the saddle 880. This bore 890 is open to the aperture 884 and is open and preferably substantially perpendicular to the upper end 881 of the saddle 880. At the upper end 881 of the saddle 880, the bore 890 is threaded and can accept the locking set screw 806. A slot 894 passes through one side of cylindrical body 882 of saddle 880 from the outer surface to the bore 890.

Plunger 850 is positioned in the bore 890 between the slot 894 and the compression sphere 860. The plunger 850 can slide somewhat in the bore 890, but the plunger 850 is restrained by dowel pin 802 received through aperture 886 in the saddle 880 and into aperture 852 in the plunger 850. Thus, the plunger 850, until locked into position, can move somewhat in the bore 890. Upper saddle 872 is positioned between the locking set screw 806 and the slot 894. Upper saddle 872 has a peg 874 which is received in a cavity in the lower surface of locking set screw 806. Peg 874 couples upper plunger 872 to locking set screw 806 while still permitting locking set screw 806 to rotate relative to upper plunger 872. Upper plunger 872 has a concave lower surface 876 which is shaped to fit a rod, for example, vertical rod 106 of FIG. 1A. The concave surface 876 can be roughened, if desired, to assist in locking the rod to the saddle 880.

When coaxial head 870 is assembled as shown in FIG. 8D rod 820 may be inserted into the cavity 235 of the housing 230 of bone anchor 202. Yoke 810 can then be rotated to the desired orientation. Locking screw 806 can then be tightened to lock coaxial head 870 to bone anchor 202. A rod may be inserted into slots 892, 894 before or after locking coaxial head 870 to bone anchor 202. The rod may be inserted through the side of saddle 880 into slot 894 the side access to the slot facilitates insertion of the rod into the coaxial head 870 in some situations. The locking set screw 806, when tightened, presses against the upper plunger 872. The lower surface 876 of the upper plunger 872 pushed on the rod. The concavity of the lower surface helps to trap the rod within slot 894 and prevent the rod from slipping sideways out of slot 894 during tightening of locking set screw 806. The rod consequently presses against upper surface 854 of the plunger 850. Plunger 850 consequently slides through bore 890 until lower surface 856 contacts and presses upon compression sphere 860. Consequently, compression sphere 860 is compressed against pin 804. Thus, the rod is locked relative to the saddle 880 and the saddle 880 is locked relative to the yoke 810. The design is also advantageous in that tightening the locking set screw 806 urges the elements together and causes the resultant locking both of the coaxial head 870 and the rod. The design has the additional advantage of allowing side entry of the rod into the coaxial head 870.

As shown in FIG. 8E, coaxial head 800 provides three degrees of freedom of orientation with respect to rod placement. First, prior to the tightening of set screw 808, coaxial head 800 can rotate within housing 230 of bone anchor 202. Thus, coaxial head 800 can rotate around the long axis of bone anchor 202 as shown by arrow 844. Second, saddle 830 can rotate relative to yoke 810 around the axis of pin 804 as shown by arrow 846. This axis is orthogonal to the axis of the bone anchor. Third, saddle 830 can rotate about ball 860 around an axis perpendicular to the axis of pin 804 as shown by arrow 848. This third axis is perpendicular to the long axis of the bone anchor when coaxial head 800 is as shown in FIG. 8E. However, if saddle 830 pivots 90 degrees around pin 804, this third axis becomes parallel and thus redundant of the rotation around the axis of the bone anchor. Coaxial head 800 however provides sufficient degrees of freedom to connect a vertical rod from one bone anchor to another bone anchor (so long angular displacement is within range. Coaxial head 870 of FIGS. 8C and 8D provides the same degrees of freedom of orientation. Configured as shown in FIG. 8E, coaxial heads 800 and 870 can be used in similar fashion to the connector 160 shown in FIG. 6H to assemble a multilevel dynamic stabilization assembly similar to that shown in FIG. 6H.

FIG. 8F shows an example of a polyaxial screw 890 having a polyaxial head 892 which is permanently attached to a bone anchor 896. The components of polyaxial head 892 are identical to those of coaxial head 800 with the exception of yoke 810. The yoke 894 of polyaxial head 892 is permanently attached to the bone anchor 896. Yoke 894 may, in some case, be formed in one piece with bone anchor 896. In other cases, yoke 894 may be formed separately from bone anchor 896 and subsequently attached by welding or another bonding technique. Note that yoke 894, therefore, may not be rotated without also rotating bone anchor 896. Thus, polyaxial head 892 provides two degrees of freedom of orientation with respect to rod placement and a third degree of freedom only if variable rotation of the bone anchor is possible in the particular application. Note also, an alternative embodiment of polyaxial screw 890 uses the side entry saddle 880 of FIG. 8D in place of the regular saddle 830 of FIG. 8B.

Compound Deflection Rods

In some embodiments, it is desirable to utilize vertical rods which incorporate deflection rods. Deflection rods are useful to allow for controllable compression and/or extension of the length of the vertical rod and consequently the distance between the bone anchors secured to either end of the vertical rod. Vertical rods incorporating deflection rods function to stabilize the spinal segment in which the bone anchors while still allowing a controllable amount of motion. Rods which incorporate a linkage are referred to herein as compound rods. Rods incorporating a linkage which includes at least one deflection element are referred to herein as compound deflection rods. Compound deflection rods function as part of the deflection system to provide load sharing as part of a dynamic stabilization assembly.

Figure 9A:
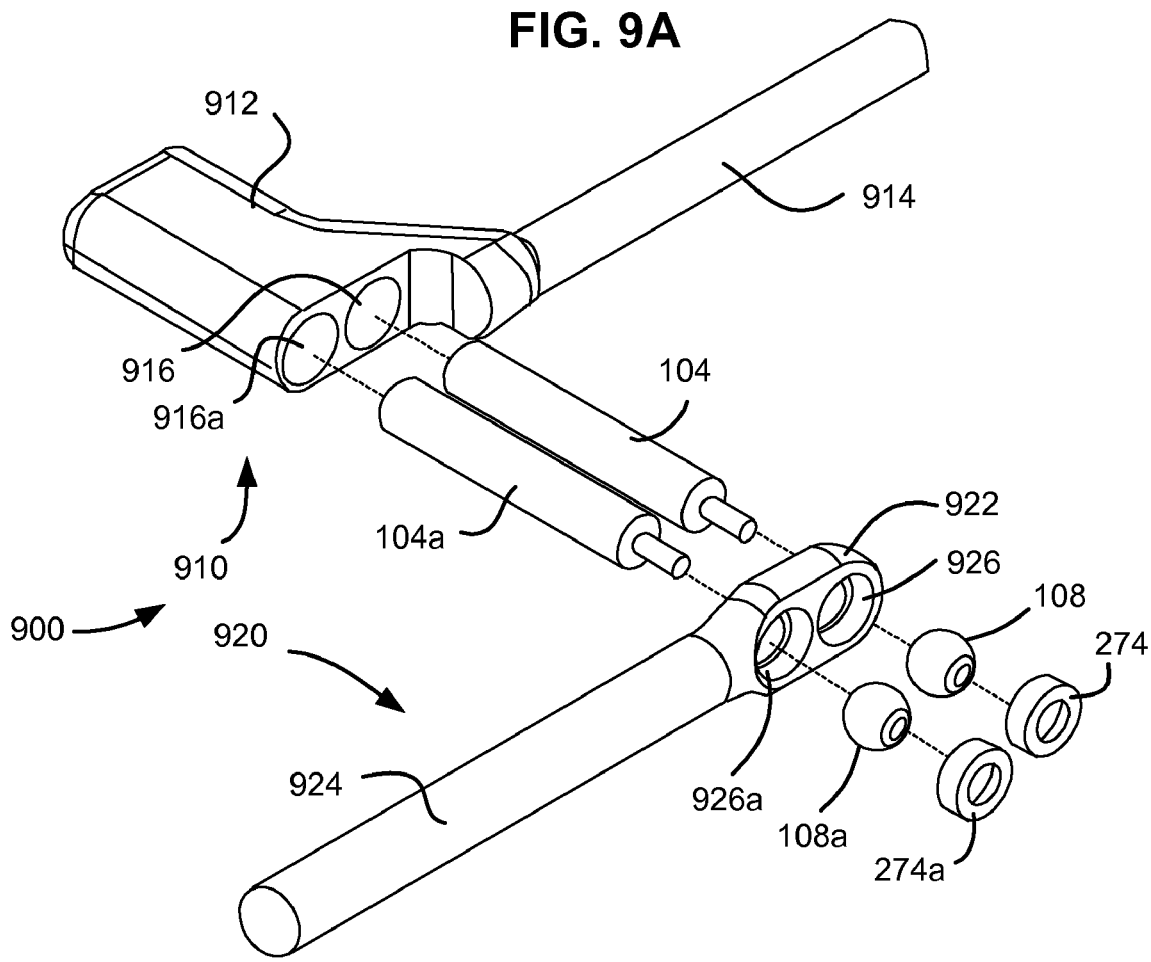
FIGS. 9A and 9B are perspective and exploded views of a compound deflection rod assembly and its components in accordance with an embodiment of the present invention.
Figure 9B:
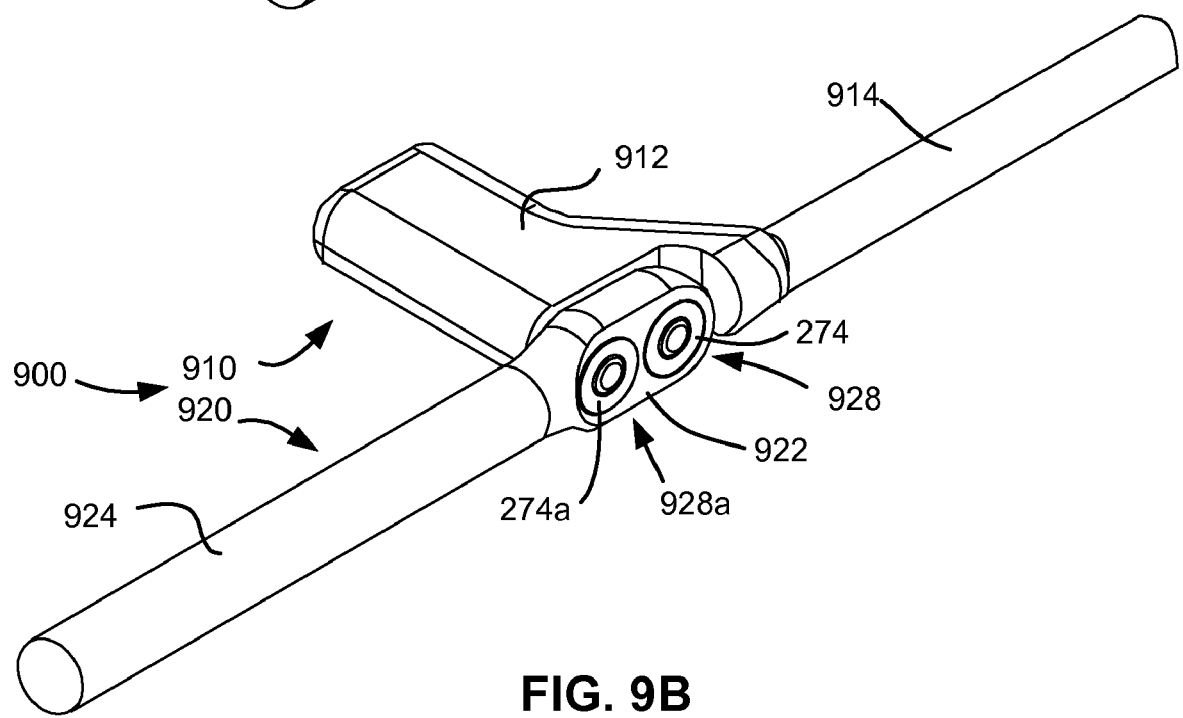

FIGS. 9A and 9B show one example of a compound deflection rod 900. FIG. 9A, shows an exploded view of compound deflection rod 900 revealing the main components of compound deflection rod 900 including first rod 914, second rod 924, housing 912, deflection rods 104 and 104a, balls 108, 108a and caps 274, 274a. FIG. 9B shows compound deflection rod 900 with the components assembled.

Referring to FIG. 9A, first rod 914 is connected to housing 912. Preferably first rod 914 and housing 912 are formed in one piece however they may be made separately and then securely and rigidly attached to each other. Housing 912 has two pockets 916, 916a each of which is sized to receive a deflection rod 104, 104a. A first deflection rod 104 is inserted into pocket 916 and secured to housing 912. A second deflection rod 104a is inserted into pocket 916a and secured to housing 912. Deflection rods 104, 104a may be any of the deflection rods discussed herein. Deflection rods 104, 104a may include a shield/guide, or the guide surface may instead be integrated into the pockets 916, 916a of the housing 912.

Second rod 924 is connected to a housing 922. Preferably, second rod 924 and housing 922 are formed in one piece; however, they may be made separately and then securely and rigidly attached to each other. Housing 922 includes two pockets 926, 926a into which the free ends of the deflection rods 104, 104a can be positioned. When positioned in pockets 926, 926a, balls 108, 108a are attached to deflection rods 104, 104a. Caps 274, 274a are then secured over balls 108, 108a securing the deflection rods 104, 104a to the housing 922.

Referring to FIG. 9B, each ball 108, 108a forms a ball joint 928, 928a in combination with the respective pockets 926, 926a and caps 274, 274a of FIG. 9A. When assembled, first rod 914 can move relative to second rod 924. The movements of first rod 914 relative to second rod 924 is constrained by the linkage comprising the two deflection rods 104, 104a and the two ball joints 928, 928a. The principle modes in which compound deflection rod 900 can move include compression along the longitudinal axis, expansion along the longitudinal axis, and bending at the ball joint (approximately in the plane perpendicular to the axes of the deflection rods 104, 104a). Relative movement of the first and second rods in each of these modes requires deflection of the deflection rods 104, 104a. The deflection/force curve for each of these movement modes can, therefore, be controlled by controlling the force deflection curves of the deflection rods in the manner previously discussed.

Figure 9C:
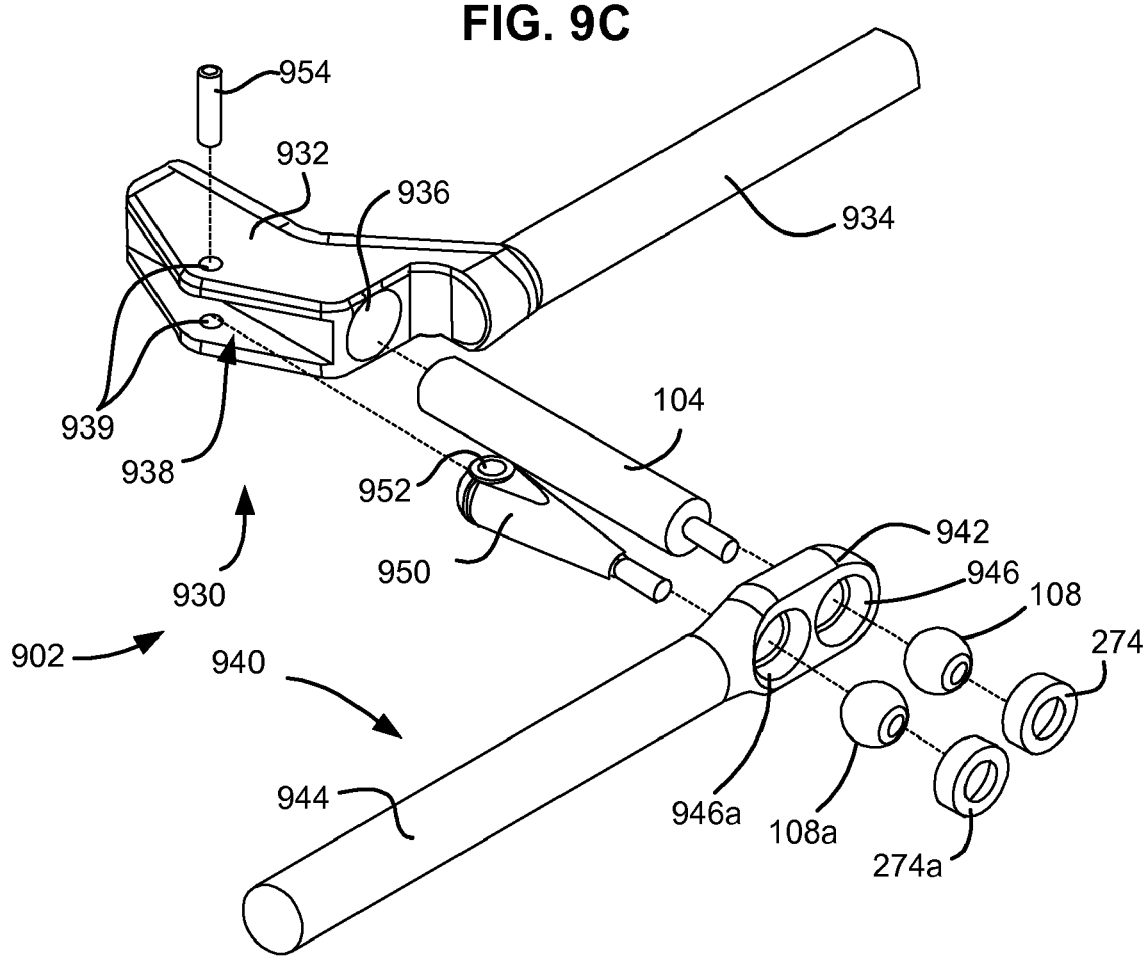
FIGS. 9C and 9D are perspective and exploded views of an alternative compound deflection rod assembly and its components in accordance with an embodiment of the present invention.
Figure 9D:
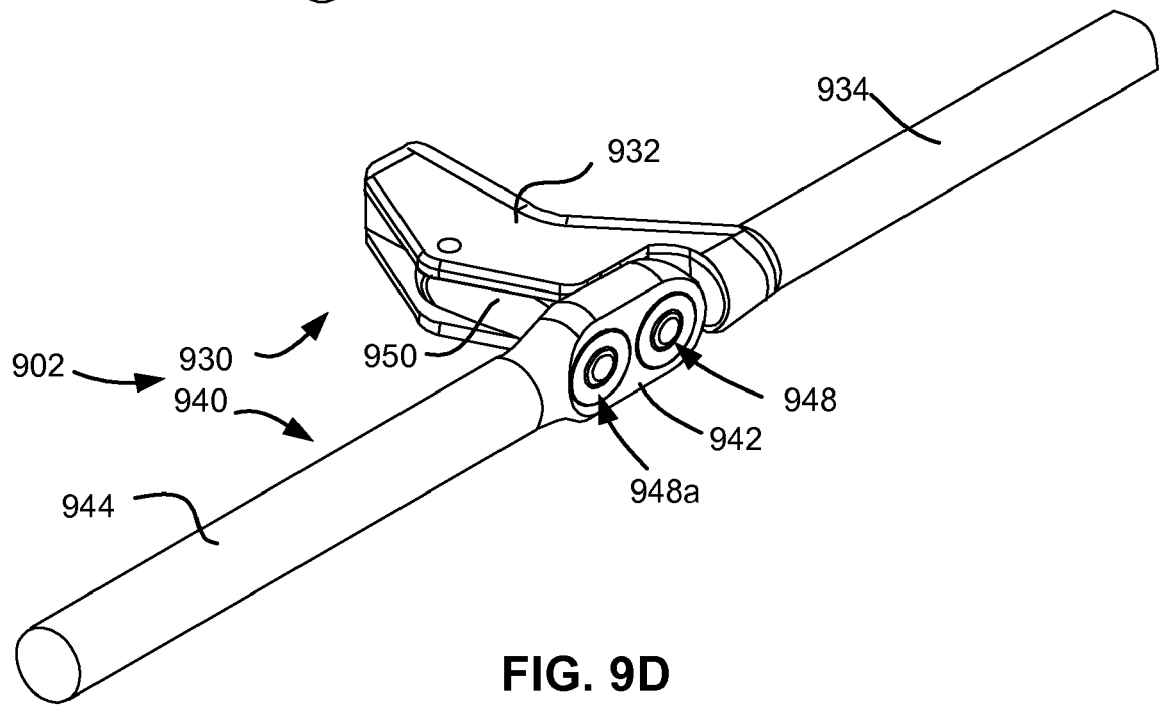

FIGS. 9C and 9D show a second example of a compound deflection rod 902. FIG. 9C, shows an exploded view of compound deflection rod 900 revealing the main components of compound deflection rod 900 including first rod 934, second rod 944, housing 932, deflection rod 104, arm 950, balls 108, 108a and caps 274, 274a. FIG. 9D shows compound deflection rod 900 with the components assembled.

Referring to FIG. 9C, first rod 934 is connected to housing 932. Preferably, first rod 934 and housing 932 are formed in one piece however they may be made separately and then securely and rigidly attached to each other. Housing 932 has one pocket 936 which is sized to receive a deflection rod 104. Deflection rod 104 is inserted into pocket 936 and secured to housing 932. Deflection rod 104 may be any of the deflection rods discussed herein. Deflection rod 104 may include a shield/guide, or the guide surface may instead be integrated into the pocket 936 of the housing 932.

Housing 932 also has a slot 938 for receiving arm 950; slot 938 includes two apertures 939. Arm 950 has an aperture 952 in the base which is aligned with the two apertures 939 of slot 938 in housing 932. A pivot pin 954 is then used to secure arm 950 to housing 932 while allowing arm 950 to pivot relative to the axis of the pin 954.

Second rod 944 is connected to a housing 942. Preferably, second rod 944 and housing 942 are formed in one piece however they may be made separately and then securely and rigidly attached to each other. Housing 942 includes two pockets 946, 946a into which the free ends of deflection rod 104 and arm 950 can be positioned. When positioned in pockets 946, 946a, balls 108, 108a are attached to the free ends of deflection rod 104 and arm 950. Caps 274, 274a are then secured over balls 108, 108a securing the deflection rod 104 and arm 950 to the housing 942.

Referring to FIGS. 9C and 9D, each ball 108, 108a forms a ball joint 948, 948a in combination with the respective pockets 946, 946a and caps 274, 274a. When assembled, first rod 934 can move relative to second rod 944. The movement of first rod 934 relative to second rod 944 is constrained by the linkage comprising deflection rod 104, arm 950 and two ball joints 948, 948a. The principle modes in which compound deflection rod 900 can move include compression along the longitudinal axis, expansion along the longitudinal axis, and bending at the ball joint (approximately in the plane perpendicular to the axes of the deflection rods 104, 104a of FIG. 9A). Relative movement of the first and second rods in each of these modes requires deflection of the deflection rods 104, 104a. The compound deflection rod 902 will be stiffer with respect to the bending modes compared to compound deflection rod 900 because the arm is constrained to a single axis of movement. The deflection/force curve for each of these movement modes can therefore be controlled by controlling the force deflection curves of the deflection rods in the manner previously discussed.

Dynamic Bone Anchors, Vertical Rods And Assemblies

Figure 10A:
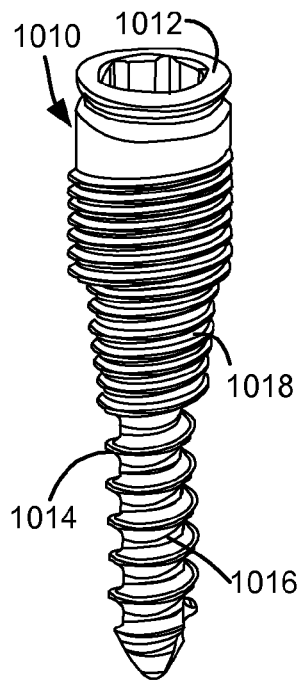
FIGS. 10A to 10E are perspective views of bone anchors in accordance with alternative embodiments of the present invention.

FIGS. 10A though 10E illustrate some possible variations in bone anchors of the anchoring system. The bone anchors each have a housing compatible with the deflections rods of the deflection system and the coaxial and offset heads/connectors of the connector system.

Bone anchor 1010 of FIG. 10A is a bone screw having a threaded region 1014 which extends up over most of a housing 1012. The threaded region 1014 may extend over a greater or lesser amount of housing 1012 depending upon such factors as the length of the bone screw, the type of bone in which the screw is to be implanted and the desired height to which the housing 1012 will extend above the bone surface after implantation. Note also that the distal thread depth 1016 may be deeper than the proximal thread depth 1018.

Figure 10B:
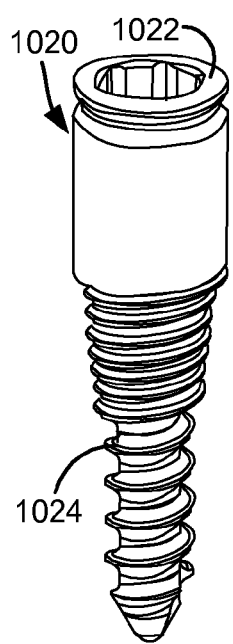

Bone anchor 1020 of FIG. 10B is a bone screw in which the screw-only section 1024 is shorter in length than in bone screw 1010 of FIG. 10A. Different lengths of screw-only section may be useful in different patients or different vertebrae as the size of the bone in which the anchor needs be implanted may vary considerably. Note however, that housing 1022 is the same size and shape as the housings of the other bone anchors so as to be compatible with the deflection system and connection system.

Figure 10C:
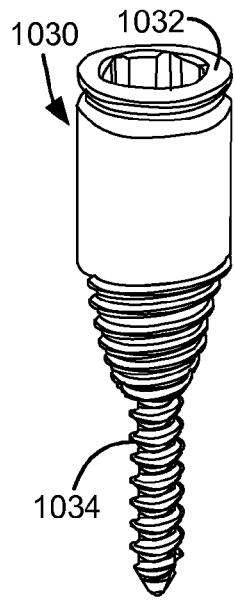

Bone anchor 1030 of FIG. 10C is a bone screw in which the screw-only section 1034 has a smaller diameter and is shorter in length than in bone screw 1010 of FIG. 10A. Different diameters of screw-only section may be useful in different patients or different vertebrae as the size of the bone in which the anchor needs be implanted may vary considerably. Note however, that housing 1032 is the same size and shape as the housings of the other bone anchors so as to be compatible with the deflection system and connection system.

Figure 10D:
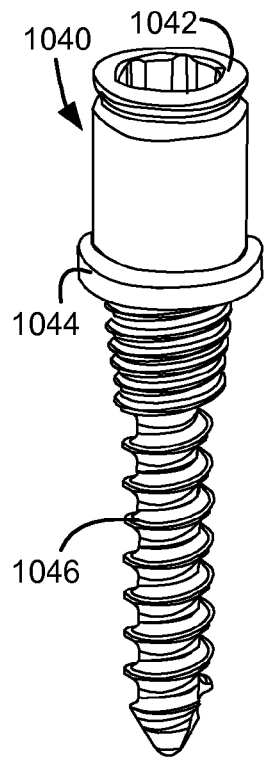

Bone anchor 1040 of FIG. 10D is a bone screw in which the housing 1042 has a rim 1044 extending away from housing 1042 where it transitions to the threaded region 1046. Rim 1044 may serve to retain an offset head mounted to housing 1042 in a way that it can rotate freely around housing 1042 during installation. Rim 1044 may also serve to widen the contact area between the bone anchor 1040 where it meets the bone of the vertebra. This can act as a stop preventing further insertion. This can also provide a wide basis stabilizing the housing against lateral motion and torque. Note that housing 1042 is the same size and shape as the housings of the other bone anchors so as to be compatible with the deflection system and connection system.

Figure 10E:
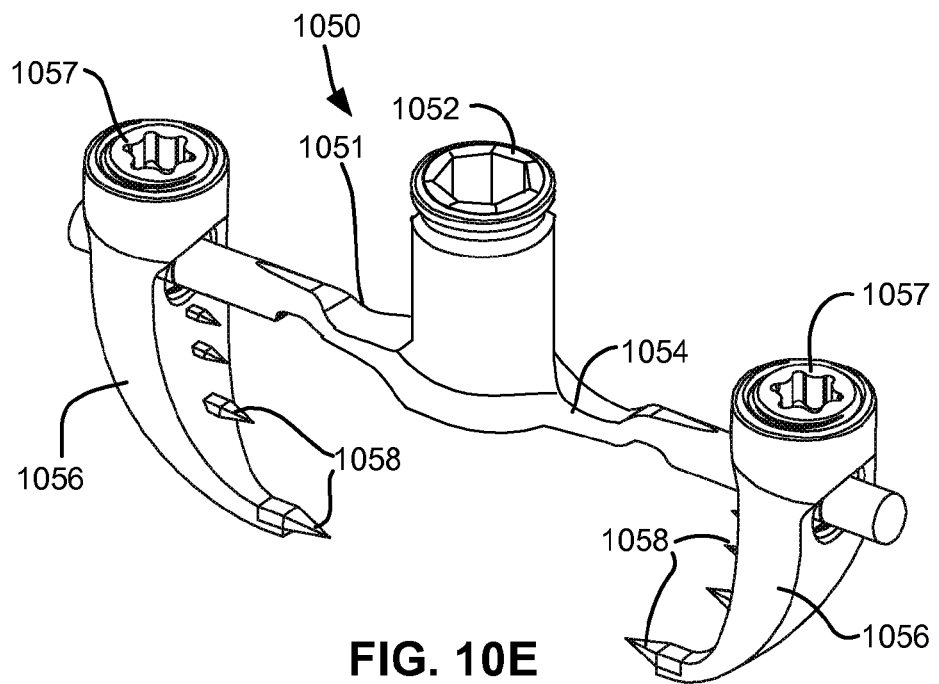

Bone anchor 1050 of FIG. 10E illustrates a bone hook device 1051 having a housing 1052. Bone hook device 1051 comprises a bar 1054 to which housing 1052 is rigidly connected. At either end of bar 1054 is a bone hook 1056 having a set screw 1057 for securing the bone hook 1056 to the bar 1054. Each bone hook 1056 has a plurality of sharp points 1058 for engaging and securing the bone hook 1056 to a vertebra. During use, the bone hooks 1056 are urged towards each other until the sharp points engage and/or penetrate the surface of a bone. Set screws 1057 are tightened to secure bone hooks 1056 in position relative to bar 1054 and thus secure housing 1052 relative to the bone. Different arrangements of bone hooks and bars may be made suitable for attachment of the housing 1052 to different types, sizes, shapes and locations of vertebra. Note that housing 1052 should the same size and shape as the housings of the other bone anchors so as to be compatible with the deflection system and connection system.

FIG. 11A shows an alternative embodiment of a bone anchor deflection rod assembly. Bone anchor 1120 of FIG. 11A is a bone screw having a threaded region 1124 and a housing 1130. A deflection rod 1104 is assembled with bone anchor 1120 and is secured within housing 1130 by threaded collar 1110. Threaded collar engages threads interior to housing 1130. Collar 1110 has two apertures 1111 which may be engaged by a pin wrench to tighten collar 1110 to housing 1130. Collar 1110 may also be welded to housing 1130 to further secure deflection rod 1104 to housing 1130. In this embodiment, deflection rod 1104 is designed to be preassembled with bone anchor 1120 prior to implantation.

As shown in FIG. 11A, the exterior of housing 1130 is provided with surface features in the form of a plurality of splines 1136. Splines 1136 are oriented parallel to the longitudinal axis of bone anchor 1120 and project from housing 1130 at regular intervals. FIG. 11B shows a plane view of bone anchor 1120 and deflection rod 1104 observed from the deflection rod end of the assembly. As shown in FIG. 11B, there are 16 splines 1136 evenly spaced around the perimeter of housing 1130. The diameter of collar 1110 is the same or smaller as the minimum diameter of housing 1130 in the region of the splines to allow engagement of the splines by a complementary tool or connector without interference from collar 1110. In other embodiments, there may be a greater or lesser number of splines.

FIG. 11B shows a sectional view of a socket wrench 1140. Socket wrench 1140 has a plurality of splines 1146 complementary to splines 1136 of housing 1130. Socket wrench 1140 may therefore be slipped over deflection rod 1104 and housing 1130 and positioned as shown in FIG. 11B. When in position, socket wrench 1140 may be used to rotate housing 1130 to install bone anchor 1120 in a bone (or remove the bone anchor from the bone). Socket wrench 1140 should be complementary in interior profile to the exterior profile of housing 1130. Socket wrench 1140 need not have as many splines 1146 as housing 1130 has splines 1136 so long as the splines 1146 are correctly positioned to engage some or all of the splines 1136 of housing 1130. An open wrench or other driver may be designed with the same engagement surface to engage some or all of the splines 1136 of housing 1130.

The various connectors discussed herein that engage the housing of a bone anchor may be readily adapted to engage splines 1136 of housing 1130. By way of example, FIG. 11C shows in-line connector 300 of FIGS. 3A-3F adapted to engage splines 1136. In-line connector 300 mounts externally of the housing 1130 of a bone anchor 1120. The components of in-line connector 300 shown in FIG. 11B include locking set screw 306, clamp ring 310, saddle 320 and plunger 330. As shown in FIG. 11B, clamp ring 310 has, on the inside diameter, a plurality of splines 1156 complementary to splines 1136 of housing 1130. Clamp ring 310 may, therefore, be slipped over deflection rod 1104 and housing 1130 and positioned as shown in FIG. 11C after implantation of bone anchor 106 in a vertebra. Splines 1156 engage splines 1136 of housing 1130. Clamp ring 310 is prevented by splines 1156 and 1136 from free rotation around housing 1130. This is advantageous in that increases the stability of the dynamic stabilization assembly by preventing the clamp ring 310 from slipping around housing 1130 under load. When clamp ring 310 is positioned at the desired angle relative to bone anchor 1120, set screw 306 may be tightened onto a vertical rod (not shown) to clamp the vertical rod to the saddle 320 and also tighten clamp ring 310 against the surface of housing 1110 (as previously described with respect to FIGS. 3A-3F). Thus, connector 300 may be used to securely attach a vertical rod to the housing of bone anchor 1120.

Clamp ring 310 (and thus connector 300) may be installed in any of 16 positions around housing 1130 (22.5 degrees separation between positions). If smaller granularity of positioning is required, a larger number of splines may be used. Clamp ring 310 should be complementary in interior profile to the exterior profile of housing 1130. Clamp ring 310 need not have as many splines 1156 as housing 1130 has splines 1136 so long as the splines 1156 are correctly positioned to engage some or all of the splines 1136 of housing 1130. A clamp ring 310 as shown in FIGS. 3A-3F without any splines may still be used to engage housing 1130.

The other connectors discussed herein may be similarly adapted to engage the splines 1136 of housing 1130 of bone anchor 1120. Likewise, the other bone anchors discussed herein may be provided with splines on the exterior of the housing to facilitate installation and enhance the mounting of connectors. In alternative embodiments, different surface features may be utilized on the surface of a housing for engagement by a tool or connector. For example, a housing may be made polygonal in exterior section and have 8, 10, 12, 16 or more sides.

Likewise, a tool or connector for use with such a housing would have a complementary interior profile designed to engage the 8, 10, 12, 16 or more sides. Alternatively, a housing may be provided with a plurality of apertures at regular intervals. A tool or connector for use with such a housing may be provided with a one or more of pins designed to engage the apertures in a plurality of positions in the manner of a pin wrench. Conversely, the housing may be provided with one or more protruding pins and the tool or connector with a plurality of complementary apertures. Alternatively, one or both of the housing and connector may be provided with shallow surface features such as dots, dimples, ridges or the like designed to increase the frictional engagement of the housing and connector. In the latter case, the features of the housing and connector need not necessarily be complementary to one another and the connector and housing may be free to engage one another at any angular position.

Figure 11D:
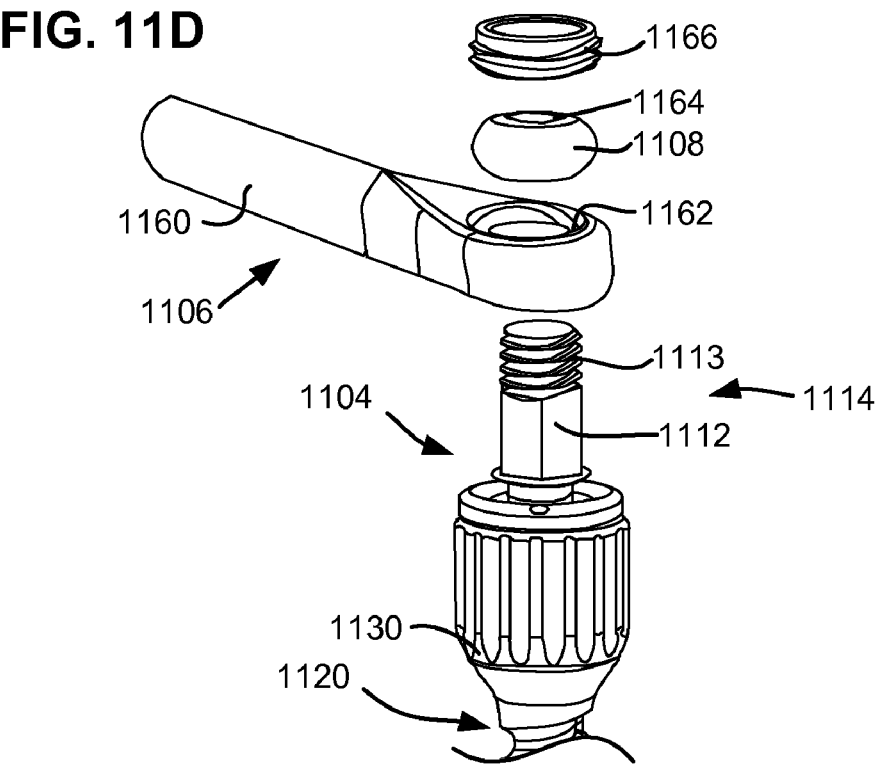
FIG. 11D is a perspective view showing a vertical rod for mounting to the deflection rod and bone anchor of FIG. 11A in accordance with an embodiment of the invention.

As with the previously described embodiments, deflection rod 1104 may be connected to a vertical rod. FIG. 11D illustrates a vertical rod 1106 for connection to deflection rod 1104. As shown in FIG. 11D, deflection rod 1104 has a mount 1114 which includes a polygonal section 1112 for secure mounting to a vertical rod 1106. Polygonal section 1112 may be hexagonal, octagonal or the like. Polygonal section 1112 shaped to match the shape of a receiver in vertical rod 1106. As shown in FIG. 11D, the proximal end of mount 1114 is threaded 1113 to receive a fastener to secure vertical rod 1106 to mount 1114.

FIG. 11D also shows a preferred embodiment of the vertical rod 1106 for use with deflection rod 1104. As shown in FIG. 11D, vertical rod 1106 comprises a rod 1160 which is preferably a 5.5 mm diameter titanium rod. Vertical rod 1106 has a pocket 1162 at one end sized to receive a ball 1108. Ball 1108 is preferably a cobalt chrome ball. Ball 1108 has a polygonal aperture 1162 designed to closely engage the polygonal section 1112 of mount 1114. Ball 1108 is inserted into pocket 1162 and secured into place with threaded cap 1166. Pocket 1162 is threaded to receive cap 1166. Ball 1108 is placed in pocket 1162 and then cap 1166 is screwed into the threaded portion of pocket 1162. Cap 1166 is preferably titanium and may be laser welded or otherwise secured to vertical rod 1160 after assembly. The components of vertical rod 1106—titanium rod 1160, titanium cap 1166 and cobalt chrome ball 1108 are assembled prior to use.

Figure 11E:
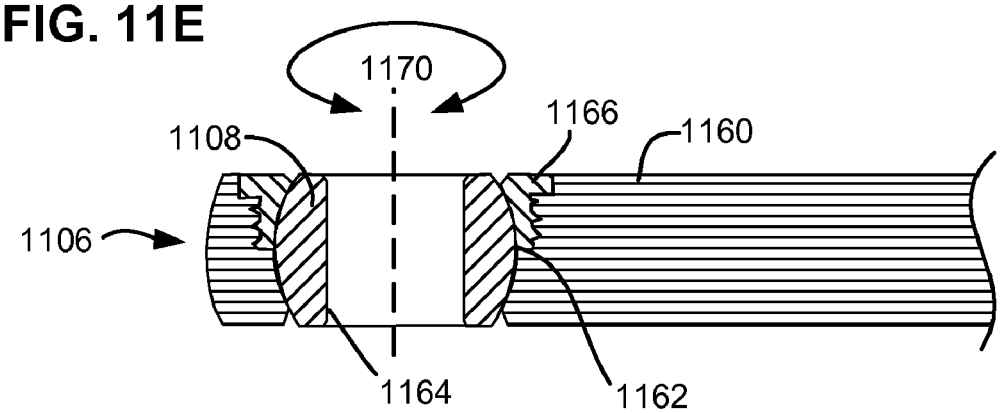
FIGS. 11E and 11F are sectional views showing components of the vertical rod of FIG. 11D.
Figure 11F:
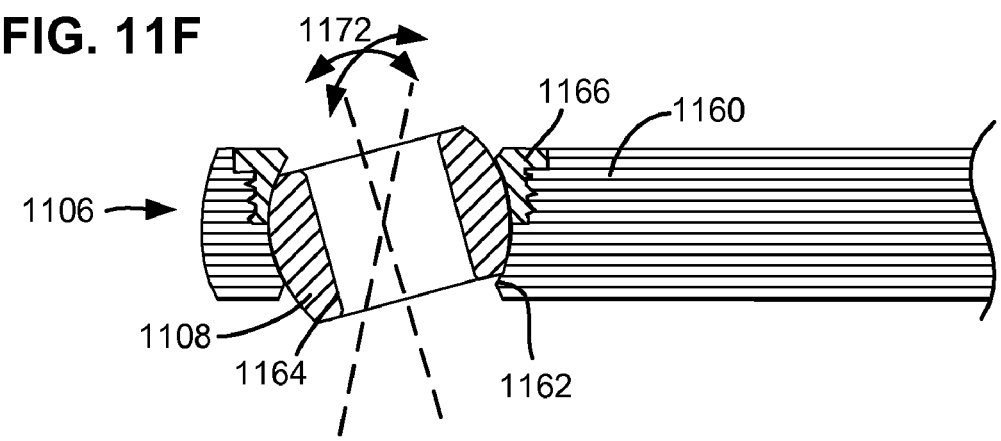

FIGS. 11E and 11F show a sectional view through vertical rod 1106 after assembly. FIG. 11E shows ball 1108 positioned within pocket 1162 of rod 1160. As shown in FIG. 11E, cap 1166 and pocket 1162 capture ball 1108 such that it cannot be removed from vertical rod 1160. Ball 1108 can, however, rotate 360 degrees around the axis of aperture 1162 as shown by arrow 1170. This allows vertical rod to rotate 360 degrees around the long axis of the deflection rod or bone anchor to which ball 1108 is mounted. Ball 1108 can also tilt from the position shown in FIG. 11F by arrows 1172. In a preferred embodiment, ball 1108 can tilt 15 degrees in any direction, therefore, allowing vertical rod 1106 to tilt 15 degrees from perpendicular relative to the deflection rod or bone anchor to which ball 1108 is mounted. Note that the mount 1114 (see FIG. 11D) and a nut to secure the vertical rod 1106 to mount 1114 are designed so not as to interfere with the range of motion either in rotation or tilting.

Figure 11G:
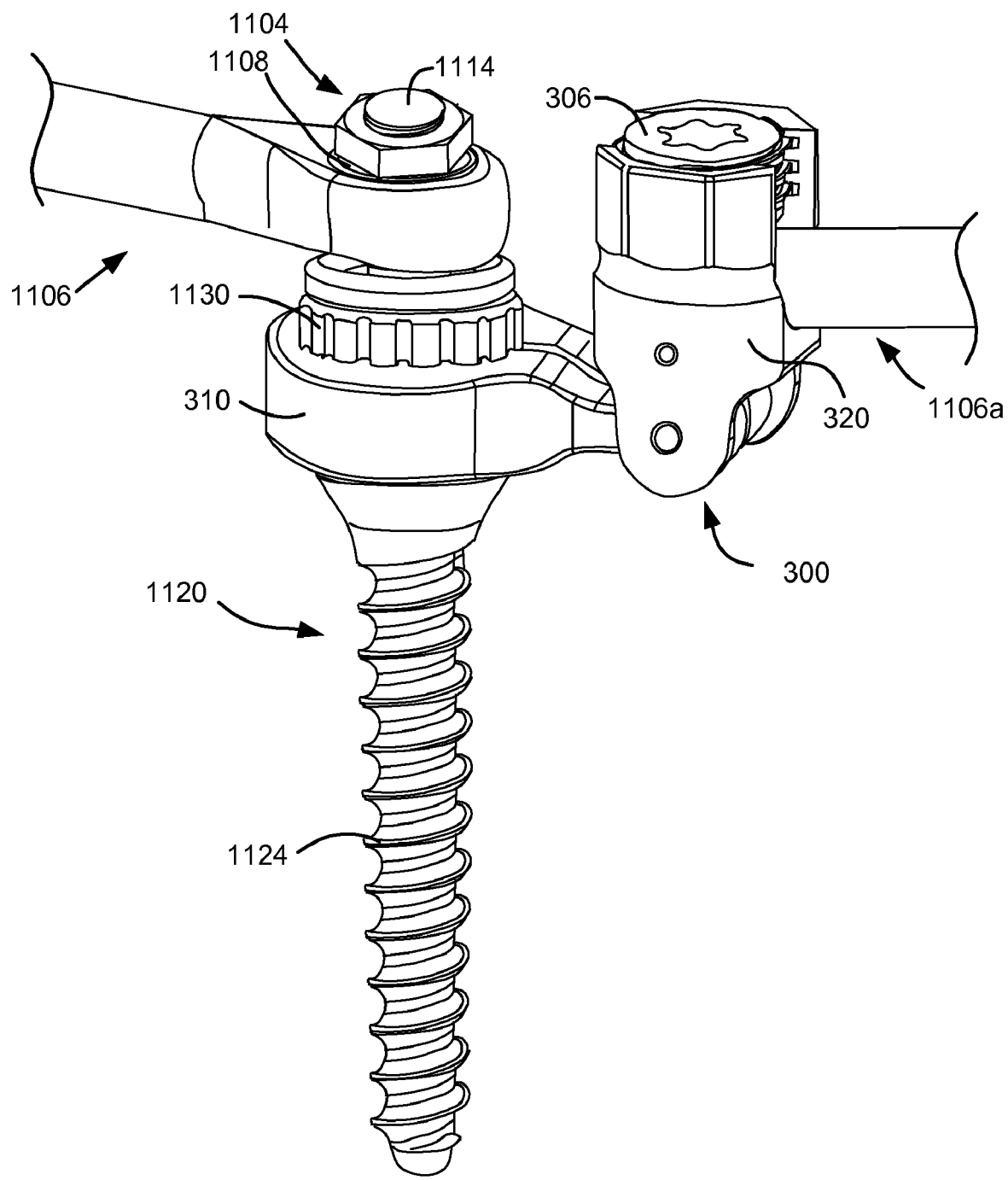
FIG. 11G shows an assembly comprising the bone anchor and deflection rod of FIG. 11A, the connector of FIG. 11C and the vertical rod of FIG. 11D.

FIG. 11G illustrates the subassembly resulting from mounting connector 300 of FIGS. 3A-3F to housing 1130 of bone anchor 1120 and also mounting vertical rod 1106 of FIGS. 11D, 11E, 11F. As shown in FIG. 11G, connector 300 connects bone anchor 1120 to a second vertical rod 1106a. Thus, bone anchor 1120 may be connected by vertical rod 1106, 1106a to bone anchors (not shown) on neighboring vertebrae to create a dynamic stabilization assembly which spans three vertebrae. The assembly may be used to create assemblies as illustrated for example, shown in FIGS. 1E, 1G, 3G, 4G, 5H, 6H, 11B-C and 11G. Additionally, the other connectors described herein may be utilized to create similar assemblies. Note that connector 300 provides sufficient degrees of freedom to connect vertical rod 1106a securely to housing 1130. During implantation, connector 300 may be adjusted to accommodate the angle from which vertical rod 1106a approaches bone anchor 1120. After adjustments are made, set screw 306 is tightened securing vertical rod 1106a to saddle 320, locking the angle of saddle 320 relative to clamp ring 310, and securing clamp ring 310 to housing 1130. Vertical rod 1106 is connected to mount 1114 of deflection rod 1104 by a ball 1108 such that vertical rod can rotate about deflection rod 1104 and pivot relative to deflection rod 1104. Deflection rod 1104 may also rotate within housing 1130 of bone anchor 1120 and pivot relative to housing 1130. The pivoting of deflection rod 1104 is controlled and or limited by components of deflection rod 1104 as described in greater detail in the applications referred to above and incorporated by reference herein.

Vertical rod 1106 may be used with a standard bone anchor, a deflection rod and bone anchor (for example bone anchor 1120 and deflection rod 1104 of FIG. 11A), or a polyaxial screw. Likewise, the assembly of deflection rod 1104 and bone anchor 1120 of FIG. 11A may be utilized with vertical rod 1106, but may also be utilized in conjunction with a vertical rod not having a ball joint. Likewise, any of the connectors described herein may be utilized to create assemblies with bone anchors, deflection rods and vertical rods as shown in FIG. 11G. Different connectors may be utilized in different circumstances as necessary and/or desirable in light of the anatomy of the patient and other surgical constraints.

Figure 12A:
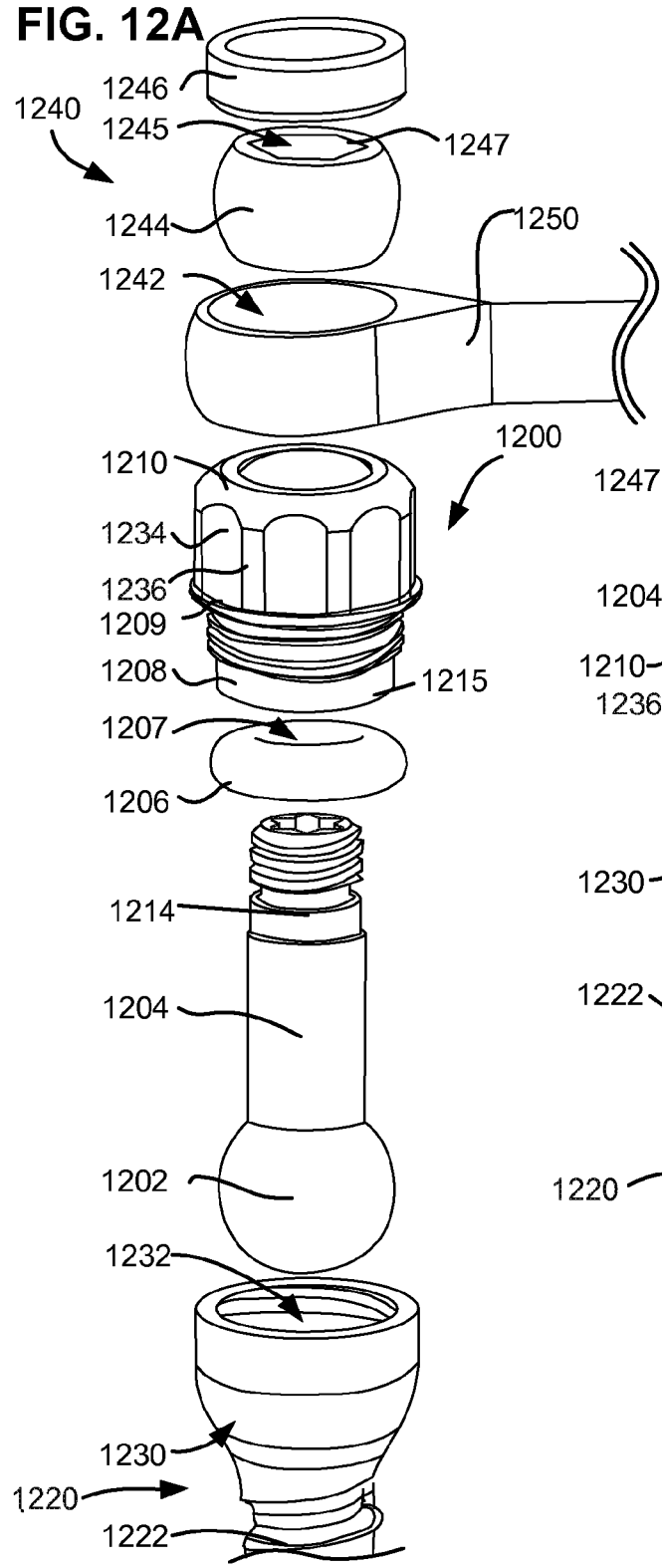
FIG. 12A is an exploded views of an alternative deflection rod assembly according to an embodiment of the present invention.
Figure 12B:
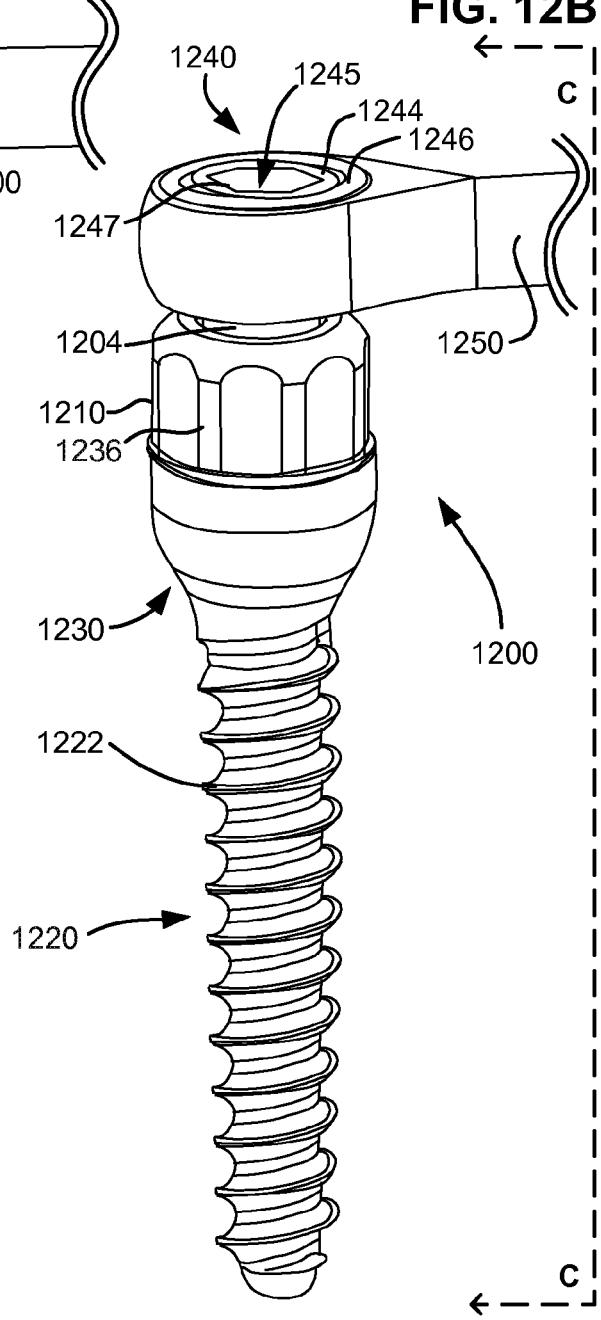
FIG. 12B is a perspective view of the deflection rod assembly of FIG. 12A, as assembled.

FIGS. 12A-12D illustrate an alternative deflection rod assembly 1200 which may be utilized with the connectors described above to make implantation assemblies for dynamic stabilization of the spine (such as, for example, shown in FIGS. 1E, 1G, 3G, 4G, 5H, 6H, 11B-C and 11G). In this embodiment, deflection rod assembly 1200 is incorporated into a bone anchor 1220 prior to implantation. FIG. 12A shows an exploded view of alternative deflection rod assembly 1200. FIG. 12B shows the deflection rod assembly combined with a bone anchor 1220 and vertical rod 1250. FIGS. 12C-12D show sectional views of deflection rod assembly 1200 and illustrate deflection of the deflection rod. As shown in FIG. 12A, deflection rod assembly 1200 includes four components: ball-shaped retainer 1202, deflectable post 1204, o-ring 1206 and cap 1210.

Deflectable post 1204 has a retainer 1202 at one end. Retainer 1202 is a spherical structure formed in one piece with deflectable post 1204. At the other end of deflectable post 1204 is a mount 1214. Mount 1214, in this embodiment, is suitable for connecting to a vertical rod. A ball may be used in place of mount 1214 as previously described. In this embodiment, mount 1214 is also formed in one piece with deflectable post 1204 and retainer 1202. This piece can preferably be made of cobalt chrome while, preferably, the rest of the bone anchor is made of titanium or stainless steel. The o-ring is made of a polymer as described below. In alternative embodiments, deflectable post 1204 may be formed separately from and securely attached to one or more of mount 1214 and retainer 1202 by laser welding, soldering or other bonding technology. Alternatively, deflectable post 1204 may be formed separately and mechanically engage one or more of mount 1214 and retainer 1202 using, for example, threads. For example, a lock ring, toothed locking washer, cotter pin or other mechanical device can be used to secure deflectable post 1204 to one or more of mount 1214 and retainer 1202. As shown in FIG. 12A, mount 1214 is a low profile mount configured to fit within a ball joint 1240 of a vertical rod component.

An alternative dynamic vertical rod 1250 is also illustrated in FIG. 12A. This dynamic vertical rod 1250 may be utilized with the connectors described above to make implantation assemblies for dynamic stabilization of the spine (such as, for example, shown in FIGS. 1E, 1G, 3G, 4G, 5H, 6H, 11B-C and 11G). As shown in FIG. 12A, ball 1244 is received in a spherical pocket 1242 in the end of vertical rod 1250. Ball 1244 is secured in spherical pocket 1242 by race 1246. The ball 1244 may be made of a material or treated to reduce wear on the ball caused by movement of ball 1244 in pocket 1242. Ball 1244 may, in some embodiments, be a cobalt chrome ball with the rest of the vertical rod made, preferably, of titanium or stainless steel. Race 1246 is secured to vertical rod 1250 by, for example, threads and/or laser welding. When secured, ball 1244 may rotate and pivot in the spherical pocket 1242.

Dynamic vertical rod 1250 is preferably assembled prior to implantation. Dynamic vertical rod 1250 may be attached to the mount 1214 of a deflectable post 1204 after implantation of the deflection rod assembly 1200 and bone anchor 1220 assembly into a vertebra. Ball 1244 has a central aperture 1245 designed to be secured to a mount 1214. Central aperture 1245 is threaded to enable ball 1244 to be secured to the threads of mount 1214. Central aperture 1245 also has a hexagonal section 1247 which may mate with a wrench and by which ball 1244 may be tightened to the threaded end of mount 1214. Advantageously, there is no nut extending beyond ball 1244 thus reducing the profile of the connection between mount 1214 and vertical rod 1250. Put another way, the ball 1244 acts as its own nut to secure ball 1244 to mount 1214. Ball joint 1240 allows greater range of motion and reduces torsional stresses on the dynamic stabilization assembly and the bones to which it is attached. In alternative embodiments, a separate nut or other fastener may be used to secure the dynamic vertical rod to a deflectable post.

Deflection rod assembly 1200 is configured to be mounted in a bone anchor 1220, which comprises a bone screw 1222 connected to a housing 1230. Housing 1230 has a cavity 1232 oriented along the axis of bone anchor 1220 at the proximal end and configured to receive deflection rod assembly 1200. In other embodiments, housing 1230 may be longer while cap 1210 may be a smaller part. Cap 1210, in this embodiment, is designed to perform multiple functions including securing o-ring 1206 as well as securing retainer 1202 in cavity 1232 of bone anchor 1220. In the embodiment of FIG. 12A, cap 1210 has an outer surface 1234 adapted for mounting a component, e.g. an offset connector. Housing 1230 may, in some embodiments, be cylindrical as previously described. The combination of deflection rod assembly integrated into a bone anchor may be referred to herein as a dynamic bone anchor.

As also shown in FIG. 12A, outer surface 1234 of housing 1230 is provided with splines/flutes or registration elements 1236. Splines/flutes 1236 may be engaged by a driver that mates with splines/flutes 1236 for implanting bone anchor 1220. Cap 1210, by integrating the functions of the collar and sleeve, reduces the complexity of the deflection rod assembly 1200 and also increases the strength of the deflection rod assembly 1200 or allows a reduction in size for the same strength. Cap 1210 comprises a cylindrical shield section 1208 connected to a collar section 1209. Cap 1210 is designed to mate with aperture 1232 of housing 1230. The shield section 1208 and collar section 1209 are preferably formed in one piece. However, they may be formed separately and then secured together. Shield section 1208 is threaded adjacent collar section 1209 in order to engage threaded aperture 1232. Cap 1210 may alternatively, or additionally, be joined to housing 1230 by, for example, laser welding. O-ring 1206 fits within a groove 1205 of shield 1208 of cap 1210 with the aperture 1207 aligned with the central bore of cap 1210 (see FIG. 12C). O-ring 1206 has a round central aperture 1207 for receiving the deflection post 1204 (see FIG. 12B).

Referring now to FIG. 12B, which shows a perspective view of a deflection rod assembly 1200 assembled with a bone anchor 1220. When assembled, deflectable post 1204 is positioned within cap 1210 which is positioned within housing 1230 of bone anchor 1220. O-ring 1206 (See FIG. 12A) is first positioned within shield 1208 of cap 1210. Deflectable post 1204 is then positioned through o-ring 1206 and cap 1210. Deflectable post 1204, o-ring 1206 and cap 1210 are then positioned within the cavity 1232 of housing 1230. The cap 1210 is then secured to the threaded proximal end of cavity 1232. Cap 1210 has splines/flutes 1236 for engagement by a wrench to allow cap 1210 to be tightened to housing 1230. Housing 1230 may be alternatively, or additionally, provided with splines/flutes or registration elements 1236. The flutes/splines 1236 are also useful to allow engagement of the cap/housing assembly by an implantation tool and/or by a connector. The flutes/splines or registration elements 1236 allow the cap/housing to be gripped and have torque applied to allow implantation or resist rotation of a connector. Cap 1210 may alternatively, or additionally, be laser welded to housing 1230 after installation to secure the components. Cap 1210 secures deflectable post 1204 and o-ring 1206 within cavity 1232 of bone anchor 1220. (See FIG. 12C).

As also shown in FIG. 12B, deflectable post 1204 extends out of housing 1230 and cap 1210 such that mount 1214 is accessible for connection to a vertical rod 1250. There is a gap between deflectable post 1204 and cap 1210 which permits deflection of deflectable post 1204 through a predefined range before deflection is limited by contact with cap 1210. After mount 1214 is inserted into pocket 1242 of vertical rod 1250, ball 1244 is threaded onto the threads of mount 1214 and tightened into place through central aperture 1245. A wrench may be used to engage hexagonal aperture 1247. Ball 1244 may alternatively, or additionally, be laser welded to mount 1214 after installation to secure the components. Race 1246 is then inserted into pocket 1242 securing ball 1244 within ball joint 1240.

FIG. 12C shows a sectional view of a deflection rod assembly 1200 assembled with a bone anchor 1220 along the axis indicated by line C-C of FIG. 12B. Retainer 1202 fits into a hemispherical pocket 1239 in the bottom of cavity 1232 of housing 1230. The bottom edge of cap 1210 includes a flange 1215 which secures ball-shaped retainer 1202 within hemispherical pocket 1239 while allowing rotation of ball-shaped retainer 1202. As shown in FIG. 12C, o-ring 1206 occupies the space between deflectable post 1204 and shield 1208 of cap 1210. In other embodiments, o-ring 1206 may sit between deflectable post 1204 and a housing of bone anchor 1220. O-ring 1206 is secured within groove 1205 of cap 1210. Cap 1210 thereby secures both retainer 1202 and o-ring 1206 within housing 1230. O-ring 1206 may be compressed by deflection of deflectable post 1204 towards shield 1208 in any direction. O-ring 1206 is a compliant member which exerts a centering force upon deflectable post 1204. Other shapes and configurations of compliant members may be used in other embodiments, including, for example, tubes, sleeves and springs arranged to be compressed by deflection of the deflectable post 1204 and exert a centering force upon deflectable post 1204. O-ring 1206 is preferably made from polycarbonate urethane (for example, Bionate®) or another hydrophilic polymer. This material is disclosed in U.S. Pat. No. 5,133,742, issued Jul. 28, 1992, and entitled and U.S. Pat. No. 5,229,431, issued Jul. 20, 1993, and entitled "Crack-Resistant Polycarbonate Urethane Polymer Prostheses and the Like," both of which are incorporated herein by reference.

The o-ring 1206 can act as a fluid lubricated bearing and allow the deflectable post 1204 to also rotate about the longitudinal axis of the deflectable post 1204 and the bone anchor 1220. Other materials and configurations can also allow the post to rotate about the longitudinal axis of the post and the bone anchor. As shown in FIG. 12C, vertical rod 1250 has been secured to mount 1214 by securing ball 1244 to mount 1214.

FIG. 12D illustrates the deflection of deflectable post 1204. Applying a force to mount 1214 through vertical rod 1250 and ball joint 1240 causes deflection of deflectable post 1204 of deflection rod assembly 1200. Initially, deflectable post 1204 pivots about a pivot point 1203 indicated by an X. Deflectable post 1204 may pivot about pivot point 1203 in any direction. Concurrently, or alternatively, deflectable post 1204 can rotate about the long axis of deflectable post 1204 (which also passes through pivot point 1203). In this embodiment, pivot point 1203 is located at the center of ball-shaped retainer 1202. As shown in FIG. 12D, deflection of deflectable post 1204 compresses the material of o-ring 1206. O-ring 1206 is compressed into groove 1205. Groove 1205 may be slightly wider than necessary to accommodate o-ring 1206 in order that o-ring 1206 may expand axially while being compressed radially. The extra space in groove 1205 reduces the possibility that o-ring 1206 will become pinched between deflectable post 1204 and the inside of cap 1210. The force required to deflect deflectable post 1204 depends upon the dimensions of deflectable post 1204, o-ring 1206, groove 1205 and shield 1208 of cap 1210 as well as the attributes of the material of o-ring 1206. The o-ring 1206 exerts a centering force back on deflectable post 1204 pushing it back towards a position coaxial with bone anchor 1220. Note that due to ball joint 1240, vertical rod 1250 may also pivot relative to deflectable post 1204 and rotate relative to deflectable post 1204 without compressing o-ring 1206.

After further deflection, deflectable post 1204 comes into contact with limit surface 1213 of collar 1209 (not shown). Limit surface 1213 is oriented such that when deflectable post 1204 makes contact with limit surface 1213, the contact is distributed over an area to reduce stress on deflectable post 1204. After deflectable post 1204 comes into contact with limit surface 1213, further deflection requires deformation (bending) of deflectable post 1204. In a preferred embodiment, deflectable post 1204 is a titanium post 5 mm in diameter. Deflectable post 1204 is relatively stiff, and the force required to deflect deflectable post 1204 therefore increases significantly after contact of deflectable post 1204 with cap 1210. In a preferred embodiment, deflectable post 1204 may deflect from 0.5 mm to 2 mm in any direction before making contact with limit surface 1213. More preferably, deflectable post 1204 may deflect approximately 1 mm before making contact with limit surface 1213.

Alternative Polyaxial Connector

Figure 13A:
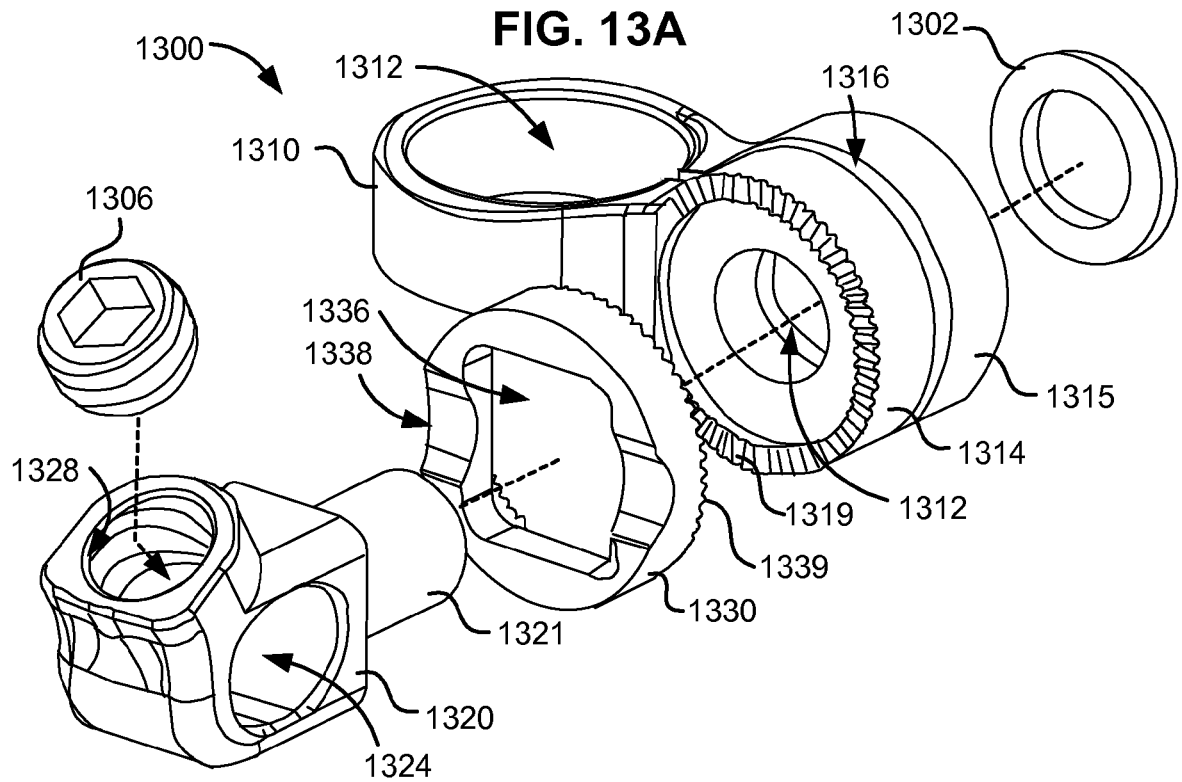
FIG. 13A is an exploded view of an alternative polyaxial connector and its components in accordance with an embodiment of the present invention.

FIGS. 13A-13E show an alternative embodiment of a side-swivel connector 1300 for connecting a bone anchor to a vertical rod with more degrees of freedom than the connector of FIG. 1E. Side-swivel connector 1300 mounts externally to the housing of a bone anchor and is, thus, an example of an offset head/connector. Side-swivel connector 1300 comprises five components and allows for two linear degrees of freedom and two angular degrees of freedom in connecting a vertical rod to a bone anchor. FIG. 13A shows an exploded view of the side-swivel connector 1300 revealing the components. The five components of side-swivel connector are weld ring 1302, locking screw 1306, clamp ring 1310, swivel 1320 and anchor ring 1330.

Clamp ring 1310 comprises a split ring having a gap 1316. Clamp ring 1310 has a central aperture 1312 sized to receive the housing of a bone anchor such that clamp ring 1310 can slide freely up and down the housing of a bone anchor and rotate around the housing while gap 1316 is open. However, when the gap 1316 is pushed closed, the clamp ring 1310 grips the housing and prevents the clamp 1310 from moving relative to the housing. Clamp ring 1310 has two disc-shaped ears 1314, 1315. A bore 1312 passes through the middle of both ears 1314, 1315. The outer surface of ear 1314 is provided with a plurality of radial splines 1319. Although not shown, the inner surface of bore 1312 may be provided with surface features to engage the outer surface of a bone anchor, for example, splines or surface texture. This will help resist slippage of clamp ring 1310 relative to a bone anchor after clamping.

Anchor ring 1330 is a disc-shaped component similar in shape to ears 1314, 1315. Anchor ring 1330 has a square channel 1336 therethrough. On one surface, anchor ring 1330 is with a plurality of radial splines 1339 for engaging the radial splines 1319 of ear 1314. On the other side of anchor ring 1330 is a rounded groove 1338 for engaging a vertical rod. Anchor ring 1330 is placed against ear 1314 of clamp ring 1310 with splines 1339 adjacent splines 1319.

As shown in FIG. 13A, swivel 1320 is a generally cube-shaped component having a channel 1324 therethrough for receiving a vertical rod. Swivel 1320 also has a threaded aperture 1328 sized to fit locking screw 1306. Swivel 1320 has a square section adapted to fit within the square channel 1336 of anchor ring 1330. Anchor ring 1330 can slide on the square section of swivel 1320. Swivel 1320 also has a cylindrical extension 1321 which is sized to fit through bore 1312 of ears 1314, 1315. Cylindrical extension 1321 is long enough to pass through both ears 1314 and 1315. Weld ring 1302 is welded to the end of cylindrical extension 1321 after it has been passed through anchor ring 1330 and both ears 1314, 1315. Cylindrical extension 1321 is in this way locked to ears 1314, 1315 by weld ring 1302. In alternative embodiments a different fastener or bonding technique may be used to secure the components together.

Figure 13B:
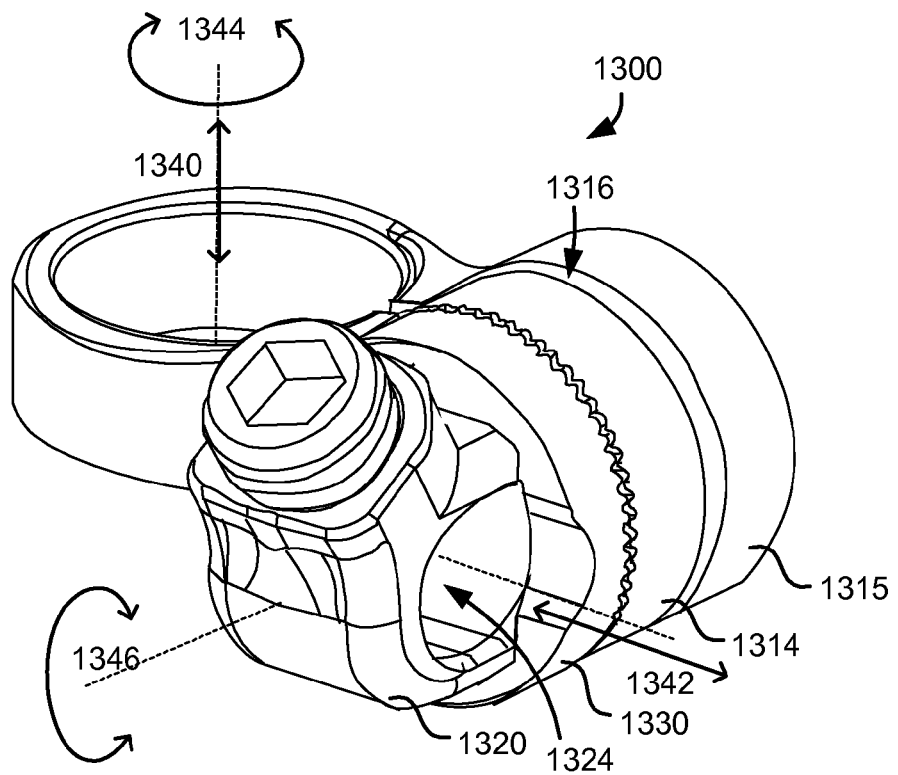
FIG. 13B is a perspective view of an alternative polyaxial connector in accordance with an embodiment of the present invention.

FIG. 13B, shows a perspective view of connector 1300 after assembly of the components. Weld ring 1302 (not shown) has been welded to the end of cylindrical extension 1321 after it has been passed through anchor ring 1330 and both ears 1314, 1315. Cylindrical extension 1321 is, thus, secured to ears 1314, 1315 by weld ring 1302. Weld ring 1302 secures swivel 1320, anchor ring 1330 and clamp ring 1310 to one another. Note that gap 1316 is still open. Cylindrical extension 1321 is positioned within the bore 1312 (not shown) of ears 1314 and 1315. Cylindrical extension 1321 may rotate in bore 1312 and thus swivel 1320 may rotate relative to clamp ring 1310 as shown by arrow 1346. Anchor ring 1330 may slide along square section of swivel 1320.

However, owing to the shape of square channel 1336, anchor ring 1330 cannot rotate relative to swivel 1320. Thus, swivel 1320 and anchor ring 1330 must rotate together, if at all. The anchor ring 1330 intersects a portion of channel 1324.

As also shown in FIG. 13B, side-swivel connector 1300 provides four degrees of freedom with respect to rod placement. Connector 1300 provides two linear degrees of freedom. First, clamp ring 1310 can slide up and down the housing of the bone anchor within the range of travel provided by the housing surface as shown by arrow 1340. Second, the rod can slide in and out of the channel 1324 of connector 1300 as shown by arrow 1342. These linear degrees of freedom are not necessarily orthogonal because the angle between the channel 1324 and the axis of the clamp ring 1310 is variable. However, during typical operation, the axis of channel 1324 and clamp ring 1310 will be approximately orthogonal and thus, the degrees of freedom are relatively independent. Connector 1300 also provides two angular degrees of freedom. First, clamp ring 1310 can rotate around the axis of the housing of a bone anchor as shown by arrow 1344. Second, the swivel 1320 of connector 1300 can pivot about the axis of the cylindrical extension 1321 (see FIG. 13A) of the swivel 1320 as shown by arrow 1346. This rotational axis is orthogonal to the axis of the bone anchor. These four degrees of freedom provide sufficient degrees of freedom to connect a vertical rod from one bone anchor to another bone anchor (so long as the linear and angular displacement is within range). Note that the axis of channel 1324 is slightly offset from the axis of clamp ring 1310, i.e. they do not intersect. In other embodiments, the components may be designed and/or configured so that the axes of these channels either intersect or have a greater offset.

Figure 13C:
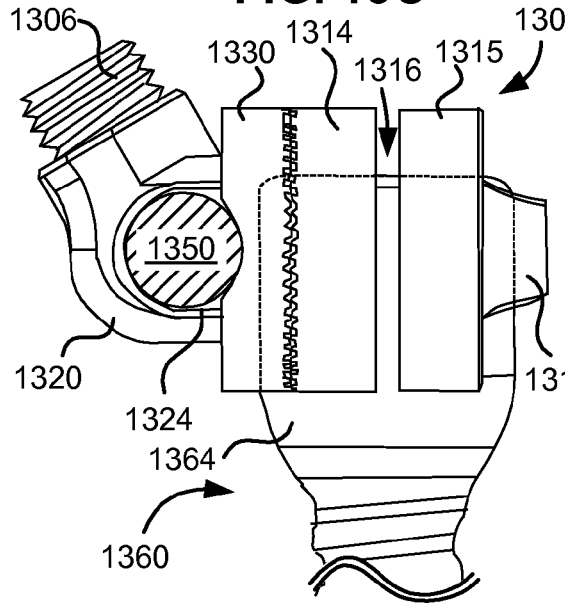
FIGS. 13C and 13D are views illustrating the clamping action of the polyaxial connector of FIGS. 13A and 13B.
Figure 13D:
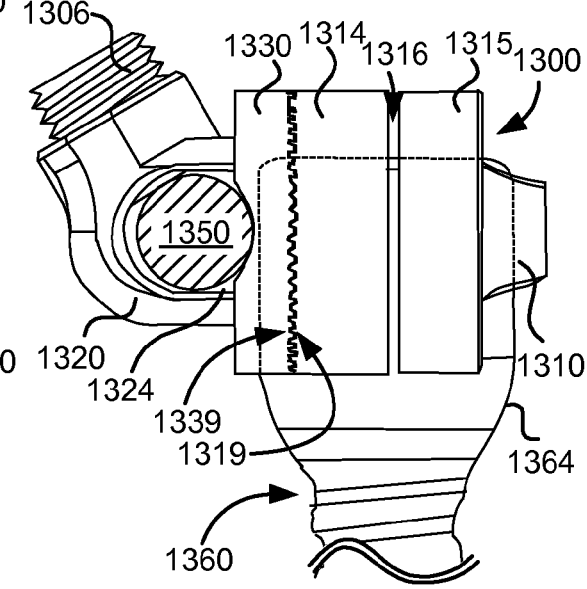

FIGS. 13C and 13D illustrate the clamping action of connector 1300 to clamp a rod 1350 (shown in section) to housing 1364 of bone anchor 1360. As shown in FIG. 13C, rod 1350 is received in channel 1324 of swivel 1320. Rod 1350 contacts anchor ring 1330 within curved groove 1338. Locking screw 1306 protrudes into channel 1324 and anchor ring 1330 intersects the other side of channel 1324. Clamp ring 1310 receives housing 1364 (shown by dashed lines) of a bone anchor 1360. Gap 1316 between ears 1314 and 1315 is still open so the clamp ring has enough room that clamp ring 1310 may slide up and down on housing 1364 and rotate around housing 1364.

As shown in FIG. 13D, when set screw 1306 is tightened against a rod 1350 within channel 1324 of connector 1300, the set screw 1306 pushes rod 1350 against anchor ring 1330 at the opposite side of channel 1324. Anchor ring 1330 is urged by rod 1350 against ear 1314 of clamp ring 1310. The anchor ring 1330 is thereby forced against the ear 1314 engaging the splines 1319 and 1339 and preventing further rotation of anchor ring (and thus swivel 1320) relative to clamp ring 1310. The force of anchor ring 1330 against ear 1314 also urges ear 1314 towards ear 1315 closing the gap 1316 in the clamp ring 1310. Ear 1315 is held in place by weld ring 1302 (See FIG. 13A). Closing gap 1316 locks clamp ring 1310 to housing 1364 and prevents further movement of clamp ring 1310 relative to housing 1364. Rod 1350 is likewise secured between set screw 1306 and anchor ring 1330 when gap 1316 is closed sufficiently to clamp housing 1364. Groove 1338 helps stabilize rod 1350 against rotation. In this way, operation of the single set screw 1306 serves to lock the clamp ring 1310 to the housing 1364 of the bone anchor 1360, fix the angle of swivel 1320 relative to clamp ring 1310 and secure rod 1350 within the channel 1324 of swivel 1320.

Figure 13E:
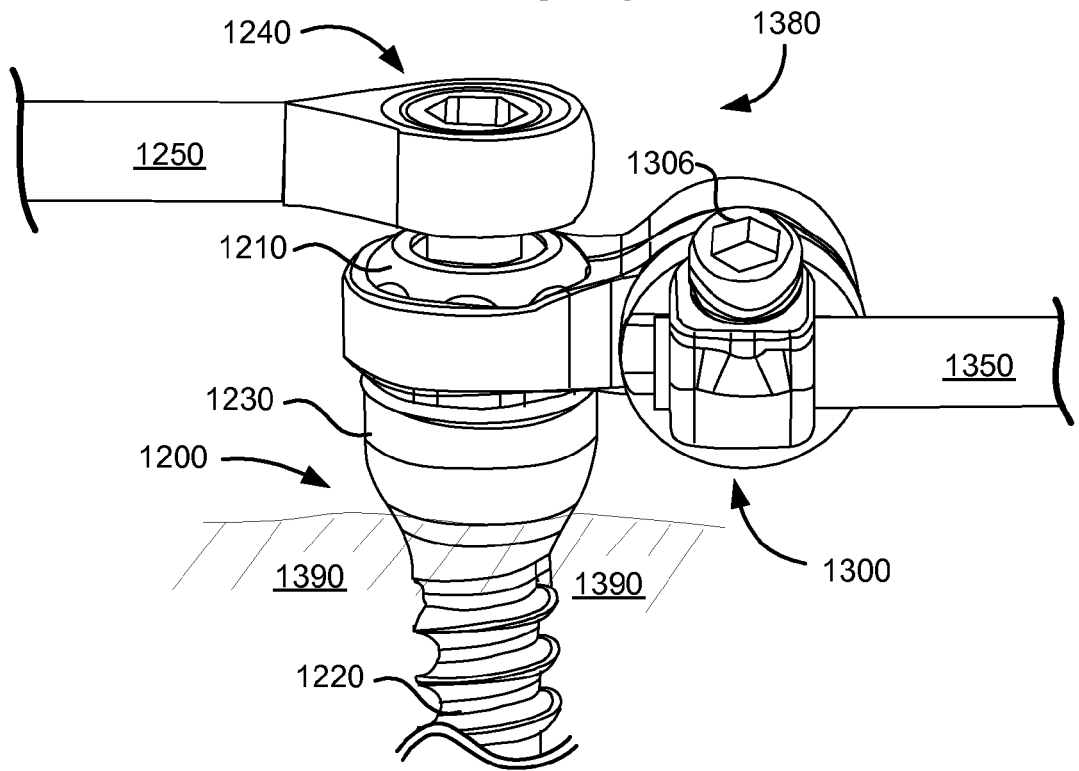
FIG. 13E is a lateral view of a partial spine stabilization assembly utilizing the polyaxial connector of FIGS. 13A to 13D in accordance with an embodiment of the present invention.

The side-swivel connector of FIGS. 13A-13D may be used to construct a dynamic stabilization assembly for one or more levels of the spine of a patient utilizing any of the other components herein described. FIG. 13E shows a partial view of an example of multi-level dynamic stabilization assembly 1380 utilizing the side-swivel connector 1300 of FIGS. 13A-13D. FIG. 13E shows how the components may be assembled and implanted in the spine of a patient to provide a multilevel dynamic stabilization assembly which provides dynamic stabilization of the spine and load sharing.

Referring to FIG. 13E, bone anchor 1220 is shown implanted in a bone of spine 1390, for example, a pedicle of a vertebra. As shown in FIG. 13E, housing 1230 of the bone anchor 1220 remains partly or completely exposed above the surface of the bone 1390. In this embodiment, deflection rod assembly 1240 is integrated with bone anchor 1220 prior to implantation. As shown in FIG. 13E, dynamic vertical rod 1250 is secured at one end to deflection rod assembly 1200 by ball joint 1240. The other end of dynamic vertical rod 1250 is anchored to a different level of the spine by a spine screw, for example a polyaxial spine screw or a polyaxial connector mounted to another dynamic bone anchor. Dynamic deflection rod 1250 in combination with deflection rod assembly 1200 provides controllable flexibility and load sharing over the level of the spine spanned while reducing stress on bone anchor 1220 and the bone 1390 in which it is implanted.

Vertical rod 1350 connects to the bone of the spine on the opposite side. Vertical rod 1350 is secured to cap 1210 of deflection rod 1240 and bone anchor 1220 by side-swivel connector 1300. During implantation, the direction and angle of vertical rod 1350 may be adjusted prior to locking side swivel connector 1300 by tightening set screw 1306. Vertical rod 1350 may be, for example, a dynamic vertical rod connected at its other end by a ball-joint to another deflection rod (not shown). Alternatively, vertical rod 1350 may be a conventional spinal rod fixed by a conventional bone screw to another bone of the spine possibly in conjunction with a fusion at that level. Assembly 1380 may be implanted in similar fashion as shown for example in FIG. 4G.

The dynamic stabilization assembly 1380 of FIG. 13E can provide dynamic stabilization at one or two levels of the spine. Alternatively dynamic stabilization may be provided at one level and fusion supported at the adjacent level. Connector 1300 and coaxial head dynamic rod 1250 permit assembly of dynamic stabilization assembly 1380 for a wide range of different patient anatomies and/or placement of bone anchors. Side-swivel connector 1300 is particularly useful where there is slight lateral displacement between the bone anchor positions on either side of a level.

Materials For Embodiments of the Invention

In addition to Nitinol or nickel-titanium (NiTi) other super elastic materials include copper-zinc-aluminum and copper-aluminum-nickel. However for biocompatibility, the nickel-titanium is the preferred material. As desired, the implant can, in part, be made of titanium or stainless steel. Other suitable material includes by way of example only polyetheretherketone (PEEK), polyetherketoneketone (PEKK), polyetherketone (PEK), polyetherketone-etherketoneketone (PEKEKK), and polyetheretherketoneketone (PEEKK), and polycarbonate urethane (PCU). Still, more specifically, the material can be PEEK 450G, which is an unfilled PEEK approved for medical implantation available from Victrex of Lancashire, Great Britain. (Victrex is located at www.matweb.com or see Boedeker www.boedeker.com). Other sources of this material include Gharda located in Panoli, India (www.ghardapolymers.com). Reference to appropriate polymers that can be used in the spacer can be made to the following documents. These documents include: PCT Publication WO 02/02158 A1, dated Jan. 10, 2002, entitled "Bio-Compatible Polymeric Materials;" PCT Publication WO 02/00275 A1, dated Jan. 3, 2002, entitled "Bio-Compatible Polymeric Materials;" and PCT Publication WO 02/00270 A1, dated Jan. 3, 2002, entitled "Bio-Compatible Polymeric Materials." In deflection rods where the deflectable post may rotate relative to the compliant member, the compliant member is preferably made of a hydrophilic polymer which can act as a fluid lubricated bearing (for example polycarbonate urethane such as for example Bionate ).

As will be appreciated by those of skill in the art, other suitable similarly biocompatible thermoplastic or thermoplastic polycondensate materials that resist fatigue, have good memory, are flexible, and/or deflectable have very low moisture absorption, and good wear and/or abrasion resistance, can be used without departing from the scope of the invention.

The foregoing description of preferred embodiments of the present invention has been provided for the purposes of illustration and description. It is not intended to be exhaustive or to limit the invention to the precise forms disclosed. Many embodiments were chosen and described in order to best explain the principles of the invention and its practical application, thereby enabling others skilled in the art to understand the invention for various embodiments and with various modifications that are suited to the particular use contemplated. It is intended that the scope of the invention be defined by the claims and their equivalents.

What is claimed is:

1. A spine stabilization assembly comprising a bone screw and a connector wherein:
   the bone screw has a longitudinal axis, a proximal end and a distal end,
   the bone screw has a housing at the proximal end,
   the housing has an exterior surface concentric with the longitudinal axis,
   the bone screw having a bore internal to the housing at the proximal end and coaxial the longitudinal axis,
   the bone screw including a deflection rod extending from the bore having a first end adapted to mount to a first spinal rod and a second end secured to the bone screw,
   the connector includes a clamp ring mounted on the exterior surface of the housing such that the clamp ring may be rotated around the longitudinal axis of the bone screw;
   a rod clamp is mounted on the clamp ring;
   a joint adjustably connects the clamp ring and the rod clamp allowing the rod clamp to rotate relative to the clamp ring;
   an aperture through the rod clamp sized and adapted to receive a second spinal rod;
   a fastening mechanism including a single fastener, wherein operation of the single fastener is adapted to secure a second spinal rod within the aperture, lock the connector and secure the clamp ring to the housing and
   the housing has a plurality of splines extending at intervals from the exterior surface and oriented parallel to the longitudinal axis of the bone screw;
   the clamp ring has a plurality of complementary splines;
   whereby the clamp ring may be secured in a plurality of discrete angular orientations about the housing and whereby the splines of the housing can engage the splines of the clamp ring to prevent rotation of the clamp ring when the clamp ring is secured to the housing.

2. The spine stabilization assembly of claim 1, wherein the joint adjustably connects the clamp ring and the rod clamp allowing the rod clamp to rotate relative to the clamp ring about a joint axis substantially perpendicular to the longitudinal axis of the bone screw.

3. The spine stabilization assembly of claim 2, wherein the joint axis intersects the longitudinal axis of the bone screw.

4. The spine stabilization assembly of claim 2, wherein the joint axis is offset from the longitudinal axis of the bone screw.

5. The spine stabilization assembly of claim 1, wherein the aperture is in-line with the longitudinal axis of the bone screw.

6. The spine stabilization assembly of claim 1, further comprising a second joint between the clamp ring and the rod clamp which allows the rod clamp to rotate relative to the clamp ring around a second joint axis perpendicular to the joint axis.

7. The spine stabilization assembly of claim 1, wherein the aperture of the rod clamp is offset from the housing.

8. A bone stabilization assembly comprising:
   a bone anchor having a longitudinal anchor axis;
   a housing fixed to one end of the bone anchor;
      the housing having an exterior surface coaxial with the anchor axis;
      the housing having an internal bore coaxial with anchor axis;
   a post extending from the bore the post being secured to the bone anchor in a manner that allows deflection of the post relative to bone anchor in response to a load;
   a clamp ring mounted on the exterior surface of the housing wherein the clamp ring may be positioned at a plurality of positions around the anchor axis relative to the housing;
   a rod clamp having a channel sized and adapted to receive a spinal rod along a channel axis;
   a rotary joint connecting the clamp ring and the rod clamp which allows the rod clamp to rotate relative to the clamp ring around a joint axis which is perpendicular to the anchor axis;
   a fastening mechanism including a single fastener, wherein operation of the single fastener is adapted to secure a spinal rod within the channel, lock the rotary joint and secure the clamp ring to the housing and
   the housing has a plurality of splines extending at intervals from the exterior surface and oriented parallel to the longitudinal axis of the bone screw;
   the clamp ring has a plurality of complementary splines;
   whereby the clamp ring may be secured in a plurality of discrete angular orientations about the housing and whereby the splines of the housing can engage the splines of the clamp ring to prevent rotation of the clamp ring when the clamp ring is secured to the housing.

9. The bone stabilization assembly of claim 8, wherein the channel axis intersects the anchor axis.

10. The bone stabilization assembly of claim 8, wherein the joint axis intersects the anchor axis.

11. The bone stabilization assembly of claim 8, wherein the joint axis does not intersect the anchor axis.

12. The bone stabilization assembly of claim 8, wherein:
   the channel axis intersects the anchor axis; and
   the joint axis is offset from the anchor axis.

13. The bone stabilization assembly of claim 8, wherein the channel of the rod clamp is offset from the housing.

14. The bone stabilization assembly of claim 8, further comprising a second joint between the clamp ring and the rod clamp which allows the rod clamp to rotate relative to the clamp ring around a second joint axis perpendicular to the joint axis.

15. A bone stabilization assembly comprising:
a bone anchor having a longitudinal anchor axis;
a housing fixed to one end of the bone anchor;
- the housing having an exterior surface coaxial with the anchor axis;
- the housing having an internal bore coaxial with anchor axis;

a post extending from the bore the post being secured to the bone anchor in a manner that allows deflection of the post relative to the bone anchor in response to a load;

a clamp ring mounted on the exterior surface of the housing wherein the clamp ring may be positioned at a plurality of positions around the anchor axis relative to the housing;

a rod clamp having a channel sized and adapted to receive a spinal rod along a channel axis;

the rod clamp being pivotally mounted to the clamp ring by a joint that allows adjustment of an angle between the channel axis and the longitudinal axis of the bone anchor;

a fastener adapted to secure a spinal rod within the channel, lock the angle between the channel axis and the longitudinal axis of the bone anchor, and secure the clamp ring to the housing and the housing has a plurality of splines extending at intervals from the exterior surface and oriented parallel to the longitudinal axis of the bone screw;

the clamp ring has a plurality of complementary splines;

whereby the clamp ring may be secured in a plurality of discrete angular orientations about the housing and whereby the splines of the housing can engage the splines of the clamp ring to prevent rotation of the clamp ring when the clamp ring is secured to the housing.

* * * * *